(12) United States Patent
Brennan et al.

(10) Patent No.: US 12,408,844 B2
(45) Date of Patent: Sep. 9, 2025

(54) IMPLANT FINDER

(71) Applicant: Senseonics, Incorporated, Germantown, MD (US)

(72) Inventors: James Brennan, Germantown, MD (US); Scott Lovald, Germantown, MD (US); Judd Day, Germantown, MD (US); Laura Popa, Germantown, MD (US); Fran Kaufman, Germantown, MD (US); Kelly Joy, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 114 days.

(21) Appl. No.: 18/130,673

(22) Filed: Apr. 4, 2023

(65) Prior Publication Data

US 2023/0309852 A1   Oct. 5, 2023

Related U.S. Application Data

(60) Provisional application No. 63/327,566, filed on Apr. 5, 2022.

(51) Int. Cl.
*A61B 5/06* (2006.01)
(52) U.S. Cl.
CPC .................. *A61B 5/062* (2013.01)
(58) Field of Classification Search
CPC .................. A61B 5/062; A61B 2034/2051
See application file for complete search history.

(56) References Cited

U.S. PATENT DOCUMENTS

| | | | |
|---|---|---|---|
| 6,263,230 B1* | 7/2001 | Haynor | A61B 34/20 600/424 |
| 2006/0025668 A1* | 2/2006 | Peterson | A61B 5/6887 600/407 |
| 2007/0276218 A1 | 11/2007 | Yellen | |
| 2015/0289754 A1* | 10/2015 | Bendory | A61B 1/32 600/104 |
| 2017/0027608 A1* | 2/2017 | Papadimitrakopoulos | A61B 17/3403 |
| 2017/0340243 A1* | 11/2017 | Jain | A61B 5/0084 |
| 2017/0347915 A1* | 12/2017 | Weprin | G01V 13/00 |
| 2018/0078329 A1 | 3/2018 | Hansen et al. | |
| 2018/0082480 A1* | 3/2018 | White | A61B 90/94 |
| 2021/0137412 A1* | 5/2021 | Sharma | G01R 33/022 |
| 2021/0338098 A1* | 11/2021 | Andreason | A61B 5/062 |

* cited by examiner

*Primary Examiner* — Anh Tuan T Nguyen
*Assistant Examiner* — Tommy T Ly
(74) *Attorney, Agent, or Firm* — Rothwell, Figg, Ernst & Manbeck, P.C.

(57) ABSTRACT

Method and apparatus for locating an implant comprising magnetic material and/or a charge storage device in a living animal. The apparatus may include a magnetic field generator (e.g., an electromagnetic field generator) configured to generate a magnetic field (e.g., an electromagnetic field). The apparatus may include a sensor configured to detect changes in the magnetic field and to generate a sensor signal indicative of the changes in the magnetic field. The magnetic material and/or the charge storage device of the implant may cause changes to the magnetic field as the sensor is moved over the implant. The apparatus may include a computer configured to use the sensor signal to detect a location of the implant.

30 Claims, 53 Drawing Sheets

Step 1: Set Midline

Step 2: Find center and edge of implant

Step 2: Find Center and Edge of implant

Step 3: Read Depth

Step 1: Find "Best" Orientation

Step 2: Find center and edge of implant

Step 3: Read Depth, Mark Entry

IMPLANT FINDER

CROSS-REFERENCE TO RELATED APPLICATION

The present application claims the benefit of priority to U.S. Provisional Application Ser. No. 63/327,566, filed on Apr. 5, 2022, which is incorporated herein by reference in its entirety.

BACKGROUND

Field of Invention

The present disclosure relates to apparatuses and method for locating an implant including magnetic material and/or a charge storage device in a living animal.

Discussion of the Background

Implants, such as sensors, may be implanted within a living animal (e.g., a human). An implant may, for example, detect the presence or amount of an analyte (e.g., glucose or oxygen) in a medium (e.g., blood or interstitial fluid) within the living animal. Some implants may be relatively small (e.g., 2-4 mm diameter capsule) and may be implanted in the subcutaneous tissue of a host. The implant may need to be located (e.g., for removal of the implant). Due to the small size of the implant, it may be difficult to locate and retrieve the implant from the subcutaneous tissue of the host.

SUMMARY

One aspect of the invention may provide an apparatus for locating an implant including magnetic material. The apparatus may include a magnetic field generator, a sensor, and a computer. The magnetic field generator may be configured to generate a magnetic field. The sensor may be configured to detect changes in the magnetic field and to generate a sensor signal indicative of the changes in the magnetic field. The magnetic material of the implant may cause changes to the magnetic field as the sensor is moved over the implant. The computer may be configured to use the sensor signal to detect a location of the implant.

In some aspects, the magnetic field generator may include a cylindrical magnet. In some aspects, the cylindrical magnet may be hollow.

In some aspects, the magnetic field generator may include one or more magnets. In some aspects, the magnetic field generator may include two or more magnets. In some aspects, the magnetic field generator may further include a housing configured to hold the two or more magnets. In some aspects, the magnetic field generator may include four magnets. In some aspects, the magnetic field generator may include six magnets. In some aspects, the one or more magnets may include one or more permanent magnets. In some aspects, the one or more magnets may include one or more electromagnets.

In some aspects, the magnetic field generated by the magnetic field generator may be a substantially uniform magnetic field.

In some aspects, the magnetic field may be substantially symmetric about a longitudinal axis at the center of the magnetic field generator. In some aspects, the magnetic field may be non-uniform and/or asymmetric about a longitudinal axis at the center of the magnetic field generator. In some aspects, the sensor may be located along or offset from the longitudinal axis at the center of the magnetic field generator.

In some aspects, the computer may be configured to, in detecting the location of the implant, determine edges of the magnetic material of the implant based on locations of bimodal peaks in the changes in the magnetic field during movement of the sensor along a longitudinal axis of the implant. In some aspects, the computer may be configured to determine edges of the implant based on the determined edges of the magnetic material of the implant and one of more offsets between edges of the implant and edges of the magnetic material of the implant. In some aspects, the computer may be configured to determine a depth of the implant based on a magnitude of the change in the magnetic field at the bimodal peaks in the changes in the magnetic field during the movement of the sensor along the longitudinal axis of the implant. In some aspects, the computer may be configured to determine an orientation of the implant based on a difference between magnitudes of the change in the magnetic field at the bimodal peaks in the changes in the magnetic field during the movement of the sensor along the longitudinal axis of the implant.

In some aspects, the computer may be configured to calculate a derivative of the changes in the magnetic field and to use the calculated derivative to detect the location of the implant. In some aspects, the derivative of the changes in the magnetic field may be with respect to time (during the movement of the sensor along the longitudinal axis of the implant). In some alternative aspects, the derivative of the changes in the magnetic field may be with respect to the position of the sensor (during movement of the sensor along the longitudinal axis of the implant). In some aspects, the computer may be configured to determine edges of the magnetic material of the implant based on locations where the derivative of the changes in the magnetic field equals zero during movement of the sensor along a longitudinal axis of the implant. In some aspects, the computer may be configured to determine a depth of the implant based on magnitudes of the changes in the magnetic field at the locations where the derivative of the changes in the magnetic field equals zero during the movement of the sensor along the longitudinal axis of the implant. In some aspects, the computer may be configured to determine an orientation of the implant based on a difference between magnitudes of the changes in the magnetic field at the locations where the derivative of the changes in the magnetic field equals zero during the movement of the sensor along the longitudinal axis of the implant. In some aspects, the computer may be configured to determine a midline of the implant based on a location where the derivative of the changes in the magnetic field equals zero during movement of the sensor across a longitudinal axis of the implant. In some aspects, the derivative of the changes in the magnetic field may be with respect to time or position (as the sensor is moved across the longitudinal axis of the implant).

In some aspects, the computer may be further configured to use the one or more sensor signals to detect an orientation of the implant.

In some aspects, the apparatus may further include a display, and the computer may be configured to cause the display to display an indication of the detected location of the implant. In some aspects, the display may be located above the sensor. In some aspects, the indication of the detected location of the implant may include an implant image, and a location of the implant image on a screen of the display relative to a point on the screen of the display may correspond to the detected location of the implant relative to the sensor. In some aspects, the implant image may have an orientation that corresponds to a detected orientation of the implant.

In some aspects, the apparatus may further include an incision marking tool configured to identify an incision location for removing the implant.

In some aspects, a diameter of the magnetic field generator may be equal to the length of the implant.

In some aspects, the apparatus may further include a position detector configured to generate a location signal indicative of a location of the sensor on the skin surface. In some aspects, the position detector may include a motion detector configured to detect movement of the sensor and to generate a motion signal indicative of the detected movement of the sensor, and the location signal may include the motion signal. In some aspects, the computer may be configured to use the sensor signal and the location signal to generate a map of sensor signals at different locations of the sensor on the skin surface.

Another aspect of the invention may provide a method for locating an implant including magnetic material. The method may include using a magnetic field generator to generate a magnetic field. The method may include using a sensor to detect changes in the magnetic field and to generate a sensor signal indicative of the changes in the magnetic field. The magnetic material of the implant may cause changes to the magnetic field as the sensor is moved over the implant. The method may include using a computer to detect a location of the implant based on the sensor signal.

In some aspects, detecting the location of the implant may include determining edges of the magnetic material of the implant based on locations of bimodal peaks in the changes in the magnetic field during movement of the sensor along a longitudinal axis of the implant.

Yet another aspect of the invention may provide a method for locating an implant including magnetic material. The method may include moving an apparatus including a magnetic field generator and a sensor across a longitudinal axis of the implant. The magnetic material of the implant may cause changes in a magnetic field generated by the magnetic field generator as the apparatus is moved across the longitudinal axis of the implant, and the sensor may detect changes in the magnetic field. The method may include determining a midline of the implant based on a location where the changes in the magnetic field are greatest as the apparatus is moved across the longitudinal axis of the implant. The method may include moving the apparatus along the determined midline of the implant. The method may include determining edges of the magnetic material of the implant based on locations of bimodal peaks in the changes in the magnetic field as the apparatus is moved along the determined midline of the implant.

In some aspects, the method may further include using an incision marking tool of the apparatus to mark an incision location for removing the implant.

Still another aspect of the invention may provide an apparatus for locating an implant including a charge storage device. The apparatus may include an electromagnetic field generator, a sensor, and a computer. The electromagnetic field generator may be configured to generate an electromagnetic field. The sensor may be configured to detect changes in the electromagnetic field and to generate a sensor signal indicative of the changes in the electromagnetic field. The charge storage device of the implant may cause changes to the electromagnetic field as the sensor is moved over the implant. The computer may be configured to use the sensor signal to detect a location of the implant.

Yet another aspect of the invention may provide a method for locating an implant including a charge storage device. The method may include using an electromagnetic field generator to generate an electromagnetic field. The method may include using a sensor to detect changes in the electromagnetic field and to generate a sensor signal indicative of the changes in the electromagnetic field. The charge storage device of the implant may cause changes to the electromagnetic field as the sensor is moved over the implant. The method may include using a computer to detect a location of the implant based on the sensor signal.

Still another aspect of the invention may provide a method for locating an implant including a charge storage device. The method may include moving an apparatus including an electromagnetic field generator and a sensor across a longitudinal axis of the implant. The charge storage device of the implant may cause changes in an electromagnetic field generated by the electromagnetic field generator as the apparatus is moved across the longitudinal axis of the implant, and the sensor may detect changes in the electromagnetic field. The method may include determining a midline of the implant based on a location where the changes in the electromagnetic field are greatest as the apparatus is moved across the longitudinal axis of the implant. The method may include moving the apparatus along the determined midline of the implant. The method may include determining edges of the charge storage device of the implant based on locations of bimodal peaks in the changes in the electromagnetic field as the apparatus is moved along the determined midline of the implant.

These and other embodiments encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

Figure 1:
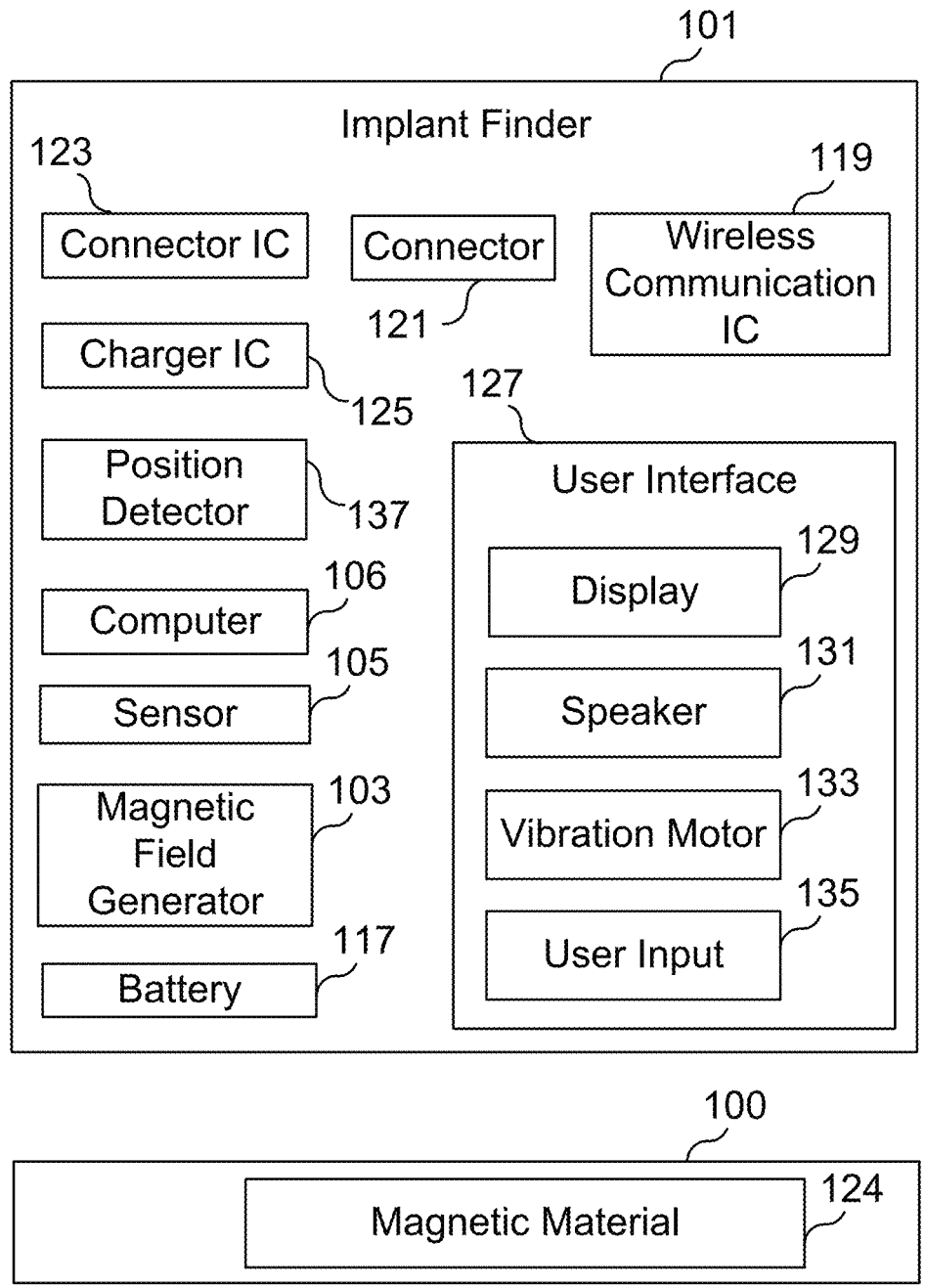
FIG. 1 is a block diagram illustrating a non-limiting example of an implant and an implant finder embodying aspects of the present invention.

FIG. 1 is a block diagram illustrating an implant 100 and an implant finder 101 embodying aspects of the present invention. In some aspects, the implant finder 101 may be for locating the implant 100, which may have been implanted in tissue below the surface of skin of a living animal. In some aspects, as shown in FIG. 1, the implant 100 may include magnetic material 124 (e.g., a magnetic core). In some aspects, the magnetic material 124 may include, for example and without limitation, a ferromagnetic material (e.g., iron) or a ferrimagnetic material (e.g., ferrite).

In some aspects, the implant finder 101 may include a magnetic field generator 103, a sensor 105, a computer 106, a battery 117, a wireless communication integrated circuit (IC) 119, a connector 121, a connector IC 123, a charger IC 125, a user interface 127, and/or a position detector 137. In some aspects, the user interface 127 of the implant finder 101 may include a display 129 (e.g., an optical display such as, for example, a light emitting diode (LED) display), a speaker 131, a vibration motor 133, and/or a user input 135.

In some aspects, the magnetic field generator 103 may be configured to generate a magnetic field. In some aspects, the sensor 105 may be configured to detect changes in the magnetic field and to generate a sensor signal indicative of the changes in the magnetic field. In some aspects, the magnetic material 124 of the implant 100 may cause changes to the magnetic field as the sensor 105 is moved over the implant 100. In some aspects, the computer 106 may be configured to use the sensor signal to detect a location of the implant 100.

In some aspects, as shown in FIGS. 2A, 2B, 2E, and 3A, the magnetic field generator 103 may include one or more magnets 109. In some aspects, the one or more magnets 109 may be, for example and without limitation, permanent magnets and/or electromagnets (e.g., a coil of wire wound around a magnetic core made from a ferromagnetic or ferrimagnetic material). In some aspects, as shown in the FIGS. 5A-5C, the magnetic field generator 103 may include a housing 107, and the housing 107 may be configured to hold the one or more magnets 109. However, a housing 107 is not required, and, in some alternative aspects (e.g., some aspects in which the magnetic field generator 103 consists of only a single magnet 109), the magnetic field generator 103 does not include a housing 107.

Figure 2A:
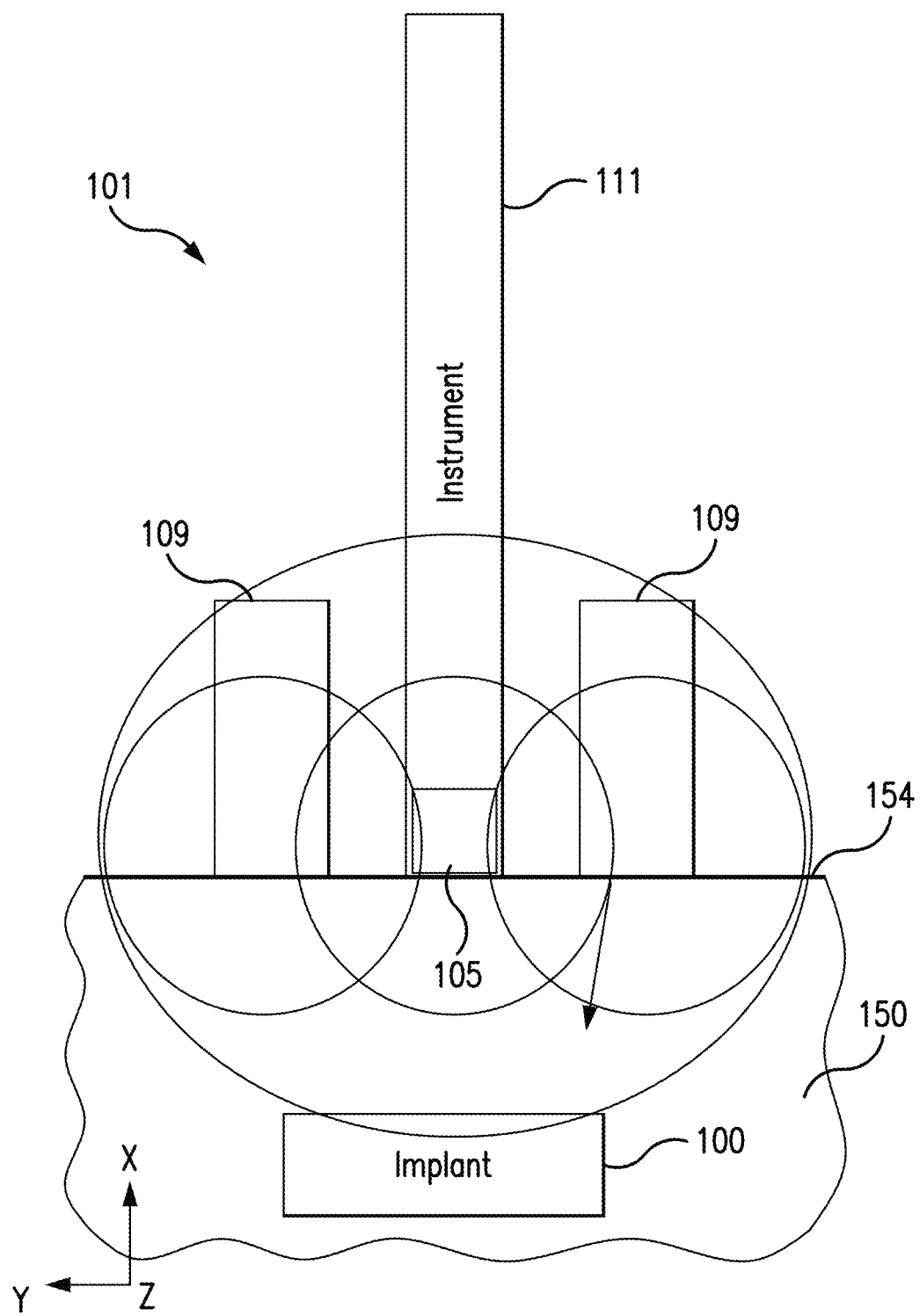
FIG. 2A is a cross-sectional side view illustrating a non-limiting example of an implant and an implant finder embodying aspects of the present invention.
Figure 2B:
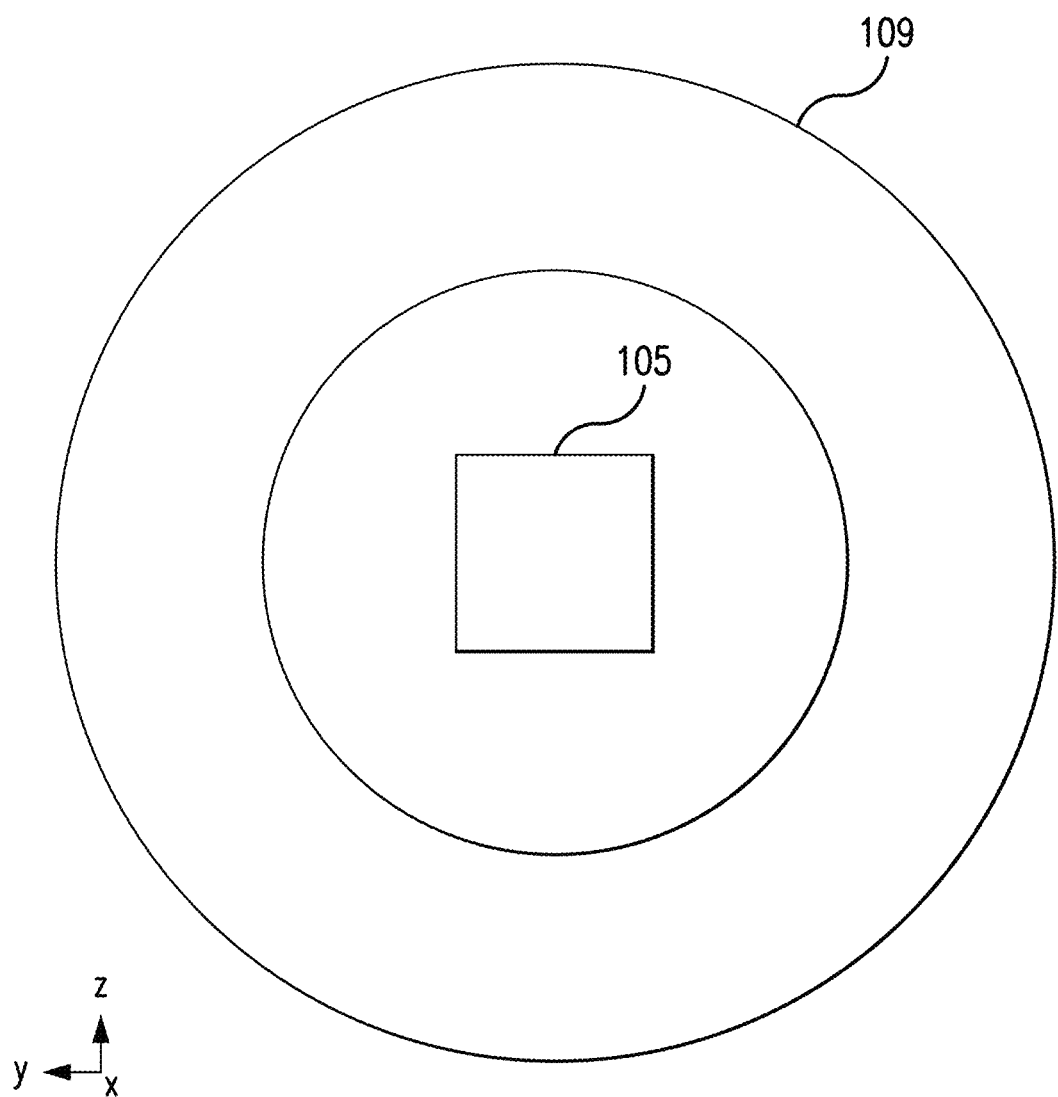
FIG. 2B is a cross-sectional top view illustrating a non-limiting example of an implant finder embodying aspects of the present invention.
Figures 2C, 2D:
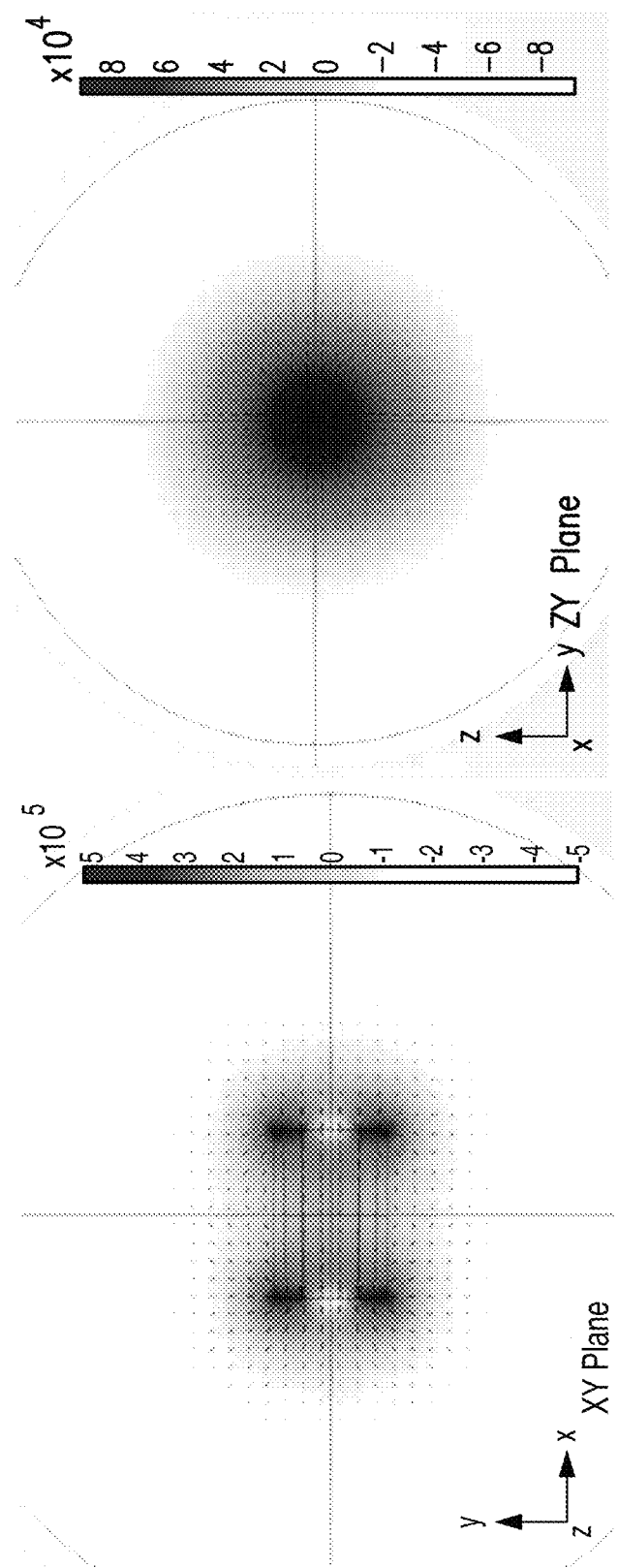
FIGS. 2C and 2D are two-dimensional contour plot slices in the XY and ZY planes, respectively, illustrating the magnitude of a magnetic field generated by a non-limiting example of a hollow, cylindrical magnetic field generator embodying aspects of the present invention.
Figure 2E:
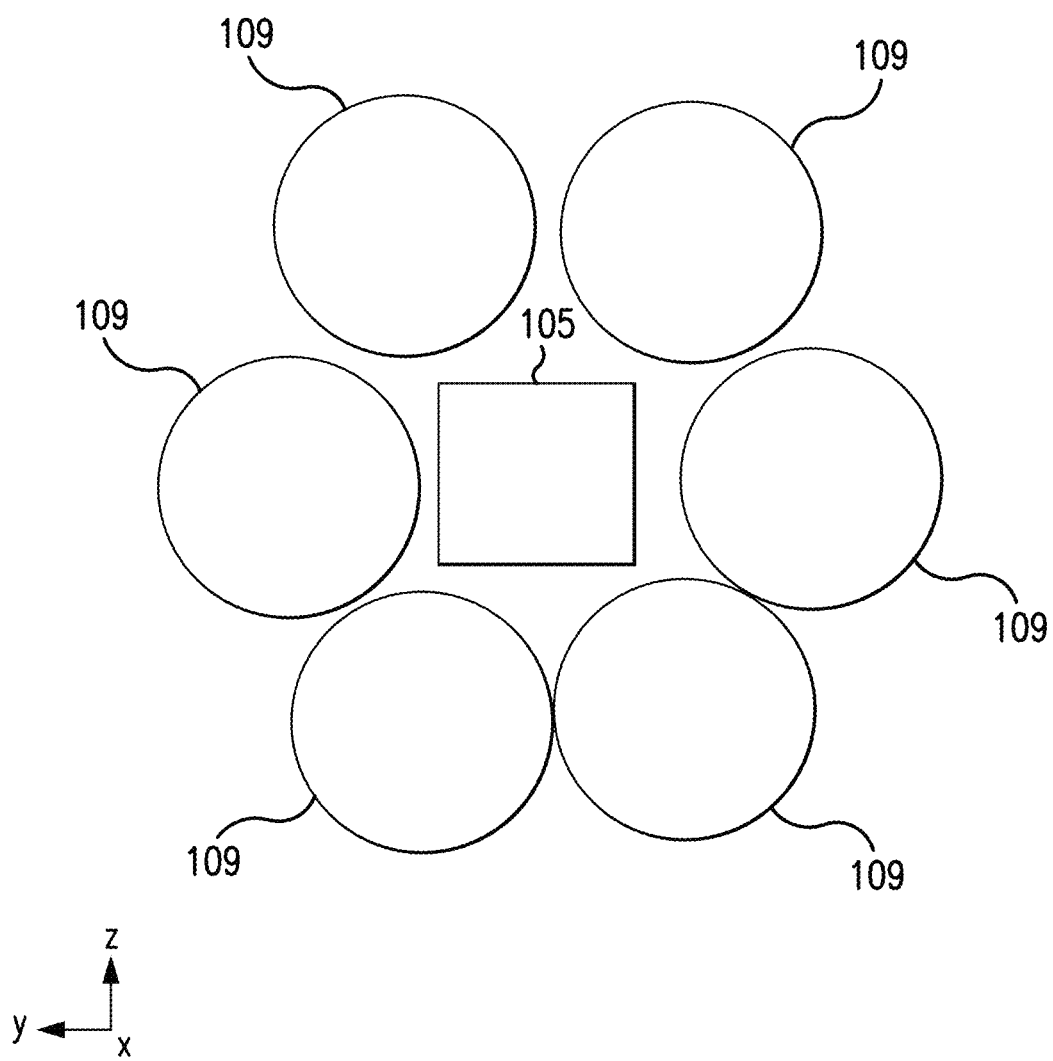
FIG. 2E is a cross-sectional top view illustrating a non-limiting example of an implant finder embodying aspects of the present invention.
Figures 2F, 2G:
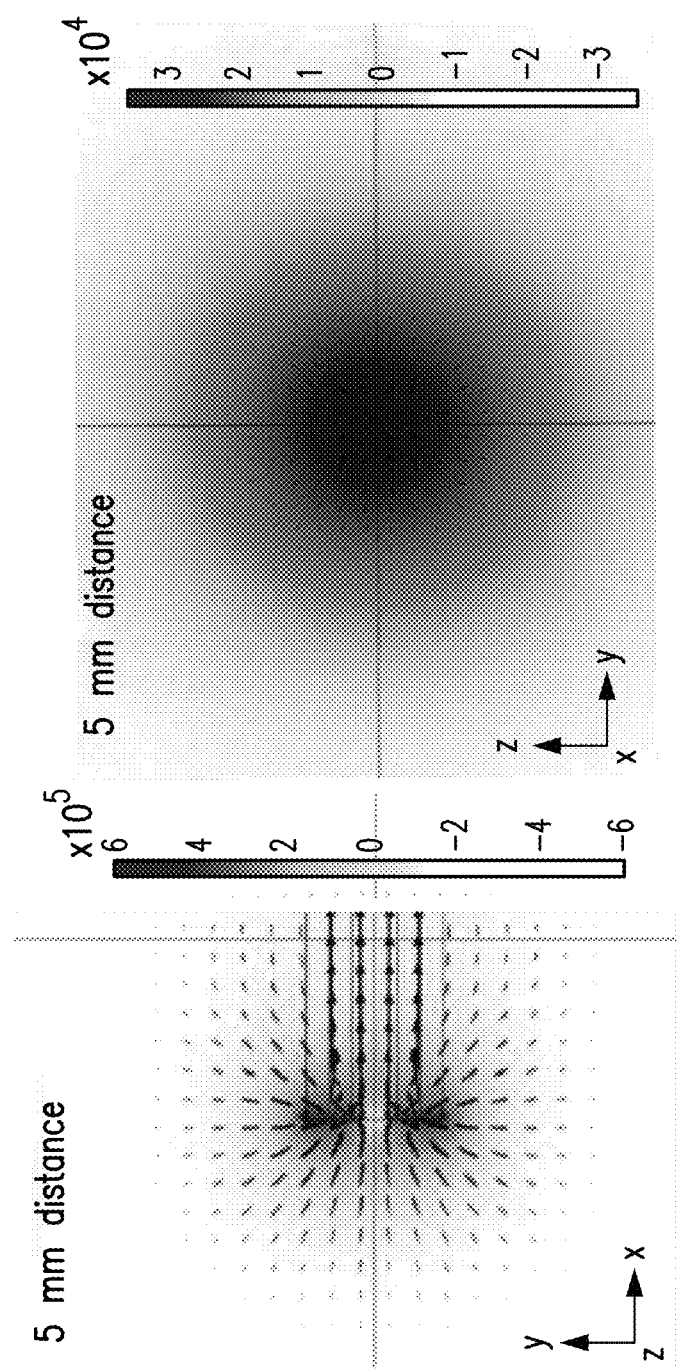
FIGS. 2F and 2G are two-dimensional contour plot slices in the XY and ZY planes, respectively, illustrating the magnitude and vector of a magnetic field generated by a non-limiting example of a magnetic field generator including six magnets embodying aspects of the present invention.
Figures 2H, 2I:
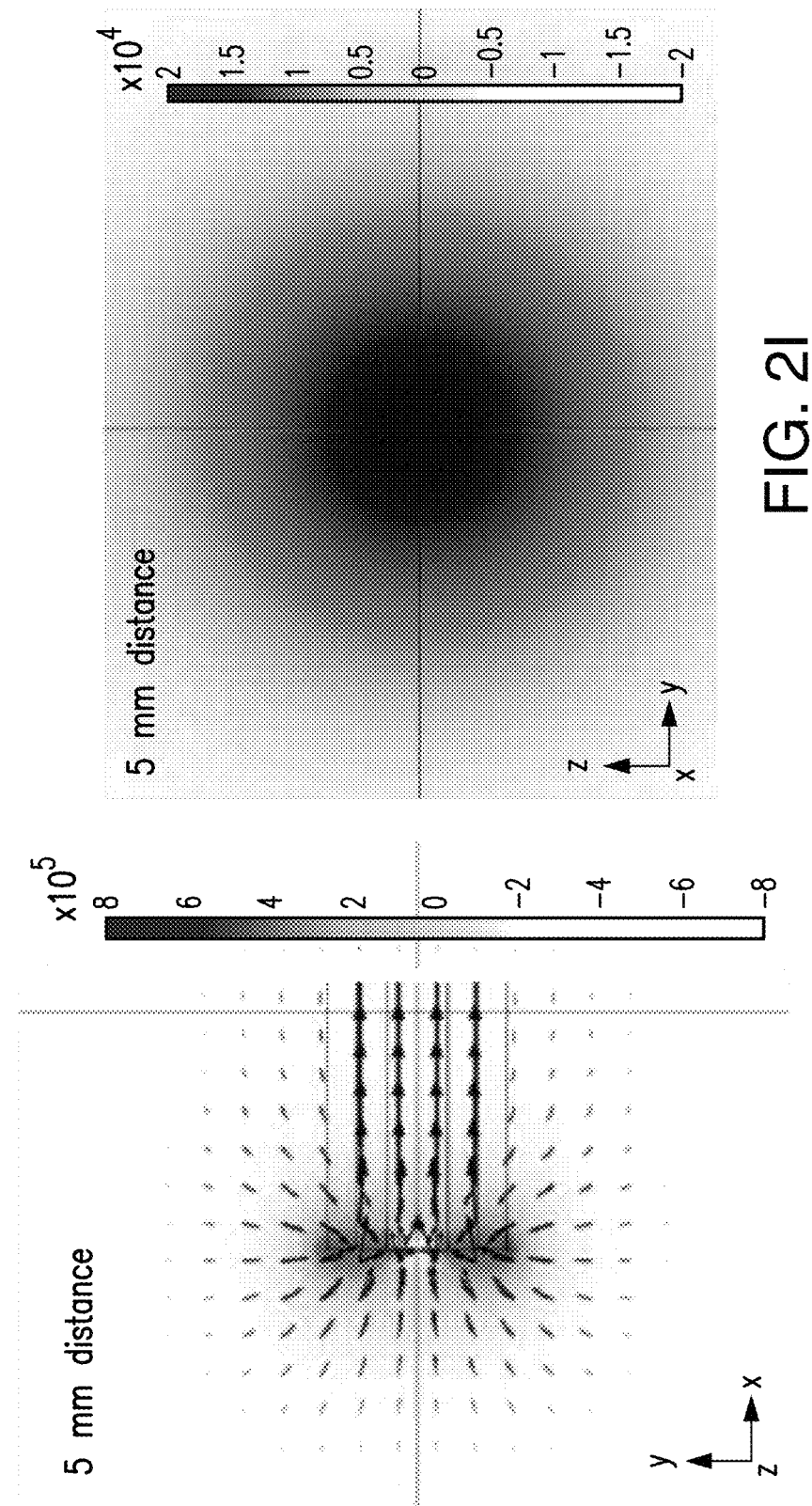
FIGS. 2H and 2I are two-dimensional contour plot slices in the XY and ZY planes, respectively, illustrating the magnitude and vector of a magnetic field generated by a non-limiting example of a magnetic field generator including four magnets embodying aspects of the present invention.
Figure 3A:
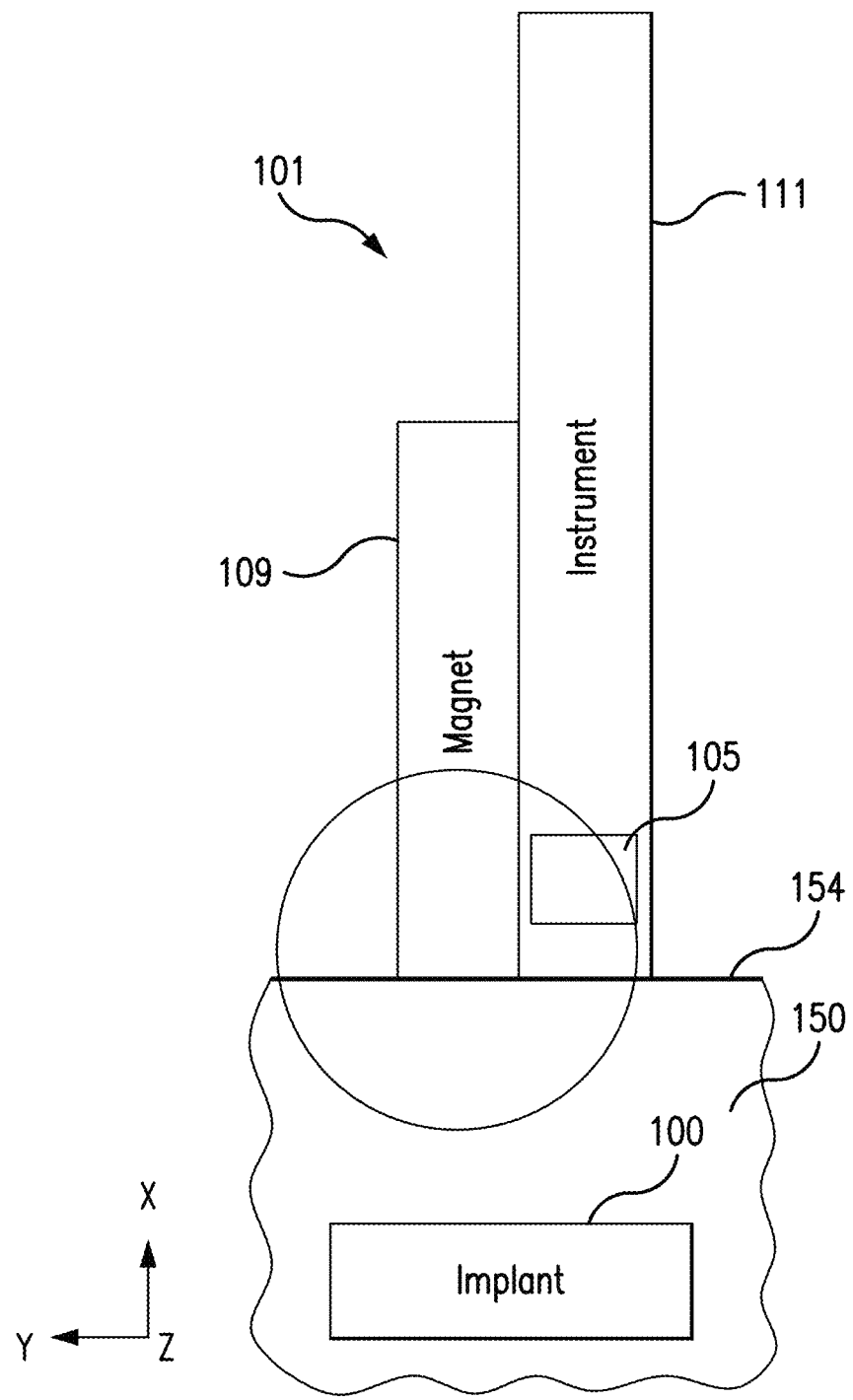
FIG. 3A is a cross-sectional side-view illustrating a non-limiting example of an implant and an implant finder embodying aspects of the present invention.
Figure 3C:
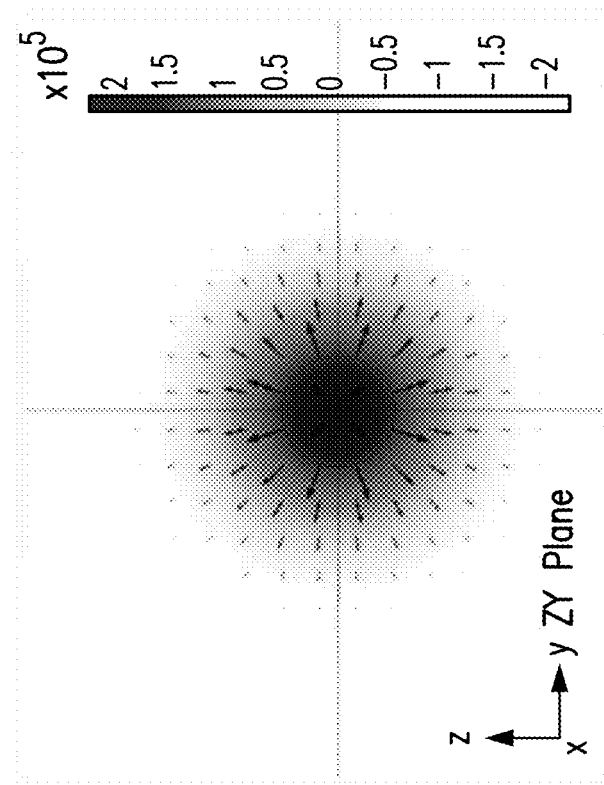
FIGS. 3B and 3C are two-dimensional contour plot slices in the XY and ZY planes, respectively, illustrating the magnitude and vector of a magnetic field generated by a non-limiting example of a cylindrical magnetic field generator embodying aspects of the present invention.
Figure 3B:
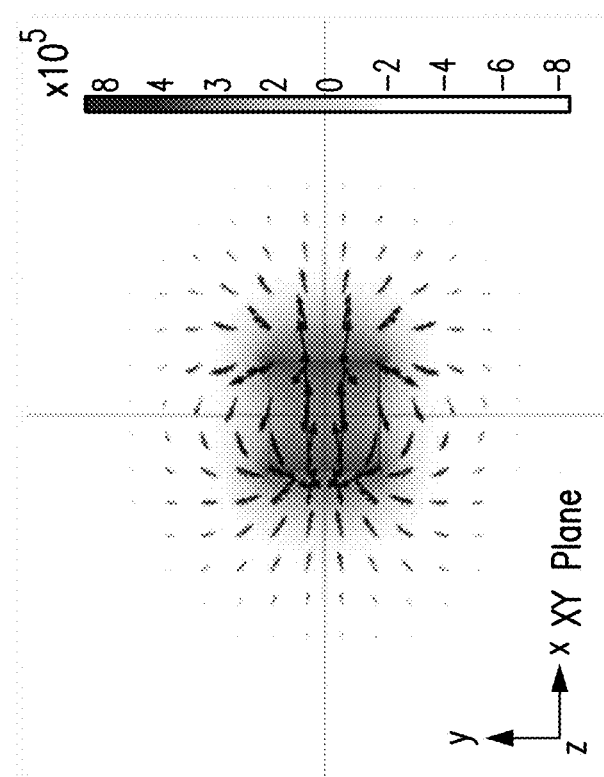

In some aspects, as shown in FIGS. 2A, 2B, and 2E, the sensor 105 may be located on a longitudinal axis at the center of the magnetic field generator 103. However, this is not required, and, in some alternative aspects, the sensor 105 is not located on a longitudinal axis at the center of the magnetic field generator 103. For example, as shown in FIG. 3A, the sensor 105 may be located adjacent to the magnet 109 of the magnetic field generator 103 (as opposed to at the center of one or more magnets 109 of the magnetic field generator 103).

In some aspects, as shown in FIG. 2B, the magnetic field generator 103 may include a hollow cylindrical magnet 109. In some alternative aspects, as shown in FIG. 2E, the magnetic field generator 103 may include two or more magnetics 109 (e.g., four or six magnets). In some other alternative aspects, as shown in FIG. 3A, the magnetic field generator 103 may include a solid cylindrical magnet 109.

In some aspects, the one or more magnets 109 of the magnetic field generator 103 may generate a substantially uniform magnetic field. In some aspects, the hollow cylindrical magnet 109 of the magnetic field generator 103 illustrated in FIG. 2B may generate a magnetic field having the magnitudes shown in the two-dimensional contour plot slices of FIGS. 2C and 2D. In some aspects, the six magnets 109 of the magnetic field generator 103 illustrated in FIG. 2E may generate a magnetic field having the magnitudes shown in the two-dimensional contour plot slices of FIGS. 2F and 2G. In some aspects, the magnetic field generator 103 may include four magnets 109, and the four magnets 109 may generate a magnetic field having the magnitudes shown in the two-dimensional contour plot slices of FIGS. 2H and 2I. In some aspects, the solid cylindrical magnet 109 of the magnetic field generator 103 illustrated in FIG. 3A may generate a magnetic field having the magnitudes shown in the two-dimensional contour plot slices of FIGS. 3B and 3C. In some aspects, as shown in FIGS. 2C, 2D, 2F-2I, 3B, and 3C, the magnetic field generated by the one or more magnetics 109 of the magnetic field generator 103 may be substantially symmetric about a longitudinal axis at the center of the magnetic field generator 103. However, this is not required, and in some alternative aspects, the magnetic field may have a different profile (e.g., the magnetic field may be non-uniform and/or asymmetric about the longitudinal axis at the center of the magnetic field generator). In some aspects, as shown in FIGS. 2A, 2B, and 2E, the sensor 105 may be located on the longitudinal axis at the center of the magnetic field generator 103.

Figure 4A:
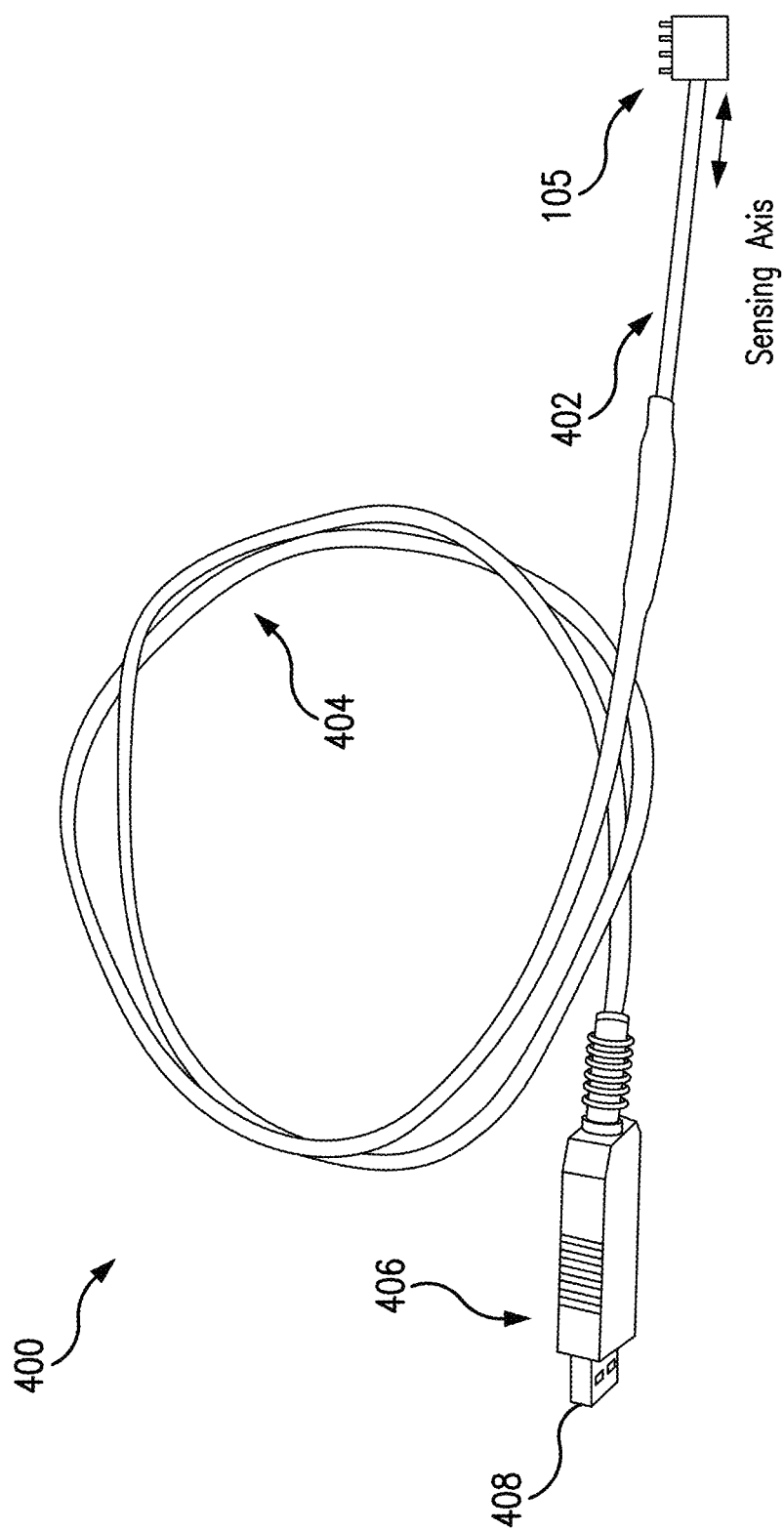
FIGS. 4A and 4B illustrate a non-limiting example of a magnetometer including the sensor of an implant finder embodying aspects of the present invention.
Figure 4B:
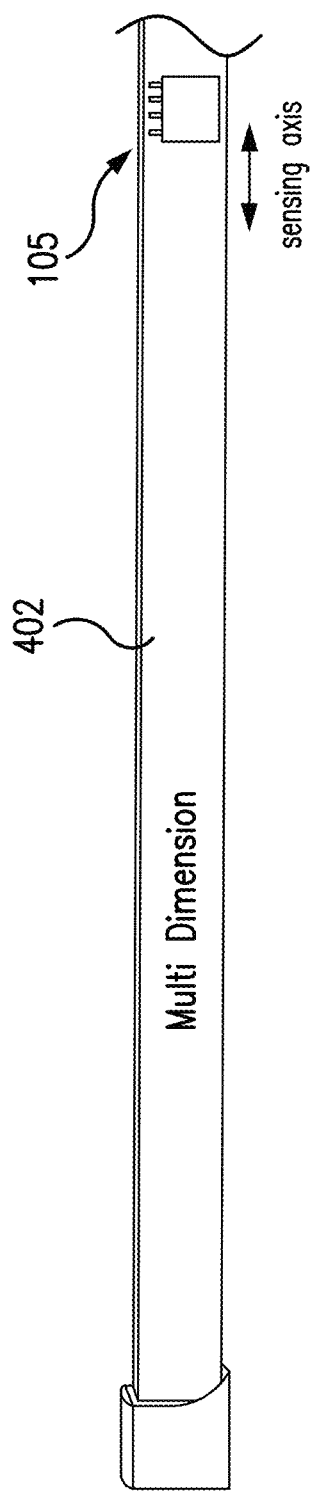

In some aspects, the sensor 105 may be a magnetic field sensor. In some aspects, the sensor 105 may be a tunnel magnetoresistance (TMR) magnetic field sensor (e.g., a TMR full bridge magnetic field sensor) or a Hall sensor (e.g., a high field Hall sensor). In some aspects, as shown in FIGS. 4A and 4B, the sensor 105 may be part of a magnetometer 400 (e.g., an axial low-field magnetometer). In some aspects, the magnetometer 400 may include the sensor 105, a probe 402 (e.g., a rigid probe), a cable 404 (e.g., a flexible cable), and data acquisition electronics 406, and/or a connector 408 (e.g., a USB connector). In some aspects, the connector 408 of the magnetometer 400 may be connected to the computer 106 of the implant finder 101.

Figure 5A:
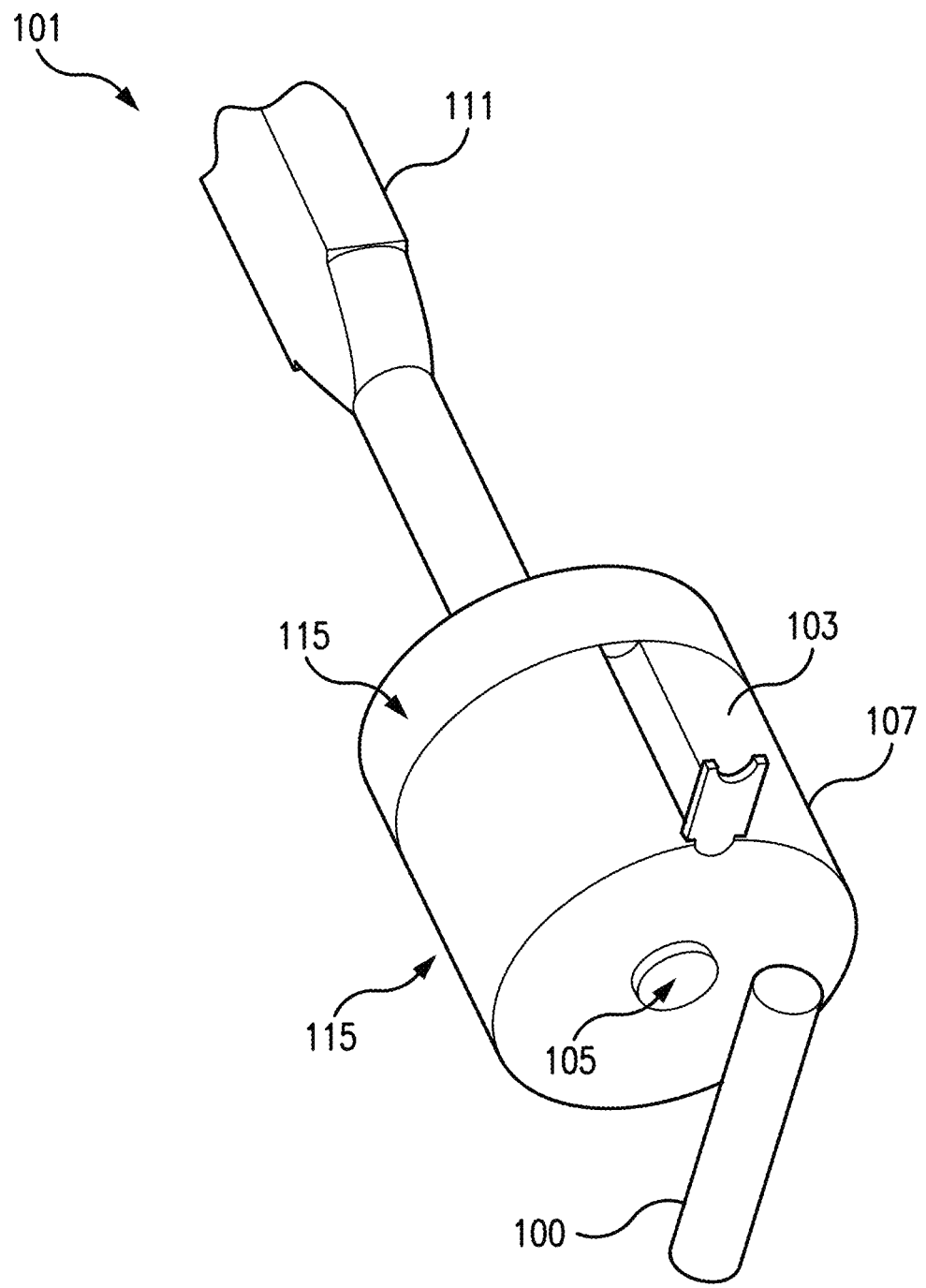
FIGS. 5A and 5B are perspective views illustrating a non-limiting example of an implant and an implant finder embodying aspects of the present invention.
Figure 5B:
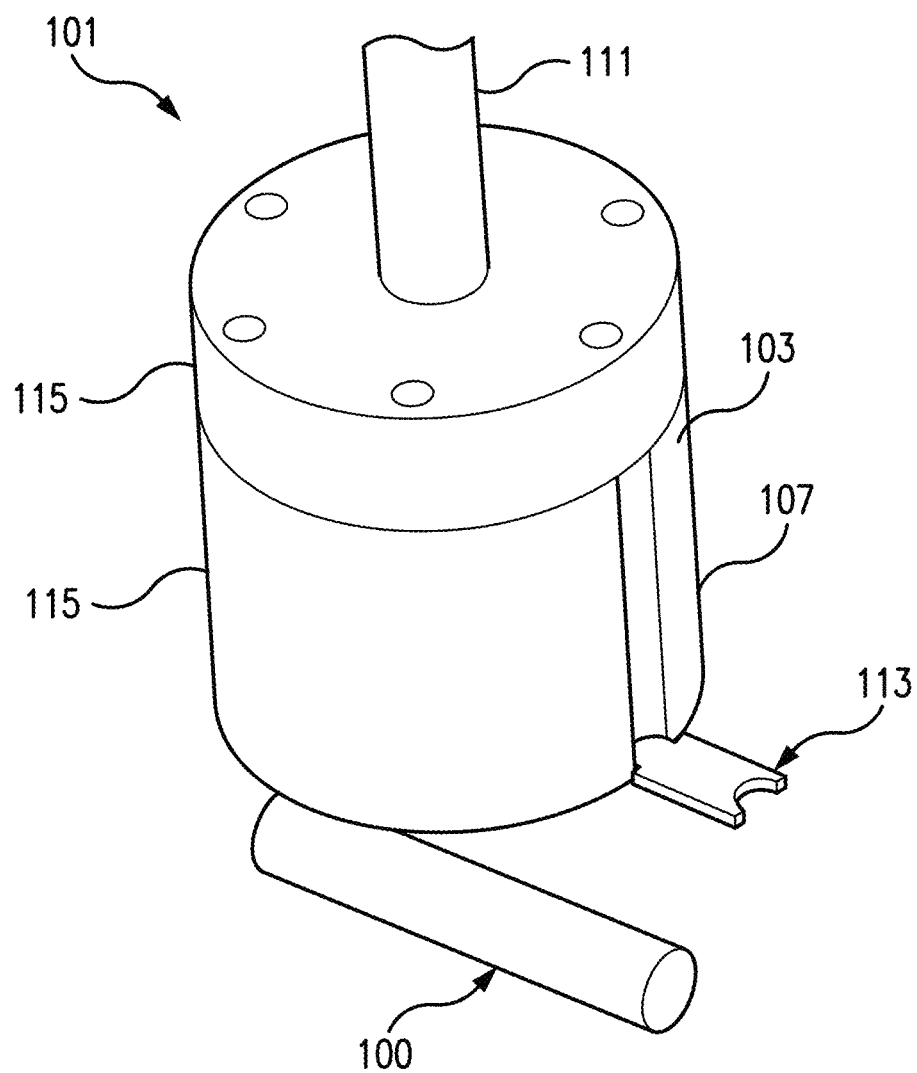
Figure 5C:
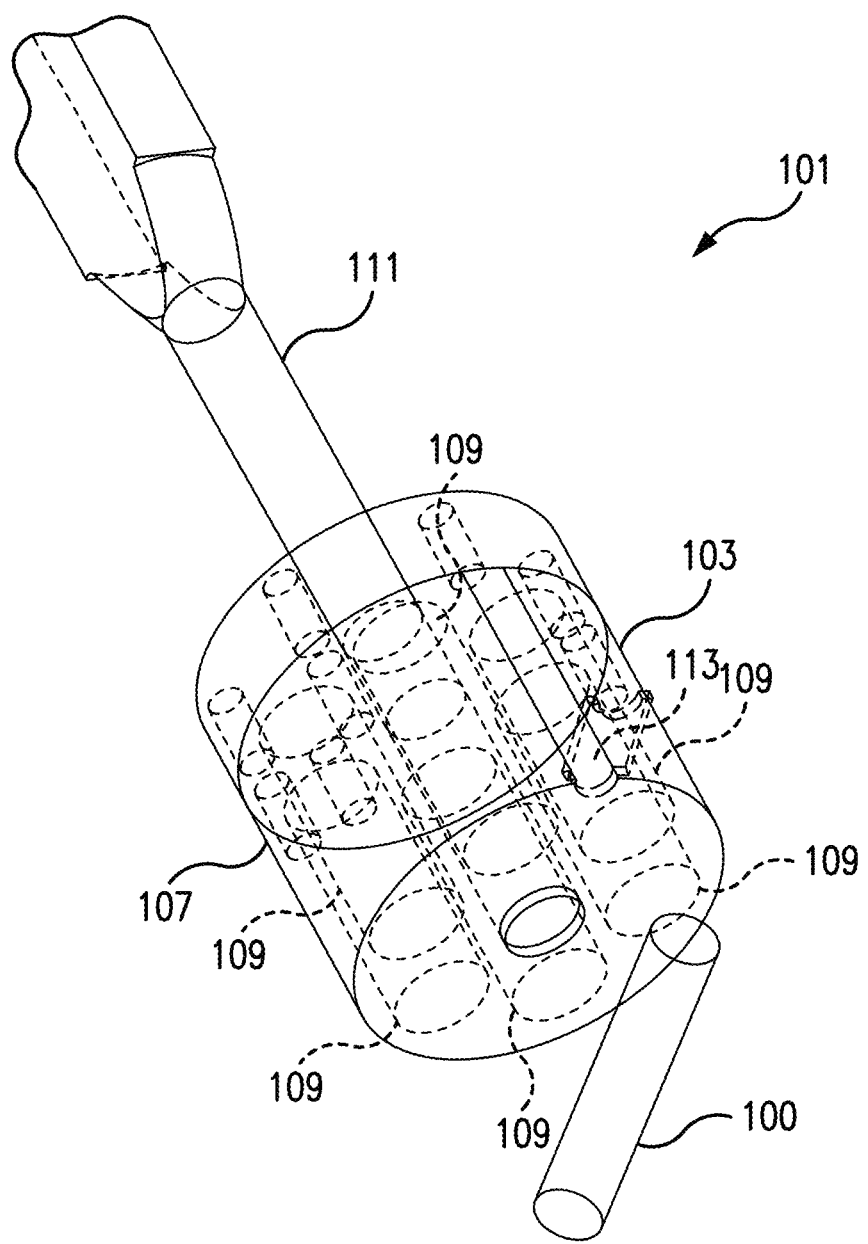
FIG. 5C is a see-through perspective view illustrating a non-limiting example of an implant and an implant finder embodying aspects of the present invention.
Figure 5D:
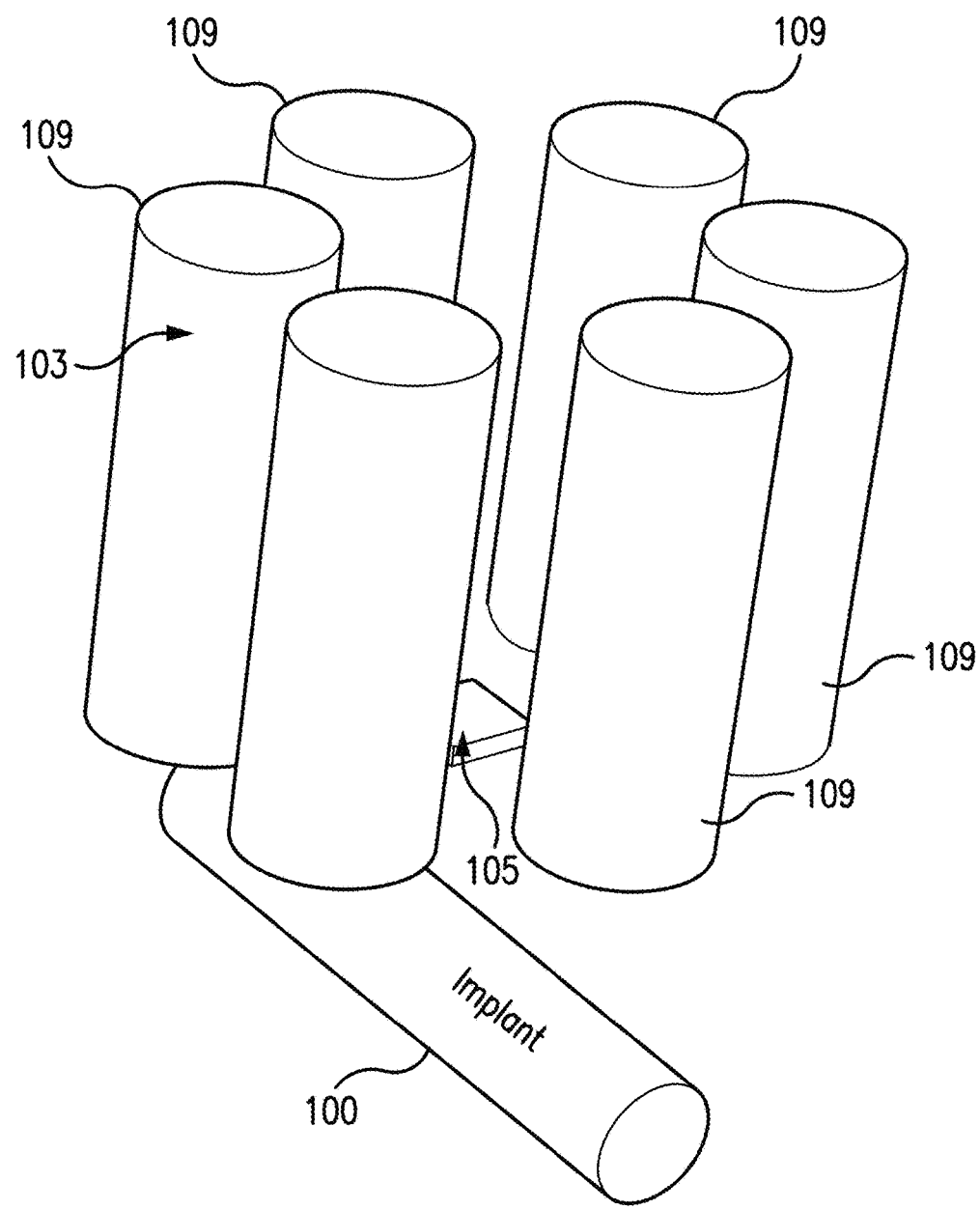
FIGS. 5D and 5E are perspective and top views illustrating a non-limiting example of an implant and magnetic field generator and sensor of an implant finder embodying aspects of the present invention.
Figure 5E:
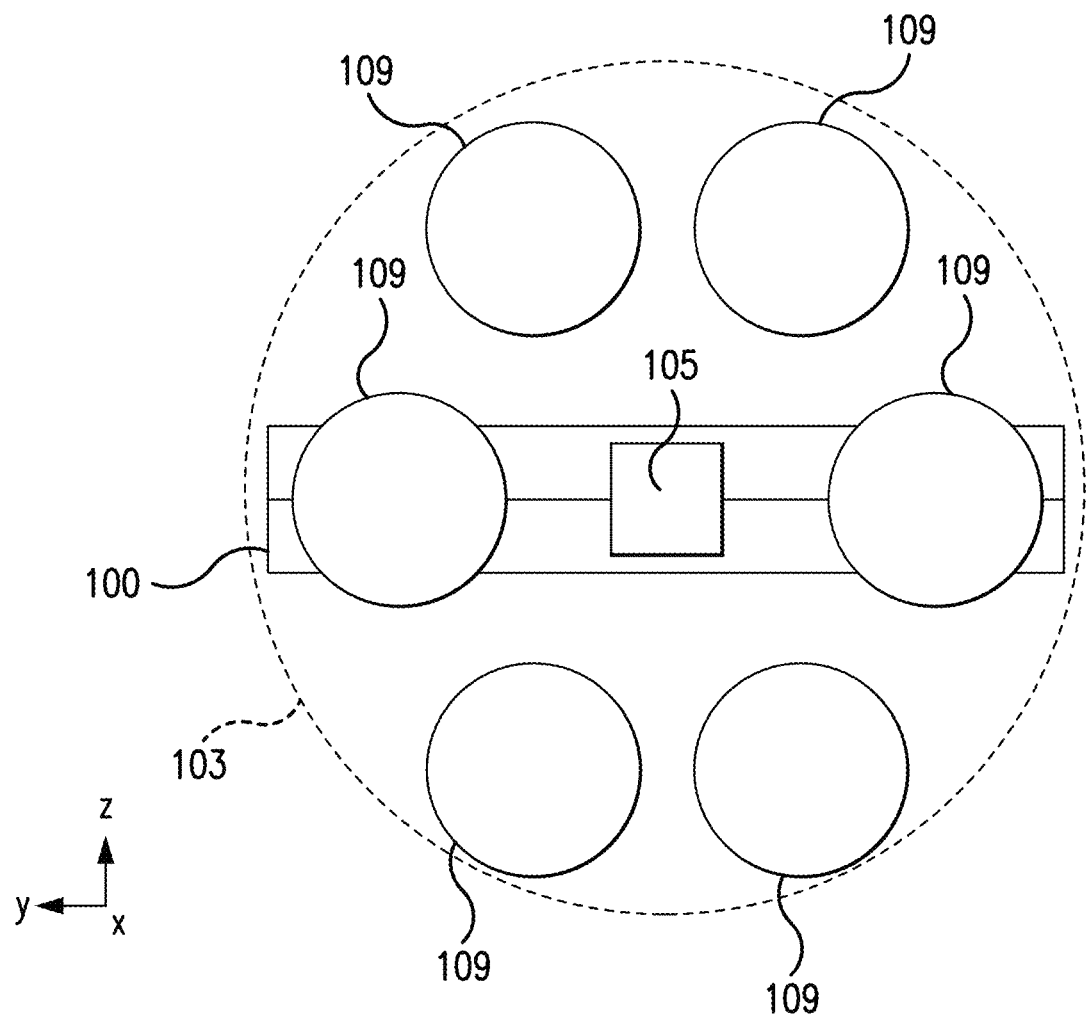
Figure 5F:
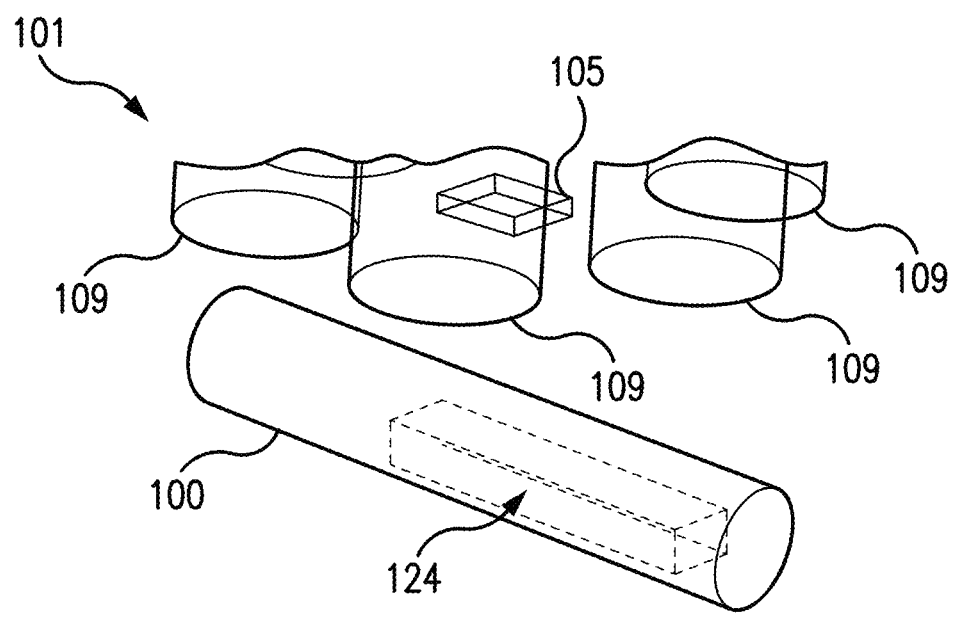
FIG. 5F is a see-through perspective view illustrating a non-limiting example of an implant and magnetic field generator and sensor of an implant finder embodying aspects of the present invention.

In some aspects, as shown in FIGS. 5A-5F, the implant finder 101 may include the magnetic field generator 103 and the sensor 105. In some aspects, the sensor 105 may be located on the longitudinal axis at the center of the magnetic field generator 103. In some aspects, the magnetic field generator 103 may include a housing 107. In some aspects, the housing 107 may include housing bodies 115 (e.g., polymer bodies). In some aspects, as shown in FIGS. 5C-5F, the magnetic field generator 103 may include one or more magnets 109. In some aspects, the housing 107 may be configured to house the one or more magnets 109. In some aspects, as shown in FIGS. 5C-5F, the magnetic field generator 103 may include six magnets 109. However, in some alternative aspects, the magnetic field generator 103 may include a different number of magnets 109 (e.g., ten, nine, eight, seven, five, four, three, or two magnets or a single magnet, such as a hollow cylindrical magnet). In some aspects, as shown in FIG. 5E, a diameter or width of the magnetic field generator 103 may be equal to the length of the implant 100. However, this is not required, and, in some alternative aspects, the magnetic field generator 103 may have a different size (e.g., a diameter or width that is less than or greater than the length of the implant 100).

In some aspects, as shown in FIGS. 5A-5C, the implant finder 101 may include a handle 111. In some aspects, as shown in FIGS. 5A-5C, the implant finder 101 may include an incision marking tool 113. In some aspects, the incision marking tool 113 may be configured such that a user may use the incision marking tool 113 to mark an appropriate location on the skin surface 154 for an incision that would enable removal of the implant 100. In some aspects, the user may use to the incision marking tool 113 to mark the incision location when the implant finder 101 is located over the implant 100. In some aspects, the incision marking tool 113 may be configured to mark the skin surface 154 above a determined edge of the implant 100, a determined center of the implant 100, a determined edge of the magnetic material 124, or a determined center of the magnetic material 124. In some alternative aspects, the incision marking tool 113 may be configured to mark the skin surface 154 above a location offset from a determined edge of the implant 100, a determined center of the implant 100, a determined edge of the magnetic material 124, and/or a determined center of the magnetic material 124. In some alternative aspects, the incision marking tool 113 may be configured mark the skin surface at a longitudinal axis at the center of the magnetic field generator 103.

In some aspects in which the implant finder 101 includes the connector 121, the connector 121 may be, for example and without limitation, a Micro-Universal Serial Bus (USB) connector. In some aspects, the connector 121 may be configured to enable a wired connection to an external device, such as a personal computer or display device. In some aspects, the implant finder 101 may exchange data to and from the external device through the connector 121 and/or may receive power through the connector 121. In some embodiments, the connector IC 123 may be, for example and without limitation, a USB-IC, which may control transmission and receipt of data through the connector 121.

In some aspects in which the implant finder 101 includes the battery 117, the battery 117 may provide operating power for the implant finder 101. In some aspects, the battery 117 may be a rechargeable battery. In some aspects, the battery 117 may be, for example and without limitation, a lithium-polymer battery. In some aspects, the battery 117 may have a short recharge duration and/or may have a small size. In some aspects in which the display device 105 includes the charger IC 125, the charger IC 125 may receive power via the connector 121 and charge the battery 117.

In some aspects in which the implant finder 101 includes the wireless communication IC 119, the wireless communication IC 119 may enable wireless communication with one or more external devices, such as, for example, one or more personal computers and/or one or more other display devices (e.g., a smartphone or tablet executing an application). In some aspects, the wireless communication IC 119 may employ one or more wireless communication standards to wirelessly transmit data. The wireless communication standard employed may be any suitable wireless communication standard, such as an IEEE 802.11 standard, an ANT standard, a Bluetooth standard, or a Bluetooth Low Energy (BLE) standard (e.g., BLE 4.0). In some aspects, the wireless communication IC 119 may include an antenna (e.g., a Bluetooth antenna, a Wi-Fi antenna, and/or one or more cellular antennas). In some aspects, the antenna of the wireless communication IC 119 may be entirely contained within a housing (e.g., housing 107) of the implant finder 101. However, this is not required, and, in alternative embodiments, all or a portion of the antenna of the wireless communication IC 119 may be external to a housing of the implant finder 101.

In some aspects in which the implant finder 101 includes the position detector 137, the position detector 137 may be configured to generate a location signal indicative of a location of the sensor on the skin surface 154. In some aspects, the position detector 137 may, for example and without limitation, include a motion detector configured to detect movement of the sensor 105 (and/or implant finder 101) relative to the skin surface 154 and to generate a motion signal indicative of the detected movement of the sensor 105, and the location signal may include the motion signal. In some aspects, the motion detector may include a mechanical motion detector (e.g., that makes use of a motion of a ball inside the mechanical motion detector) and/or an optical motion detector (e.g., that uses light to detect movement of the sensor 105).

In some aspects in which the implant finder 101 includes the user interface 127, the user interface 127 may include one or more of a display 129 and a user input 135. In some aspects, the display 129 may include a liquid crystal display (LCD) and/or a light emitting diode (LED) display. In some aspects, the user input 135 may include one or more buttons, a keyboard, a keypad, and/or a touchscreen. In some aspects, the user interface 127 may include one or more of a speaker 131 (e.g., a beeper) and a vibration motor 133, which may be activated, for example, in the event that a condition is met (e.g., detection of an edge of the implant 100 and/or a detection of a midline of the implant 100).

In some aspects in which the implant finder 101 includes the computer 106, the computer 106 may control the overall operation of the implant finder 101. For example, the implant finder 101 may control the wireless communication IC 119, the connector IC 123, the charger IC 125, the position detector 137, the magnetic field generator 103, the sensor 105, and/or the user interface 127. In some aspects, the computer 106 may receive and/or process data from the sensor 105, the position detector 137, and/or user input 135 of the user interface 127. For example, in some aspects, the computer 106 may be configured to use the sensor signal generated by the sensor 105 to detect a location of the implant 100. In some aspects, the computer 106 may be configured to use the sensor signal generated by the sensor 105 and the location signal generated by the position detector 137 to generate a map of sensor signals at different locations of the sensor 105 on the skin surface 154. In some aspects, the computer 106 may additionally or alternatively control the display 129, speaker 131, and/or vibration motor 135 to provide information about the detected location of the implant 100. For example, in some aspects, the computer 106 may cause the display 129 to display a notification (e.g., one or more optical displays produced by one or more LEDs), the speaker 131 to beep, and/or the vibration motor 135 to vibrate when the computer 106 detects an edge of the implant 100 and/or a midline of the implant 100. In some aspects, the computer 106 may additionally or alternatively be configured to cause the display 129 to display an indication of the detected location of the implant 100.

Figure 6:
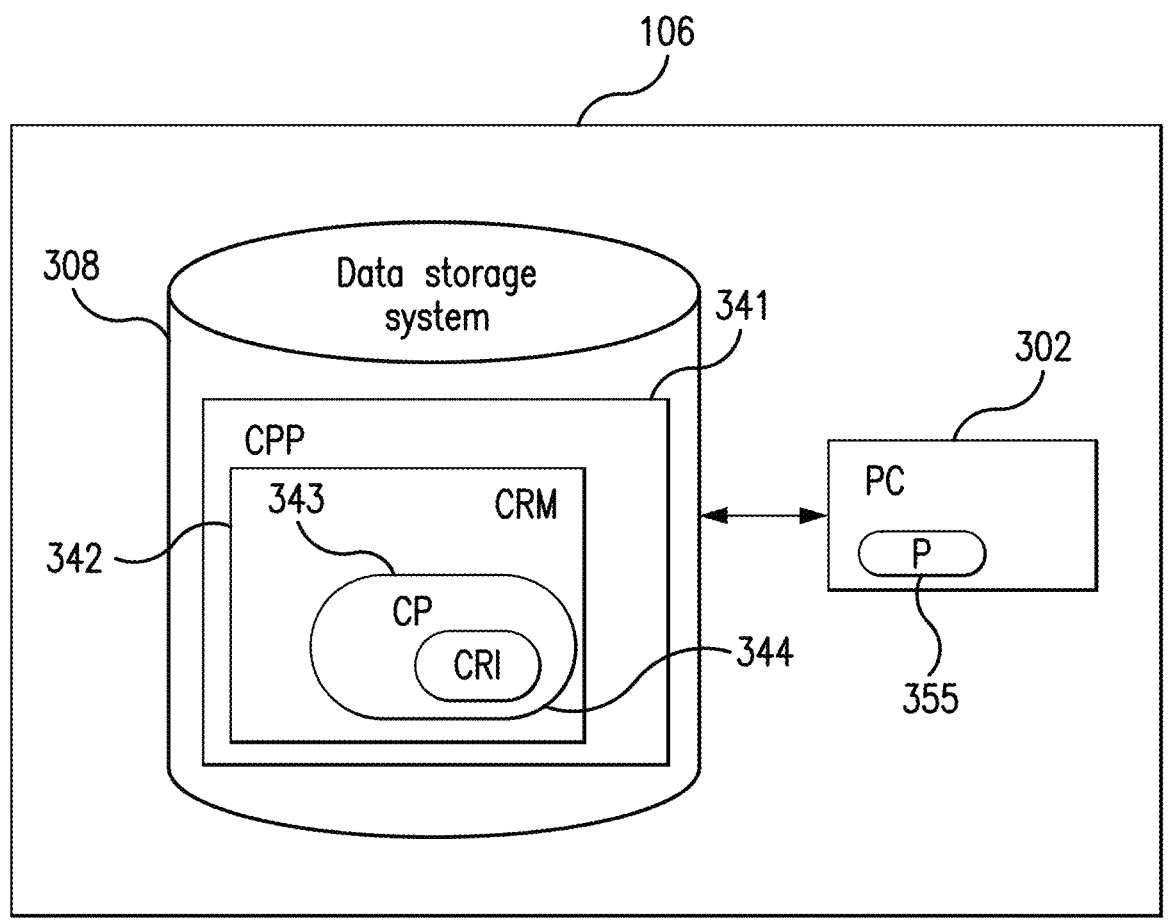
FIG. 6 is a block diagram illustrating a non-limiting example of a computer of an implant finder embodying aspects of the present invention.

FIG. 6 is a block diagram of the computer 106 of the implant finder 101 according to some aspects. In some aspects, the computer 106 can be adapted to perform any of methods, processes, or steps disclosed herein. As shown in FIG. 6, the computer 106 may include processing circuitry (PC) 302, which may include one or more processors (P) 355 (e.g., one or more general purpose microprocessors and/or one or more other processors, such as an application specific integrated circuit (ASIC), field-programmable gate arrays (FPGAs), and the like).

In some aspects, as shown in FIG. 6, the computer 106 may include one or more storage units (a.k.a., "data storage systems") 308 which may be co-located or geographically distributed and which may include one or more non-volatile storage devices and/or one or more volatile storage devices. In some aspects where the PC 302 includes a programmable processor, the one or more storage units may include a computer program product (CPP) 341. In some aspects, the CPP 341 may include a computer readable medium (CRM)

342 storing a computer program (CP) 343 comprising computer readable instructions (CRI) 344. In some aspects, the CRM 342 may be a non-transitory computer readable medium, such as, magnetic media (e.g., a hard disk), optical media, memory devices (e.g., random access memory, flash memory), and the like. In some aspects, the CRI 344 of the computer program 343 is adapted such that when executed by the PC 302, the CRI 341 may cause the computer 106 to perform steps described herein (e.g., steps described herein with reference to the flow charts). In other aspects, the computer 106 may be adapted to perform steps described herein without the need for code. That is, for example, the PC 302 may consist merely of one or more ASICs. Hence, the features of the aspects described herein may be implemented in hardware and/or software.

Figure 7A:
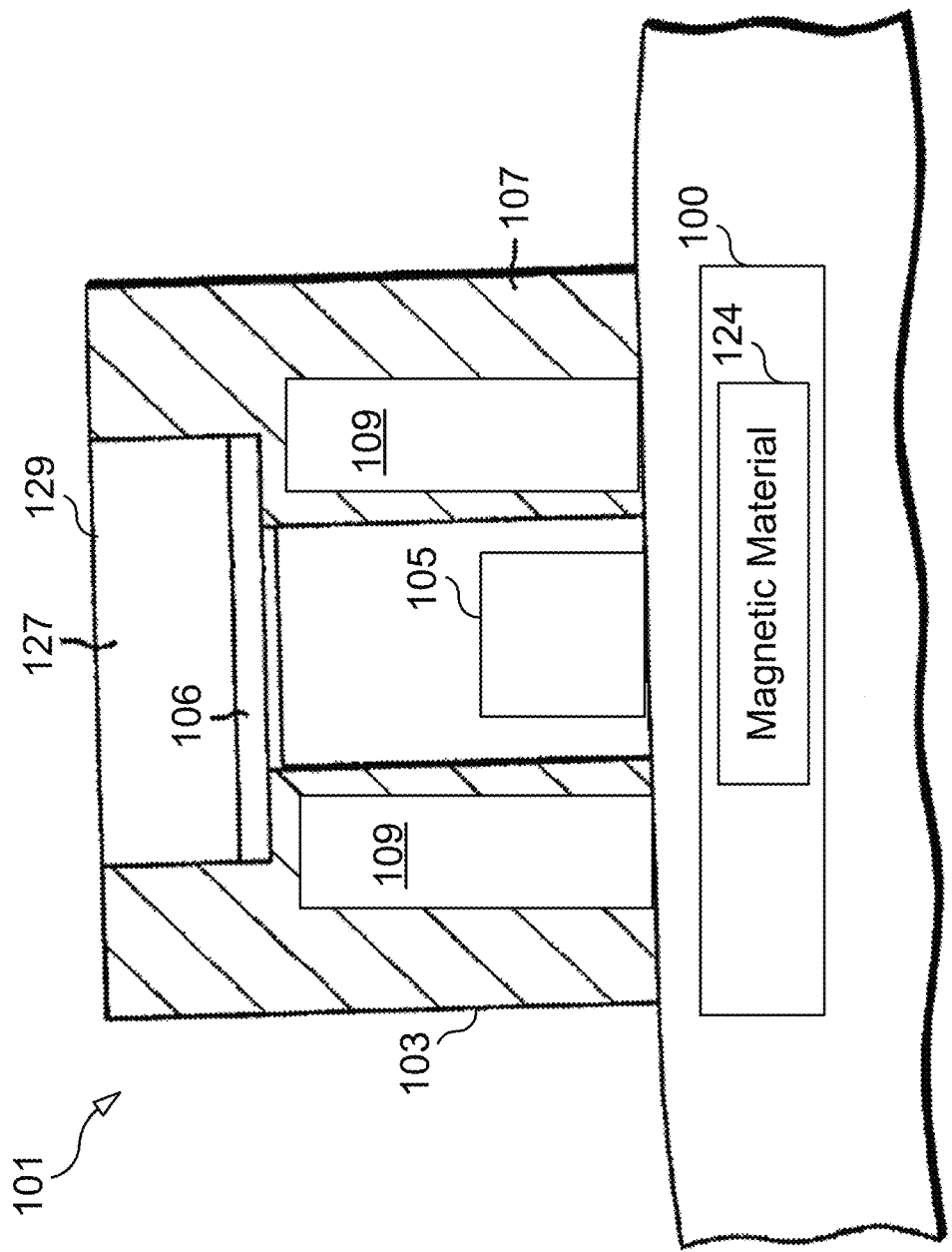
FIG. 7A is a cross-sectional side view illustrating a non-limiting example of an implant and an implant finder embodying aspects of the present invention.
Figure 7B:
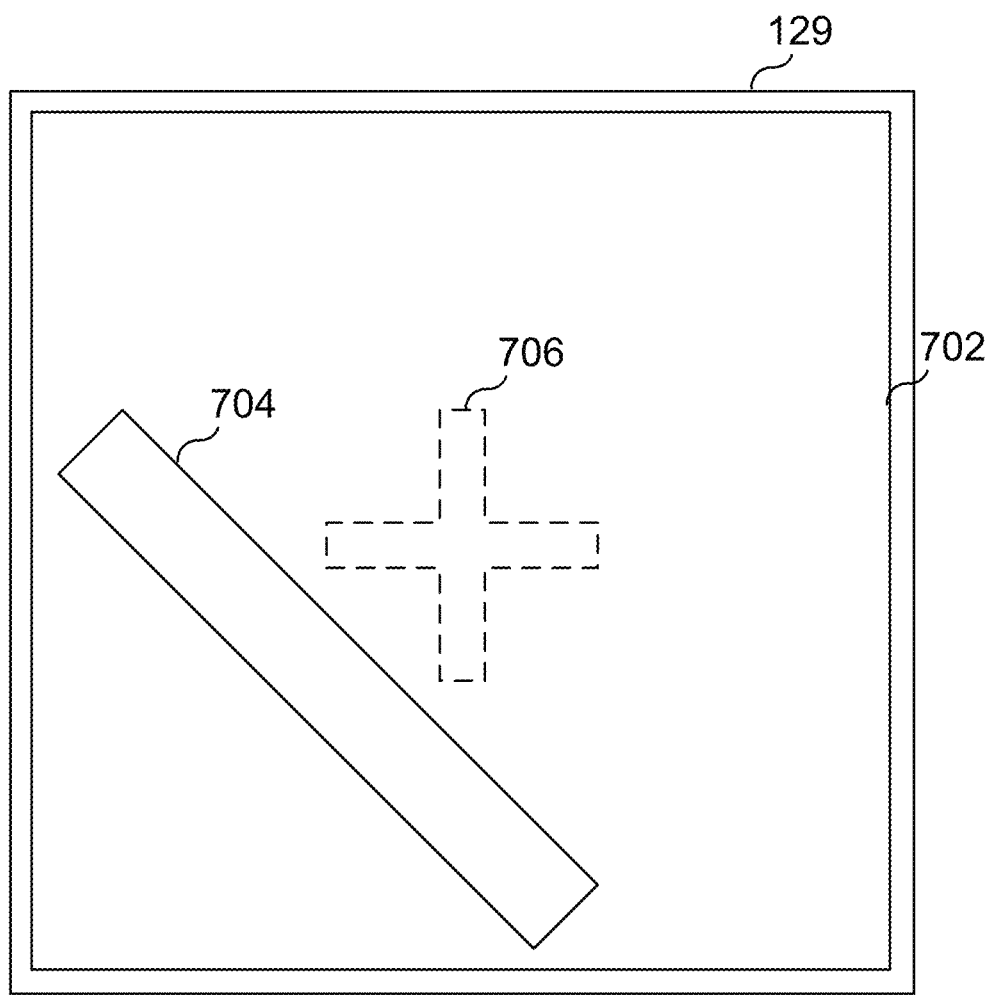
FIGS. 7B-7F illustrate non-limiting examples of a display screen of the user interface of an implant finder embodying aspects of the present invention.

In some aspects, as shown in FIG. 7A, the display 129 of the user interface 127 of the implant finder 101 may be located above the sensor 105. In some aspects, the magnetic field generator 103 may be configured to hold the display 129 in place at the top of the implant finder 101. In some aspects, as shown in FIG. 7A, the housing 107 of the magnetic field generator 103 may be configured to house the one or more magnets 109 of the magnetic field generator 103, the computer 106, and/or the display 129. However, this is not required, and, in some alternative aspects, the display 129 may be located above the magnetic field generator 103.

In some aspects, as shown in FIGS. 7B-7F, the display 129 of the user interface 127 may include a display screen 702. In some aspects (e.g., in some aspects in which the display 129 is located above the sensor 105 and the computer 106 is configured to cause the display 129 to display an indication of the detected location of the implant 100), the indication of the detected location of the implant 100 may include an implant image 704, and a location of the implant image 704 on the screen 702 of the display 129 relative to a point on (e.g., the center of) the screen 702 of the display 129 may correspond to the detected location of the implant 100 relative to the sensor 105. In some aspects, as shown in FIGS. 7B-7E, the implant image 704 may have an orientation that corresponds to an orientation of the implant 100 detected by the computer 106 using sensor signals generated by the sensor 105.

Figure 7C:
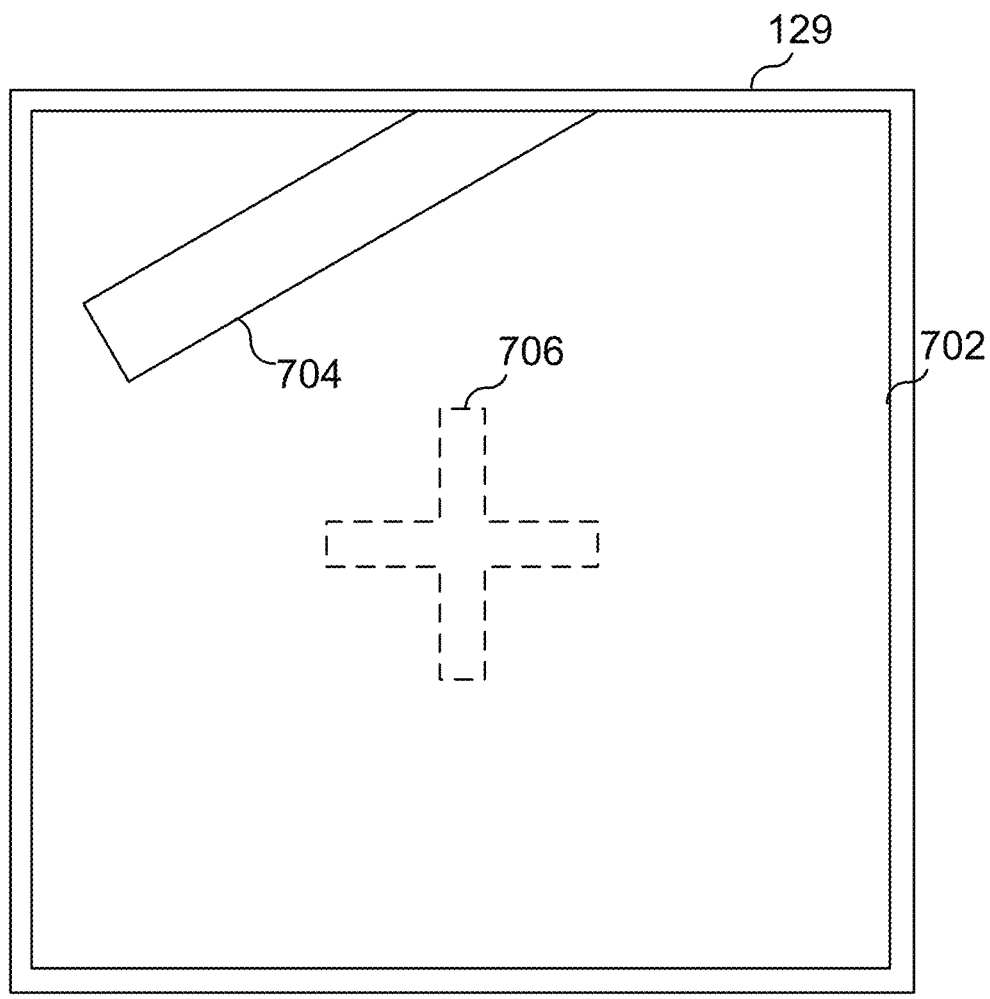
Figure 7D:
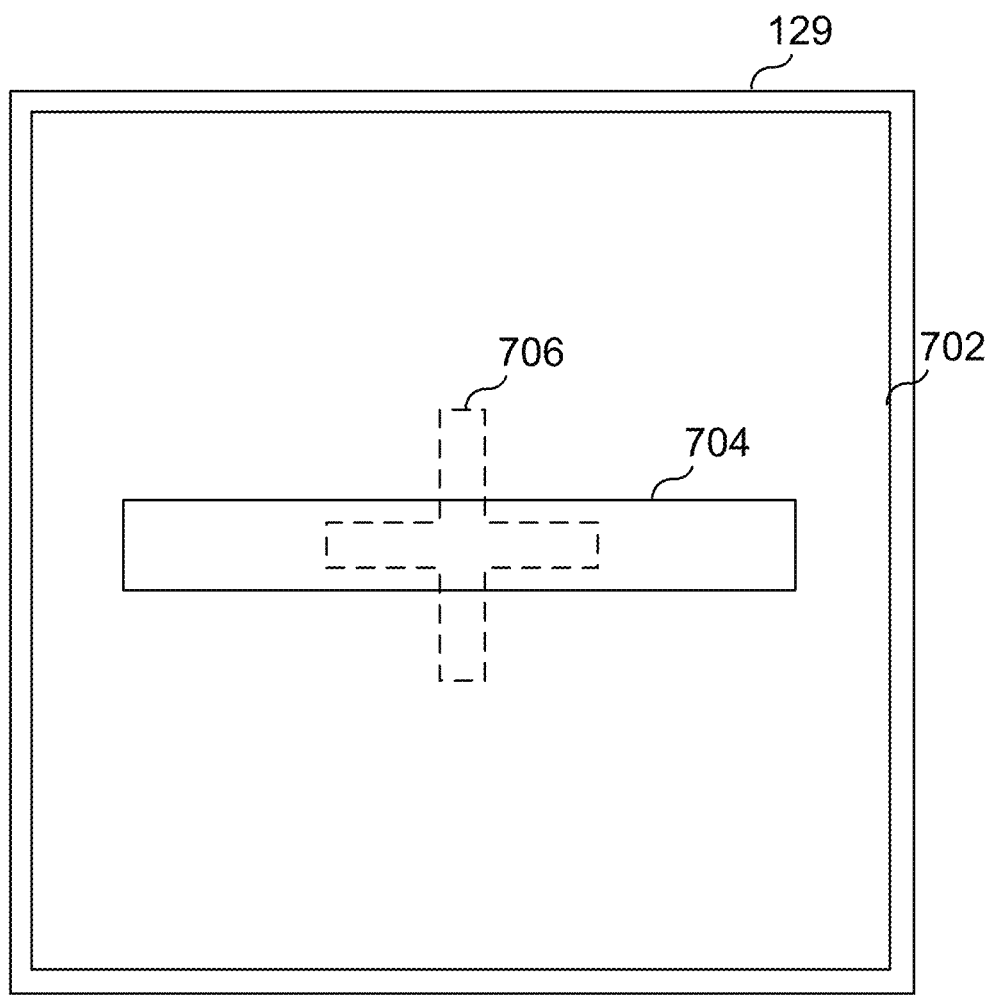
Figure 7E:
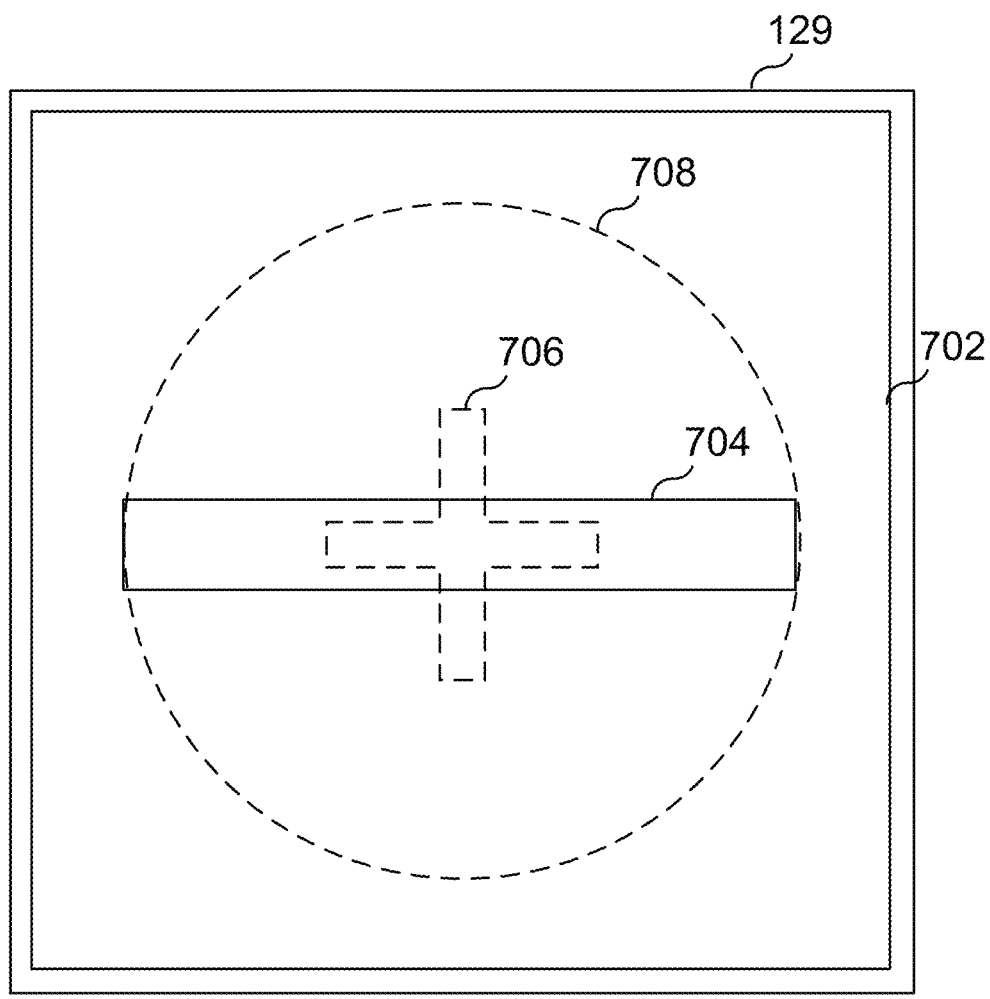
Figure 7F:
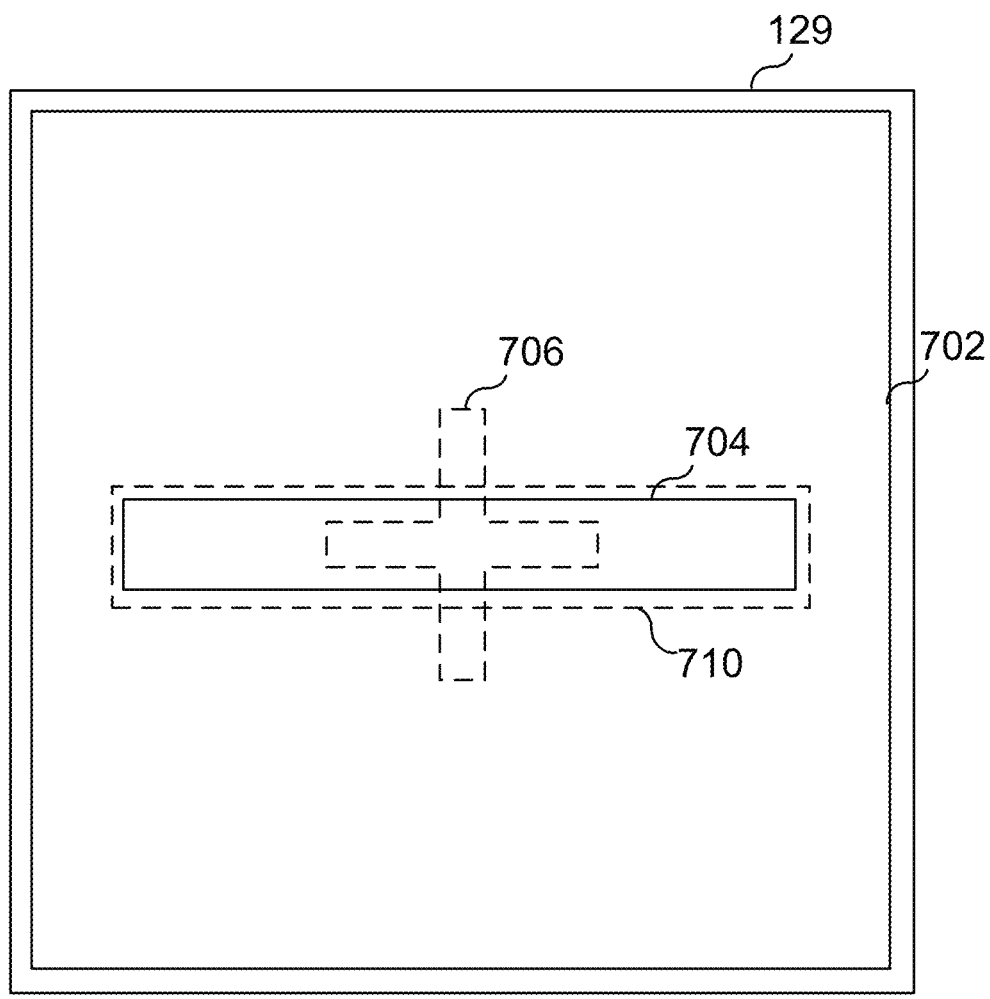

In some aspects, as shown in FIG. 7C, depending on the location of the implant 100 relative to the sensor 105, the implant image 704 may be a partial implant image. In some aspects, as shown in FIGS. 7B-7F, a mark 706 may identify the point on the screen 702 that corresponds to the location of the sensor 105. In some aspects (e.g., some aspects in which the screen 702 of the display 129 is larger than and/or extends beyond the magnetic field generator 103), as shown in FIG. 7E, the computer 106 may cause the display 129 to display a magnetic field generator image 708 indicative of the location of the outer perimeter of the magnetic field generator 103. In some aspects, the location of the implant image 704 relative to the magnetic field generator image 708 may correspond to the detected location of the implant 100 relative to the location of magnetic field generator 103. In some aspects, as shown in FIG. 7F, the computer 106 may cause the display 129 to display a target region 710, and the implant finder 101 may be properly positioned over the implant 100 such that the incision location can be marked (e.g., using the incision marking tool 113) when the implant image 704 is located within the target region 710.

Figure 8A:
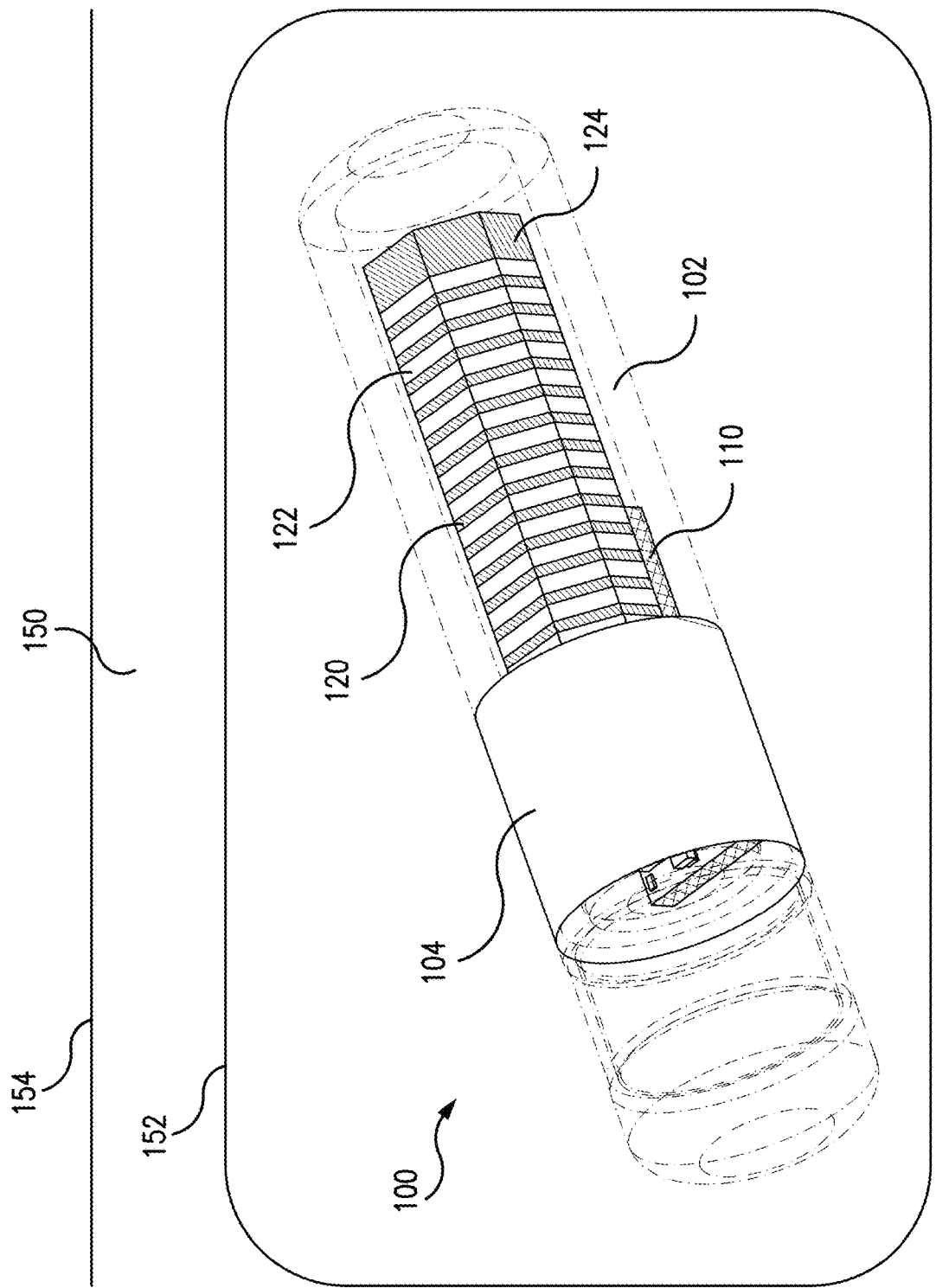
FIGS. 8A and 8B are perspective views illustrating a non-limiting example of an implant embodying aspects of the present invention.
Figure 8B:
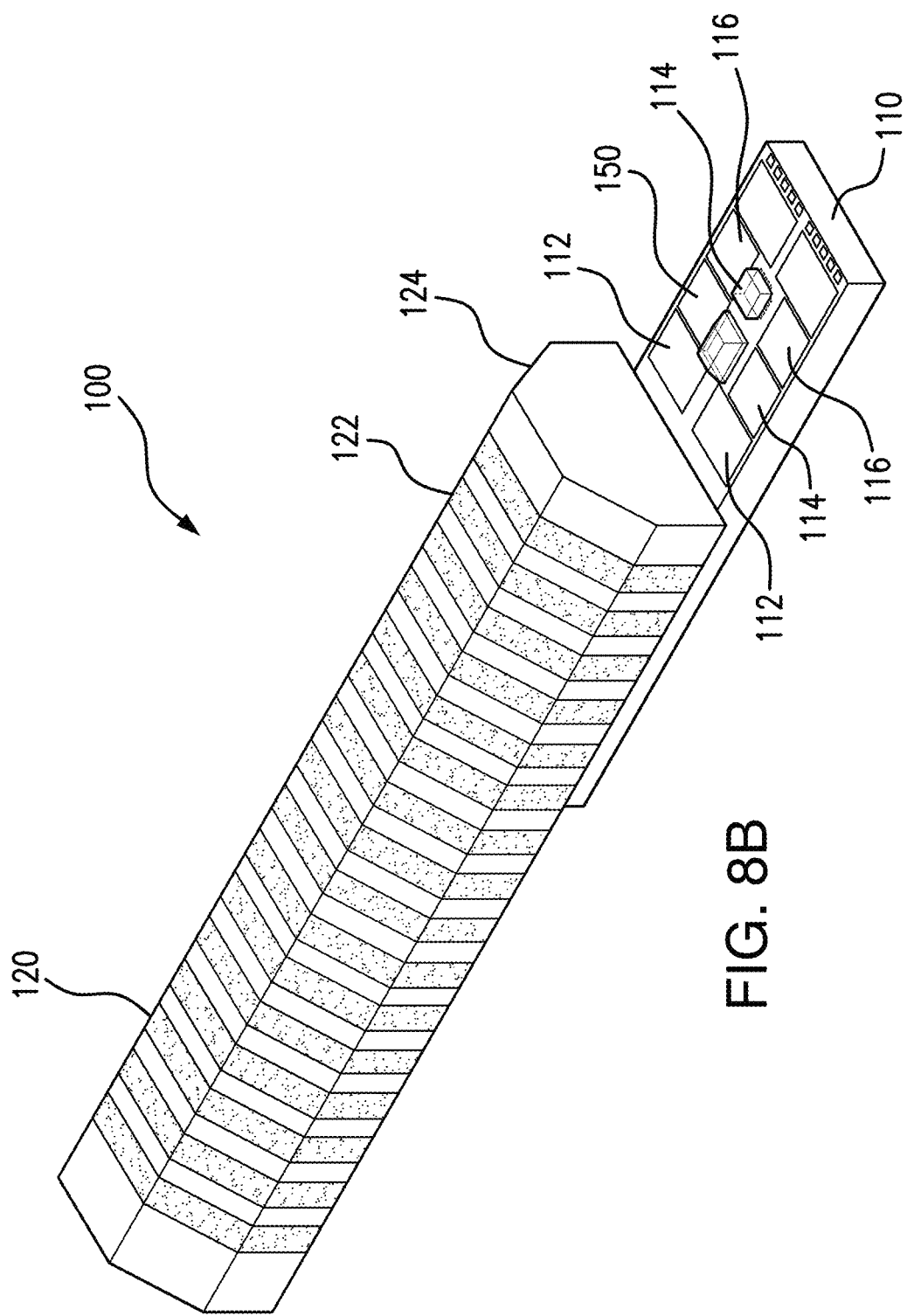

FIGS. 8A and 8B illustrate a non-limiting example of an implant 100 that may be located by the implant finder 101. In some aspects, the implant 100 may be a small, fully subcutaneously implantable sensor, e.g., that measures the amount or concentration of an analyte (e.g., glucose) in a medium (e.g., interstitial fluid) of a living animal (e.g., a living human). In some alternative aspects, the implant 100 is not a sensor and may instead be a different type of implantable device, such as, for example and without limitation, a tag, an insulin pump, a pacemaker, or an electrical/heat therapy device.

In some aspects, as illustrated in FIG. 8A, the implant 100 may be implanted in the tissue 150 (e.g., subcutaneous tissue) of the living animal, where the implant 100 may rest in a pocket 152 in the tissue 150 below the skin surface 154, and the pocket 152 may surround the implant 100. In some aspects, the pocket 152 may be created by a tissue dissector tool before implantation of the implant 100 or by the implantation process.

In some aspects, as illustrated in FIG. 8A, the implant 100 may include a housing 102 and one or more analyte indicators 104 coated, diffused, adhered, embedded, or grown on or in at least a portion of the exterior surface of the housing 102. In some aspects, the one or more analyte indicators 104 (e.g., polymer grafts or hydrogels) of the implant 100 may include one or more indicator molecules (e.g., fluorescent indicator molecules). In some aspects, the indicator molecules may produce (e.g., exhibit) one or more detectable properties (e.g., optical properties) that vary in accordance with the amount or concentration of the analyte in proximity to an analyte indicator 104. In some aspects, the indicator molecules may emit an amount of emission light (e.g., fluorescent light) that varies in accordance with the amount or concentration of the analyte in proximity to the analyte indicator 104.

In some embodiments, the implant 100 may include a substrate 110 (e.g., a printed circuit board (PCB) or flexible PCB), one or more light sources 111 mounted on or fabricated in the substrate 110, and one or more photodetectors 112, 114, and 116 (e.g., photodiodes, phototransistors, photoresistors, or other photosensitive elements) mounted on or fabricated in the substrate 110. In some embodiments, the light source 111 may be configured to emit an excitation light over an excitation wavelength range that interacts with the one or more indicator molecules in the analyte indicator 104. In some aspects, one or more of the photodetectors 112, 114, and 116 may output a signal indicative of an amount of light received by the photodetector. In some examples, the signal output by the one or more internal photodetectors 112, 114, and 116 may be indicative of an amount or concentration of an analyte in a medium in proximity to the analyte indicator 104.

In some aspects, as shown in FIGS. 8A and 8B, the implant 100 may include an inductor 120, which may be, for example, a ferrite based micro-antenna. In some aspects, the inductor 120 may include a conductor 122 in the form of a coil and a magnetic material 124 in form of a magnetic core 124. In some aspects, the core 124 may be, for example and without limitation, a ferrite core. In some aspects, the inductor 120 may be connected to circuitry (e.g., an application specification integrated circuit (ASIC)) of the implantable device 100. In some aspects, the inductor 120 may communicate with an external device (not shown) by, passive telemetry (e.g., near field communication), such that power and/or data is transferred between the implant 100 and the external device.

Figure 9A:
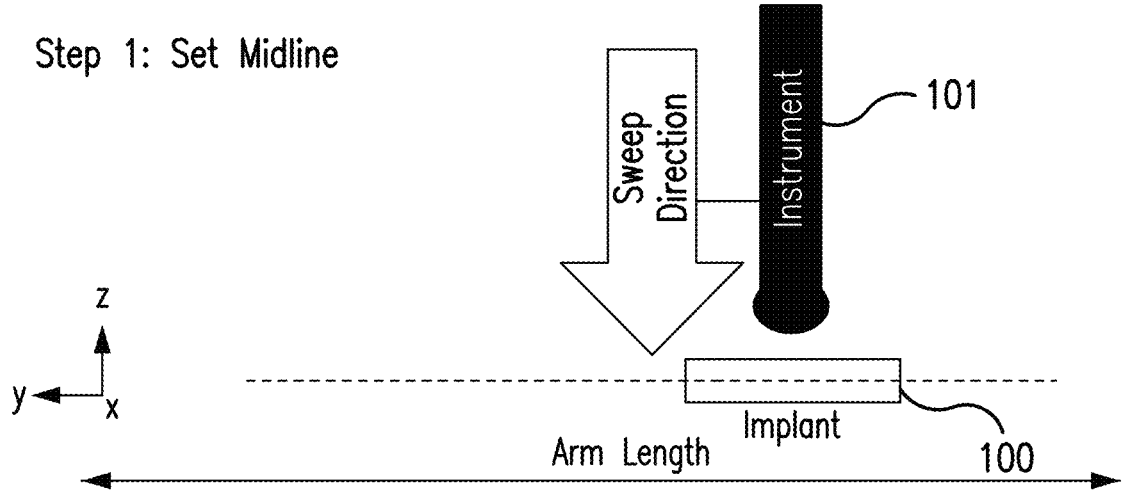
FIGS. 9A and 9B illustrate movement of the implant finder across a longitudinal axis of an implant that is not tilted relative to the skin surface and a magnitude of changes to a magnetic field during the movement, respectively, embodying aspects of the present invention.
Figure 10A:
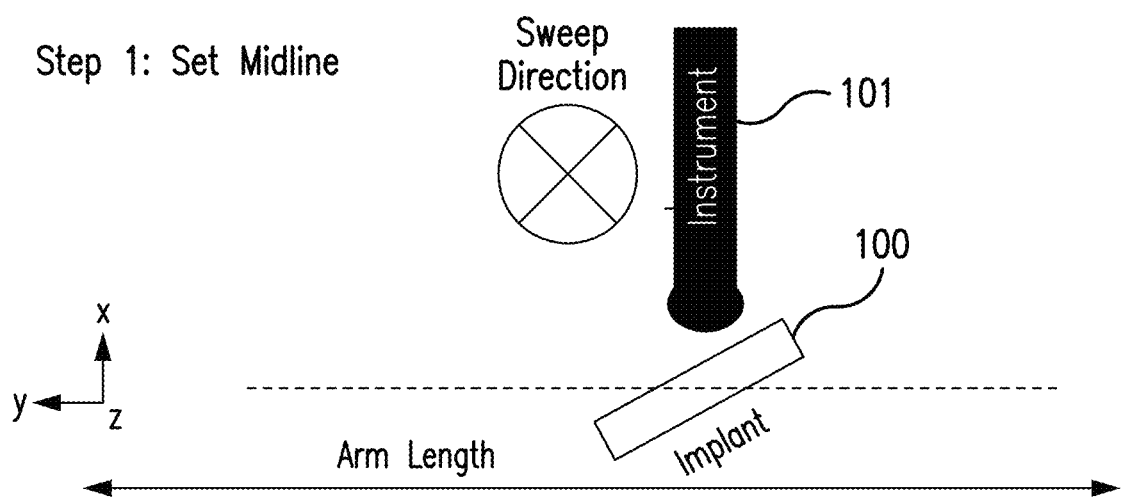
FIGS. 10A and 10B illustrate movement of the implant finder across a longitudinal axis of a downward-tilted implant and a magnitude of changes to a magnetic field during the movement, respectively, embodying aspects of the present invention.
Figure 11A:
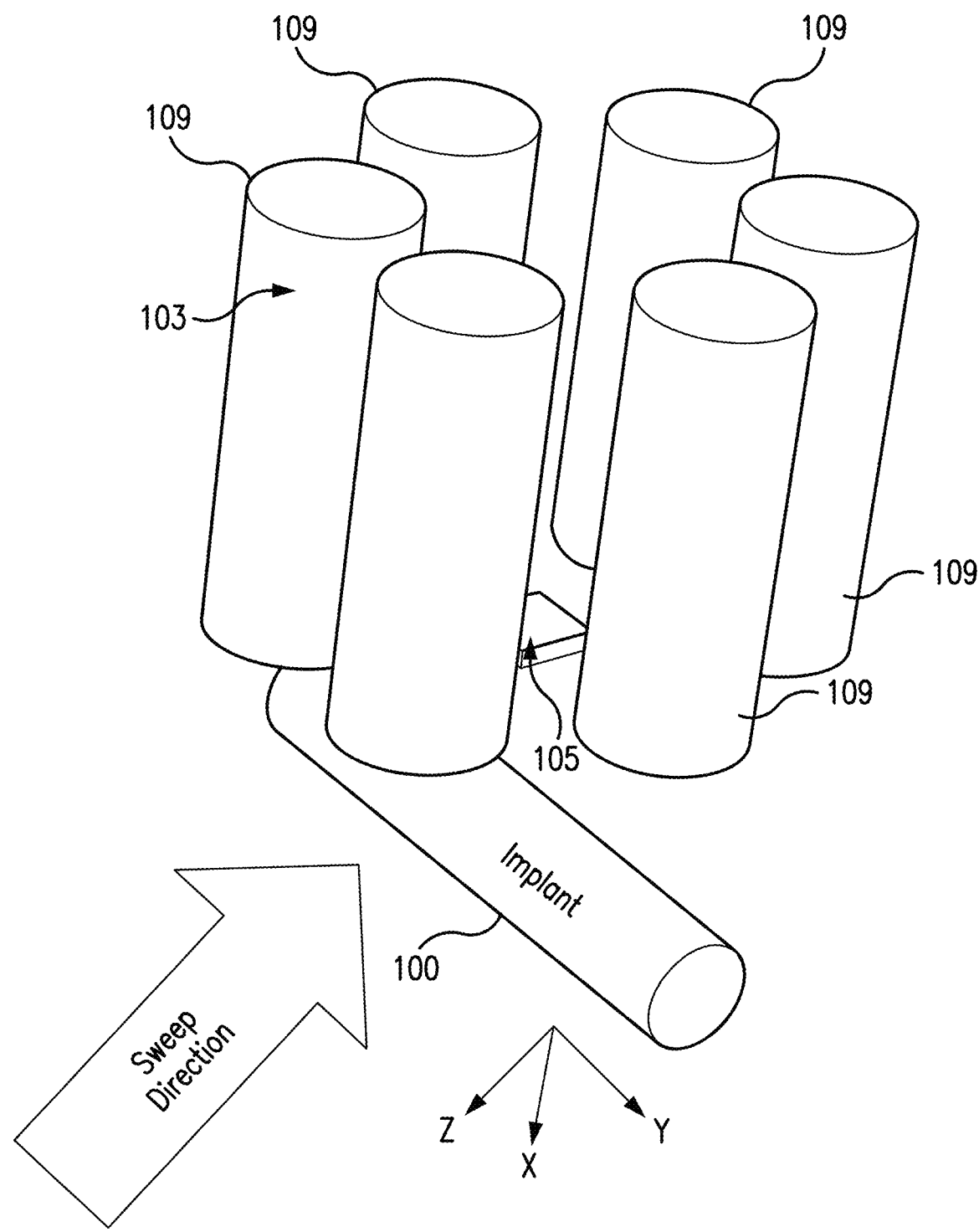
FIGS. 11A and 11B illustrate movement of the implant finder across a longitudinal axis of an implant and a magnitude of changes to a magnetic field during the movement for different distances between the sensor and implant, respectively, embodying aspects of the present invention.

In some aspects, the implant finder 101 may be used for locating an implant 100 (e.g., an implant 100 that has been implanted in tissue 150 below a skin surface 154 of a living animal). In some aspects, a first process for locating the implant 100 may include a first step of determining a midline of the implant 100. In some aspects, determining the midline of the implant 100 may include, as shown in FIGS. 9A, 10A, and 11A, moving the implant finder 101 across (e.g., transverse to) a longitudinal axis of the implant 100. FIGS. 9A and 10A illustrate the movement of the implant finder 101 across the longitudinal axis of an implant 100 that is not tilted relative to the skin surface and across the longitudinal axis of a downward-tilted implant 100, respectively. In some aspects, the orientation of the implant 100 may be assumed (e.g., the longitudinal axis of an implant 100 implanted in an arm of a living animal may be assumed to be approximately along the long axis of the arm), and the movement of the implant finder 101 across the longitudinal axis of the implant 100 may be transverse to the assumed orientation of the implant 100. In some aspects, the orientation of the implant 100 may be determined using records regarding the implantation of the implant 100, and the movement of the implant finder 101 across the longitudinal axis of the implant 100 may be transverse to the orientation of the implant 100 determined using the implantation records.

In some aspects, locating the implant 100 may include using implantation information for the implant 100. In some aspects, the implantation information may include implantation location information identifying the location at which the implant 100 was implanted, and the implantation location information may be used to identify and/or limit an initial search area for the implant 100. In some aspects, the implantation information may additionally or alternatively include implantation depth information identifying the depth at which the implant was implanted, and the implantation depth information may be used to estimate an expected signal range. In some aspects in which there is an offset between the center of the magnetic material 124 and the center of the implant 100, the implantation information may additionally or alternatively include offset direction information identifying a direction of the offset of the center of the magnetic material 124 relative to the center of the implant 100, which may be used for identifying edges of the implant 100 and/or an incision location.

Figure 9B:
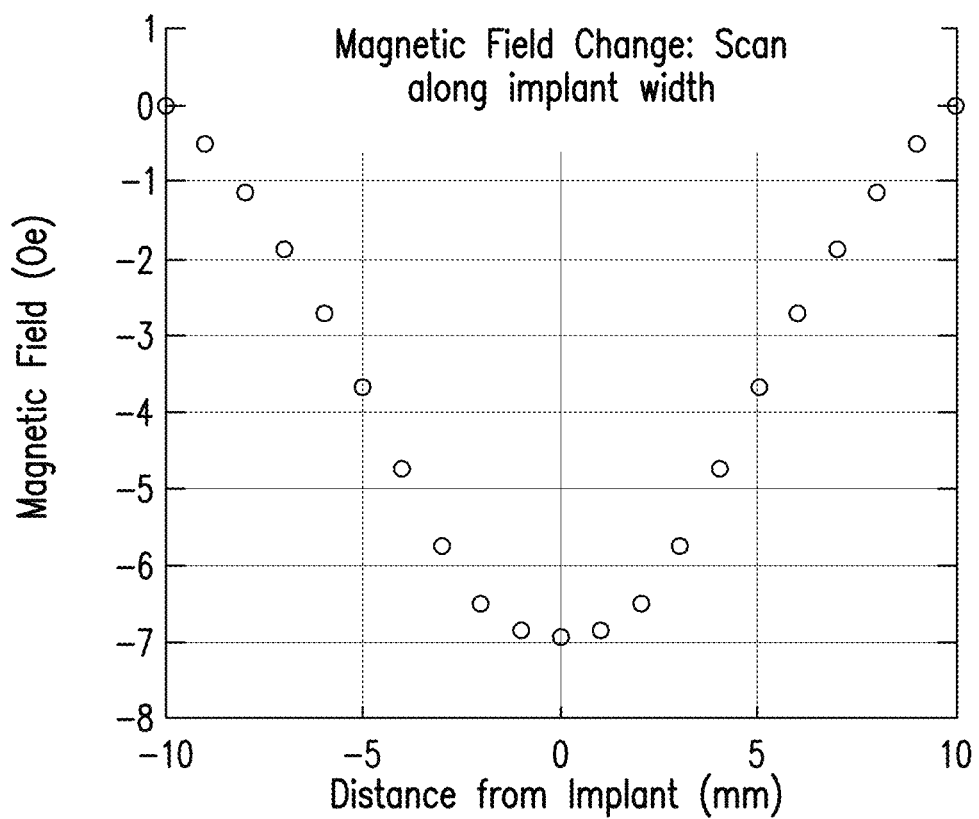
Figure 10B:
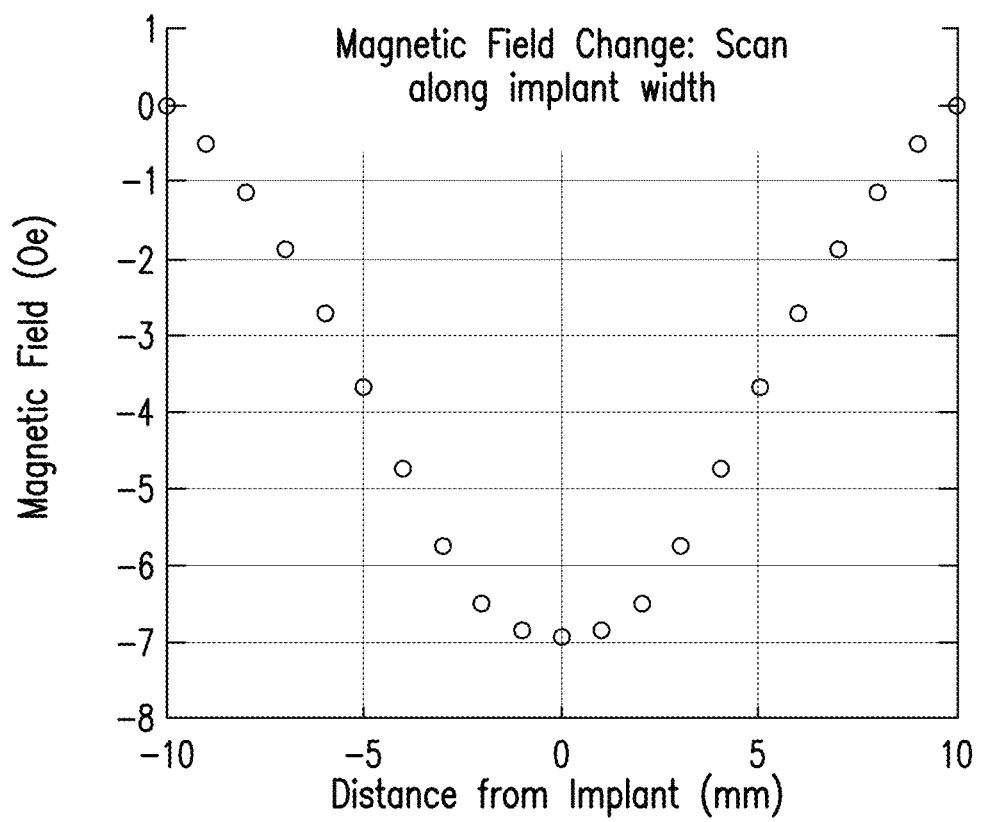
Figure 14A:
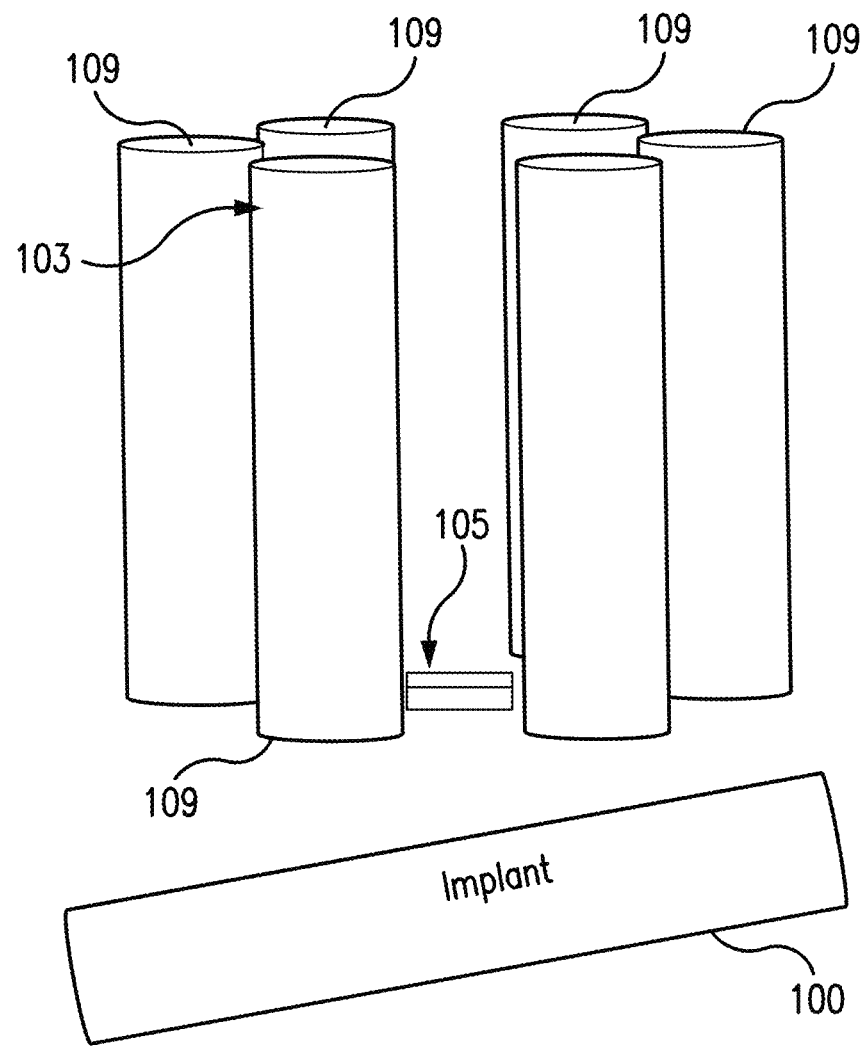
FIGS. 14A-14C illustrate an implant twisted out-of-plane, changes to a magnetic field during movement of the implant finder across a longitudinal axis of the implant, and changes to a magnetic field during movement of the implant finder along a longitudinal axis of the implant, respectively, embodying aspects of the present invention.
Figure 14A:
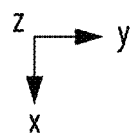
Figure 14A:
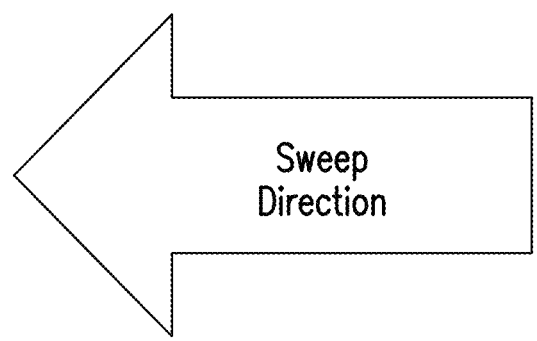
Figure 14B:
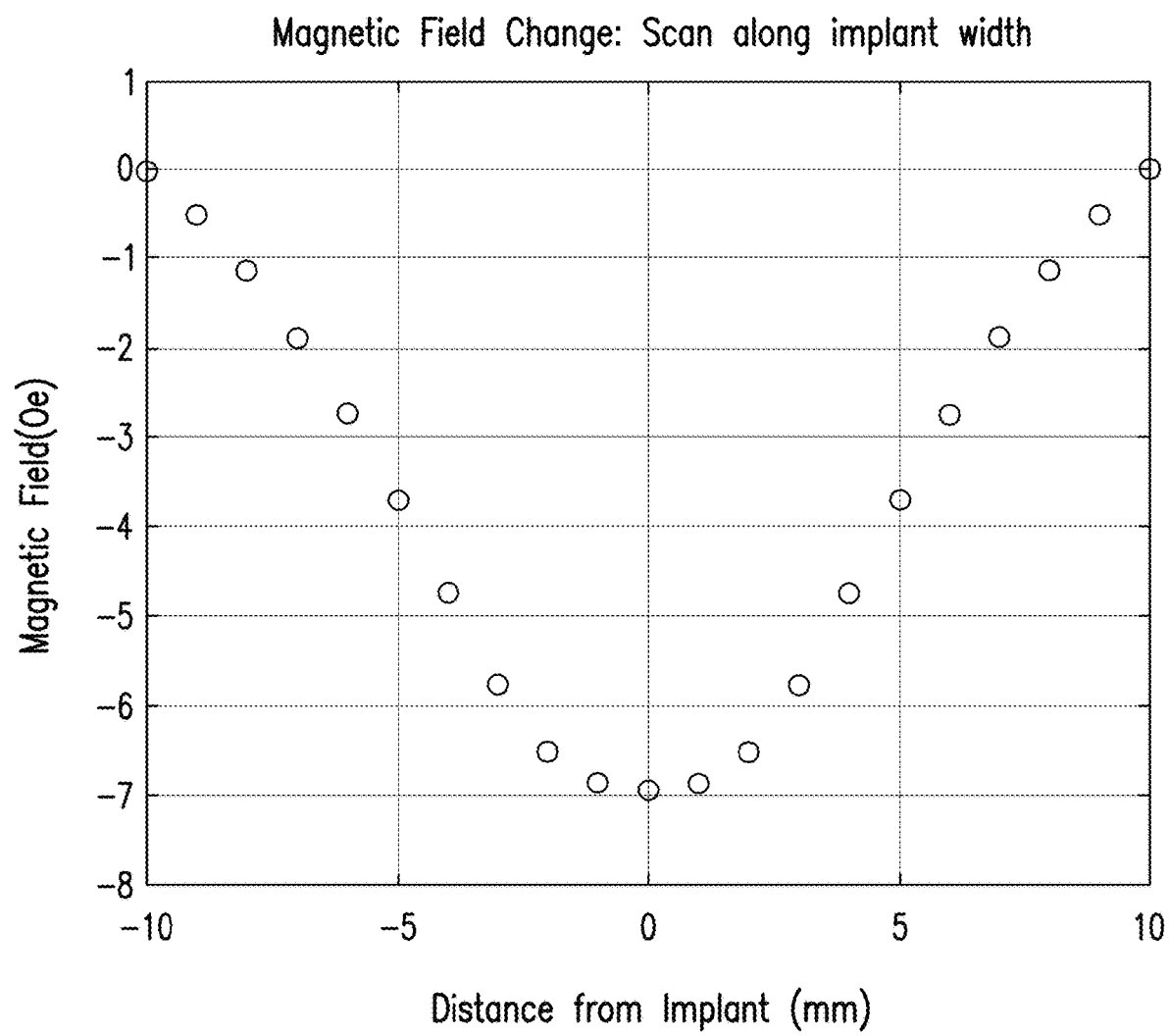

In some aspects, the magnetic material 124 of the implant 100 may cause changes in a magnetic field generated by the magnetic field generator 103 of the implant finder 101 as the implant finder 101 is moved across the longitudinal axis of the implant 100, and the sensor 105 of the implant finder 101 may detect changes in the magnetic field. FIG. 9B illustrates changes in the magnetic field caused by the magnetic material 124 of the implant 100 that is not tilted relative to the skin surface as detected by the sensor 105 during movement across the longitudinal axis of the implant 100 according to some aspects. FIGS. 10B and 14B illustrate changes in the magnetic field caused by the magnetic material 124 of an out-of-plane or downward-tilted implant 100 as detected by the sensor 105 during movement across the longitudinal axis of the implant 100 according to some aspects. In some aspects, as shown in FIGS. 9B, 10B, and 14B, the change in the magnetic field as the implant finder 101 is moved across the longitudinal axis of the implant 100 may be greatest at the location of the midline of the implant 100.

In some aspects, the implant finder 101 (e.g., the computer 106 of the implant finder 101) may be configured to determine the midline of the implant 100 based on a location where the changes in the magnetic field are greatest as the implant finder 101 is moved across the longitudinal axis of the implant 100. In some aspects, the computer 106 of the implant finder 101 may be configured to determine a derivative of the detected changes in the magnetic field, and the computer 106 may be configured to determine the midline of the implant 100 (and the location where the changes in the magnetic field are greatest) based on a location where the derivative of the changes in the magnetic field equals zero during movement of the sensor 105 across a longitudinal axis of the implant 100. In some aspects, the derivative of the changes in the magnetic field may be with respect to time (as the sensor 105 is moved across the longitudinal axis of the implant 100). In some alternative aspects, the derivative of the changes in the magnetic field may be with respect to the position of the sensor (as the sensor 105 is moved across the longitudinal axis of the implant 100).

In some aspects, the implant finder 101 (e.g., the computer 106 of the implant finder 101) may cause the user interface 127 to indicate when the implant finder 101 (e.g., the computer 106) has detected the midline of the implant 100 (e.g., when the computer 106 determines the derivative of the changes in the magnetic field equals zero during movement of the sensor 105 across the longitudinal axis of the implant 100). In some aspects, the user interface 127 may indicate detection of the midline using one or more of the display 129 (e.g., by displaying a visual indicator of midline detection), speaker 131 (e.g., by emitting an audible sound such as, for example and without limitation, a beep), and vibration motor 133 (e.g., by vibrating).

Figure 11B:
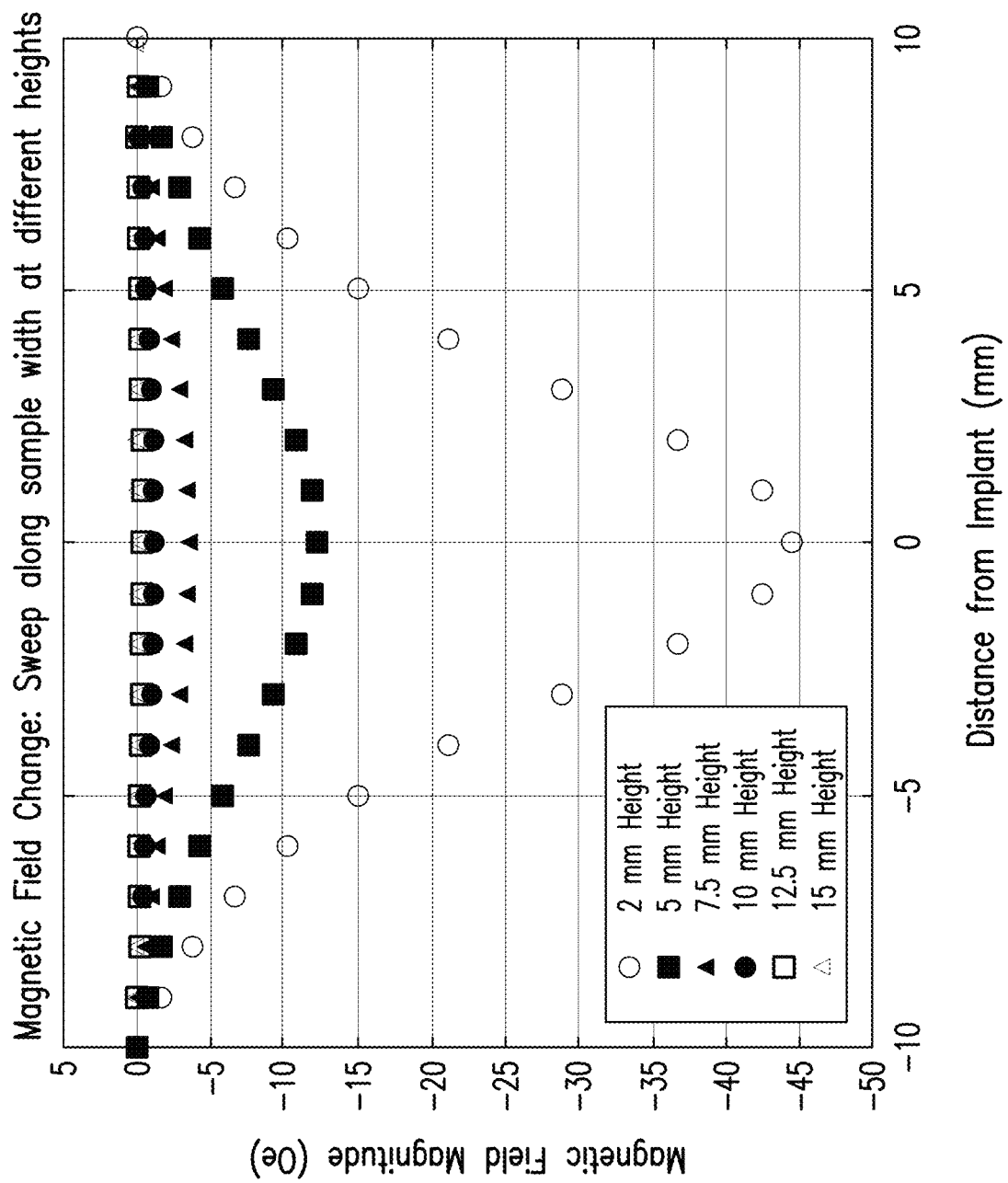

FIG. 11B illustrates detected magnetic field changes as the implant finder 101 is moved across the longitudinal axis of the implant 100 for implants 100 at different heights of the sensor 105 of the implant finder 101 relative to the implant 100. As shown in FIG. 11B, the magnitudes of the detected magnetic field changes increase as the height decreases. Accordingly, the implant finder 101 (e.g., the computer 106 of the implant finder 101) may be configured to use the magnitude of the detected magnetic field change at the midline (e.g., the greatest detected magnetic field change during movement of the sensor 105 across the longitudinal axis of the implant 100) to determine the depth of the implant 100 in the tissue 150.

Figure 9C:
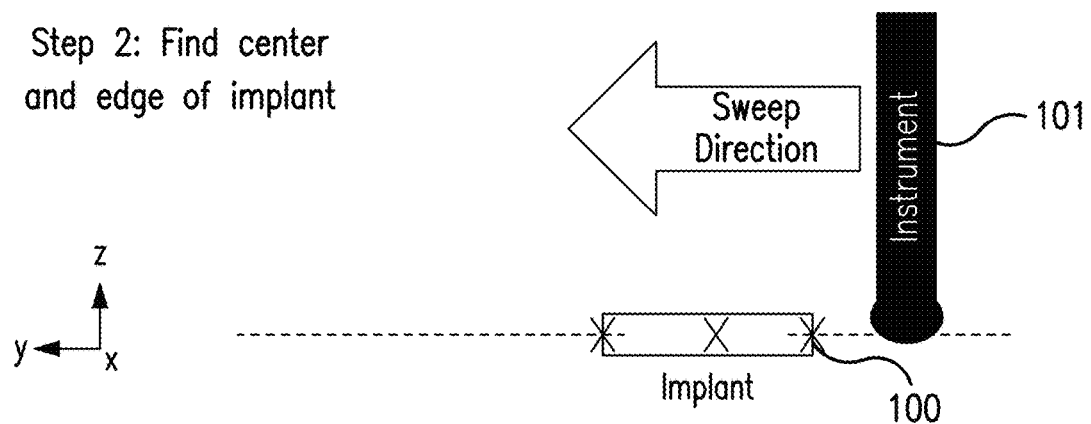
FIGS. 9C and 9D illustrate movement of the implant finder along a longitudinal axis of the implant that is not tilted relative to the skin surface and a magnitude of changes to a magnetic field during the movement, respectively, embodying aspects of the present invention.
Figure 10C:
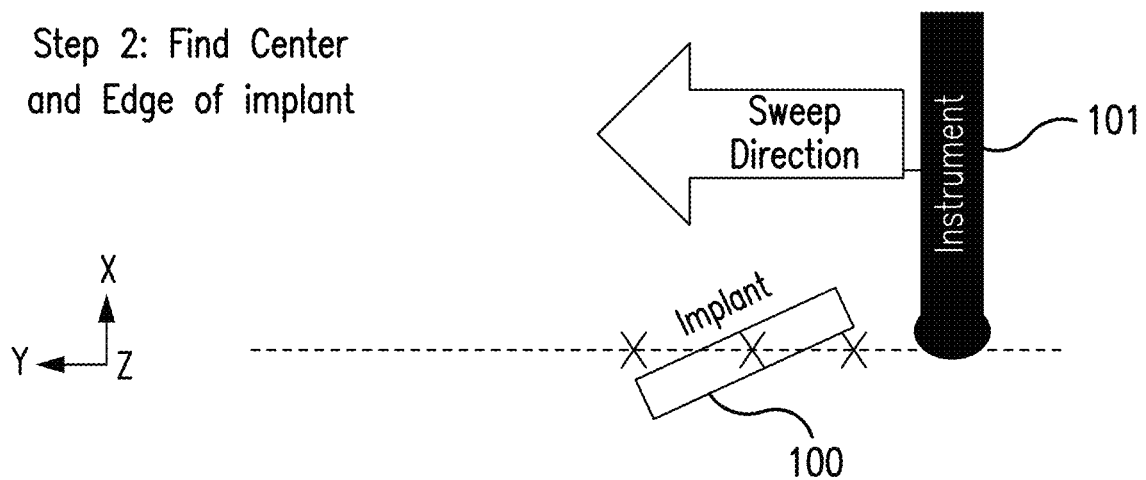
FIGS. 10C and 10D illustrate movement of the implant finder along a longitudinal axis of the downward-tilted implant and a magnitude of changes to a magnetic field during the movement, respectively, embodying aspects of the present invention.

In some aspects, the first process for locating the implant 100 may include a second step of determining one or more edges of the magnetic material 124 of the implant 100 and/or a center of the magnetic material 124 of the implant 101. In some aspects, determining the edge(s) and/or center of magnetic material 124 of the implant 100 may include, as shown in FIGS. 9C, 10C, 12A, and 14A, moving the implant finder 101 along a longitudinal axis of the implant 100. FIG. 9C illustrated the movement of the implant finder 101 along the longitudinal axis of an implant 100 that is not tilted relative to the skin surface. FIGS. 10C and 14A illustrate the movement of the implant finder 101 along the longitudinal axis of a downward-tilted or out-of-plane implant 100. In some aspects, the determined midline may be used to move the implant finder 101 along the longitudinal axis of the implant 100. For example, in some aspects, moving the implant finder 101 along the longitudinal axis of the implant 100 may include moving implant finder 101 on the skin surface 154 along the determined midline of the implant 100. In some aspects, the movement along the longitudinal axis of the implant 100 may be parallel to the assumed orientation of the implant 100. In some aspects, the movement along the longitudinal axis of the implant 100 may be parallel to the orientation of the implant 100 determined using implantation records.

Figure 9D:
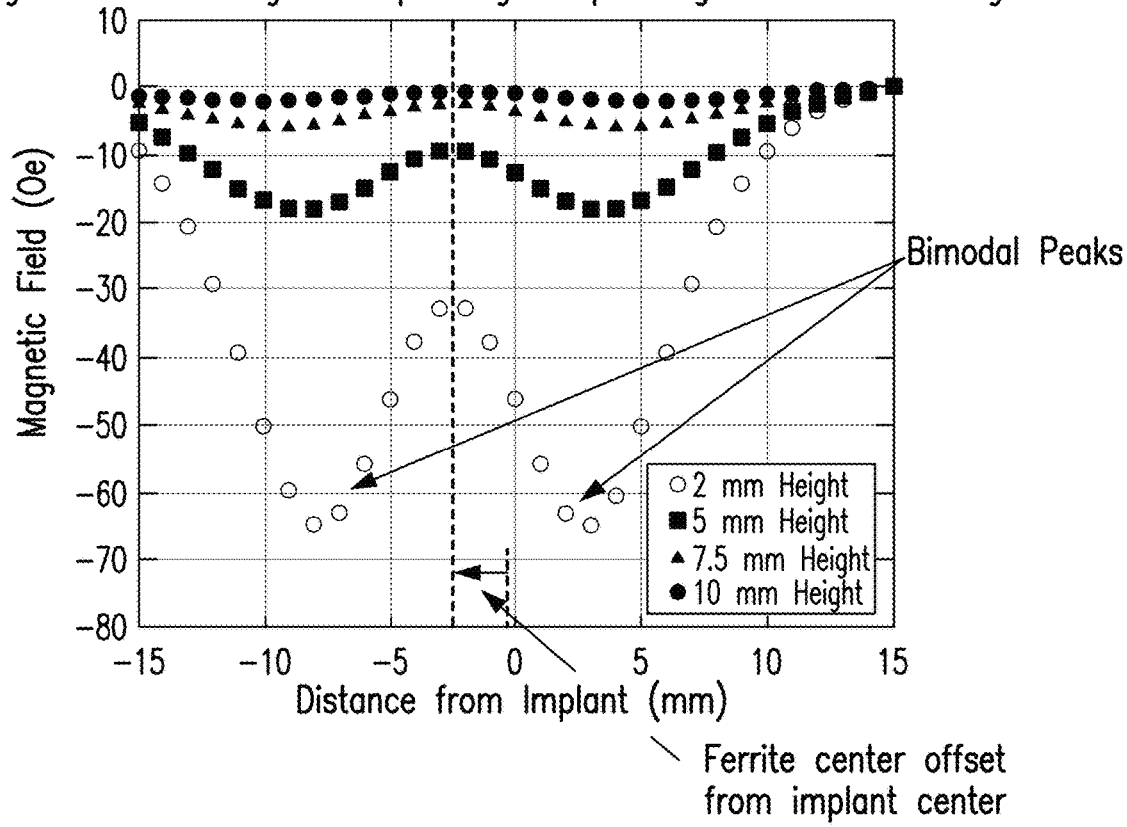
Figure 10D:
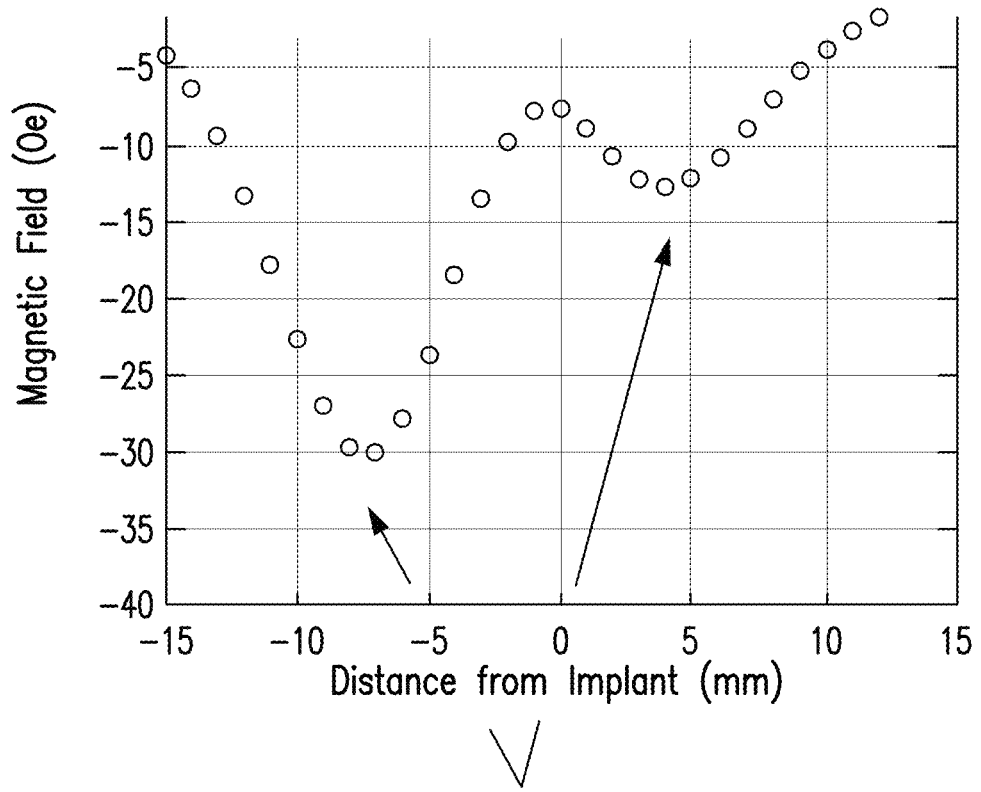
Figure 14C:
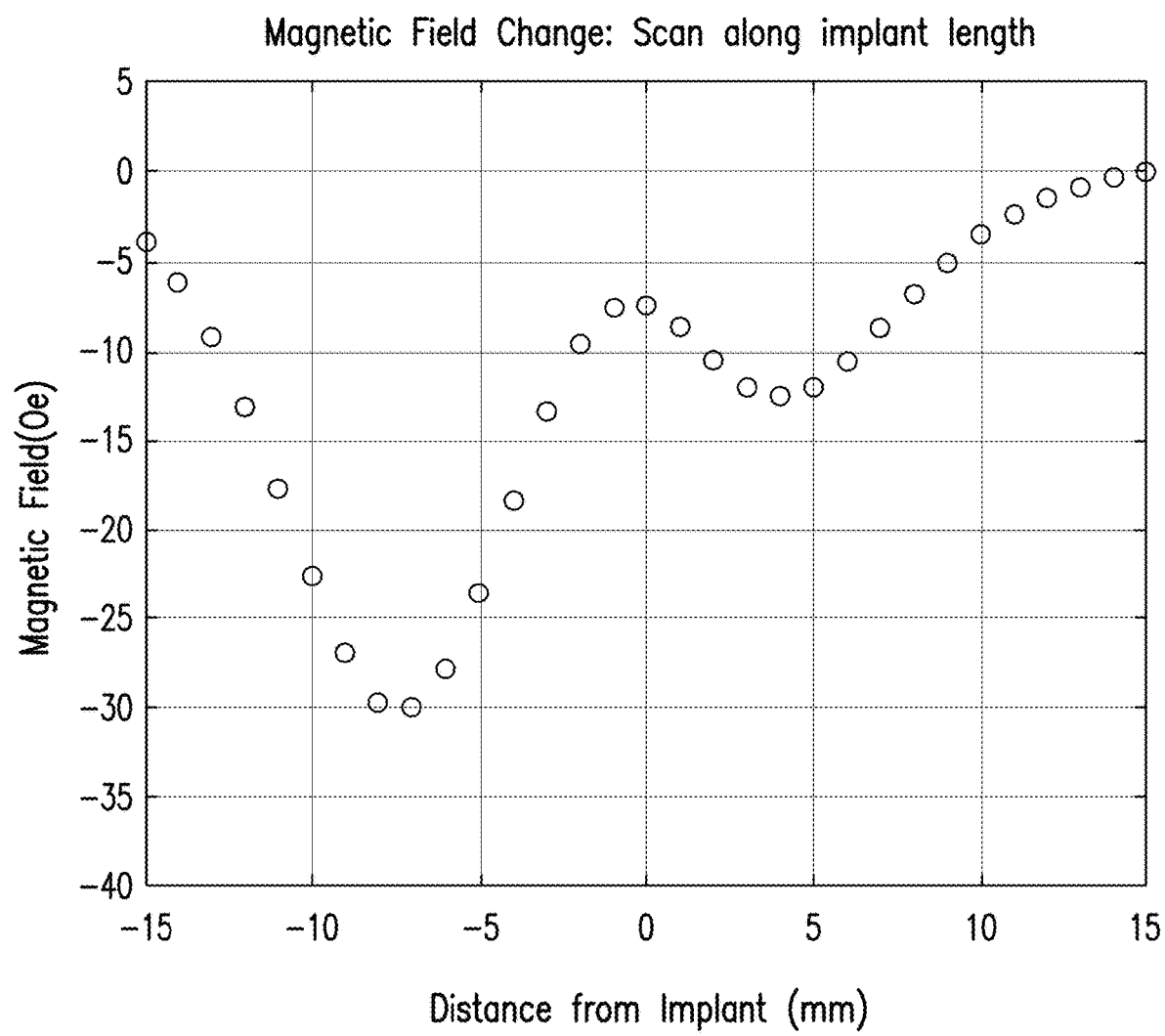

In some aspects, the magnetic material 124 of the implant 100 may cause changes in a magnetic field generated by the magnetic field generator 103 of the implant finder 101 as the implant finder 101 is moved along the longitudinal axis of the implant 100, and the sensor 105 of the implant finder 101 may detect changes in the magnetic field. FIG. 9D illustrates changes in the magnetic field caused by the magnetic material 124 of an implant 100 that is not tilted relative to the skin surface as detected by the sensor 105 during movement along the longitudinal axis of the implant 100 according to some aspects. FIGS. 10D and 14C illustrate changes in the magnetic field caused by the magnetic material 124 of an out-of-plane or downward-tilted implant 100 as detected by the sensor 105 during movement along the longitudinal axis of the implant 100 according to some aspects. In some aspects, as shown in FIGS. 9D, 10D, and 14C, the detected changes in the magnetic field as the implant finder 101 is moved along the longitudinal axis of the implant 100 may include bimodal peaks (e.g., local maxima) at the locations of the edges of the magnetic material 124 of the implant 100. In some aspects, as shown in FIGS. 9D, 10D, and 14C, the changes in the magnetic field may include a local minimum between the bimodal peaks at a location of the center of the magnetic material 124 of the implant 100.

In some aspects, the implant finder 101 (e.g., the computer 106 of the implant finder 101) may be configured to determine edges of the magnetic material 124 of the implant 100 based on locations of the bimodal peaks in the changes in the magnetic field. In some aspects, the computer 106 of the implant finder 101 may be configured to determine a derivative of the detected changes in the magnetic field, and the computer 106 may be configured to determine the edges of the magnetic material 124 of the implant 100 (and the locations of the bimodal peaks in the magnetic field changes) based on a locations where the derivative of the changes in the magnetic field equals zero during movement of the sensor 105 along a longitudinal axis of the implant 100. In some aspects, the derivative of the changes in the magnetic field may be with respect to time (as the sensor 105 is moved along the longitudinal axis of the implant 100). In some alternative aspects, the derivative of the changes in the magnetic field may be with respect to the position of the sensor (as the sensor 105 is moved along the longitudinal axis of the implant 100). In some aspects, the edges of the magnetic material 124 of the implant 100 may be offset from the edges of the implant 100. For example, the edges of the magnetic material 124 of the implant 100 are offset from the edges of the implant 100. In some aspects in which the edges of the magnetic material 124 are offset from the edges of the implant 100, the implant finder 101 (e.g., the computer 106 of the implant finder 101) may be configured to determine one or more edges of the implant 100 using the one or more determined edges of the magnetic material 124 and the offset(s).

In some aspects, the implant finder 101 (e.g., the computer 106 of the implant finder 101) may be configured to determine a center of the magnetic material 124 of the implant 100 based on the location of a local minimum in the magnetic field changes between the bimodal peaks in the magnetic field changes. In some aspects, the computer 106 of the implant finder 101 may be configured to determine a derivative of the detected changes in the magnetic field, and the computer 106 may be configured to determine the center of the magnetic material 124 of the implant 100 (and the locations of local minimum between the bimodal peaks in the magnetic field changes) based on a location where the derivative of the changes in the magnetic field equals zero during movement of the sensor 105 along a longitudinal axis of the implant 100. In some aspects, the center of the magnetic material 124 of the implant 100 may be offset from the center of the implant 100 (i.e., the center of the magnetic material 124 may be different than the center of the implant 100). For example, in the implant 100 illustrated in FIG. 8A, the center of the magnetic material 124 of the implant 100 is offset from the center of the implant 100 (e.g., by 2.5 mm). In some aspects in which the magnetic material 124 is offset from the center of the implant 100, the implant finder 101 (e.g., the computer 106 of the implant finder 101) may be configured to determine a center of the implant 100 using the determined center of the magnetic material 124 and the offset. In some aspects, the direction of the offset of the center of the magnetic material 124 relative to the center of the implant 100 may be assumed (e.g., the center of the magnetic material 124 may be assumed to be higher along the long axis of the arm than the center of the implant 100). In some aspects, the direction of the offset of the center of the magnetic material 124 relative to the center of the implant 100 may be additionally or alternatively confirmed or determined (e.g., using implantation records and/or detected changes in the magnetic field caused by metal and/or circuitry on and/or in the substrate 110, which may extend from one side of the magnetic material 124 of the implant 100 as shown in FIGS. 8A and 8B).

In some aspects, the implant finder 101 (e.g., the computer 106 of the implant finder 101) may cause the user interface 127 to indicate when the implant finder 101 (e.g., the computer 106) has detected the edges and/or center of the magnetic material 124 of the implant 100 (e.g., when the computer 106 determines the derivative of the changes in the magnetic field equals zero during movement of the sensor 105 along the longitudinal axis of the implant 100). In some aspects, the user interface 127 may indicate detection of the edges and/or center using one or more of the display 129 (e.g., by displaying a visual indicator of edges and/or center detection), speaker 131 (e.g., by emitting an audible sound such as, for example and without limitation, a beep), and vibration motor 133 (e.g., by vibrating).

Figure 12A:
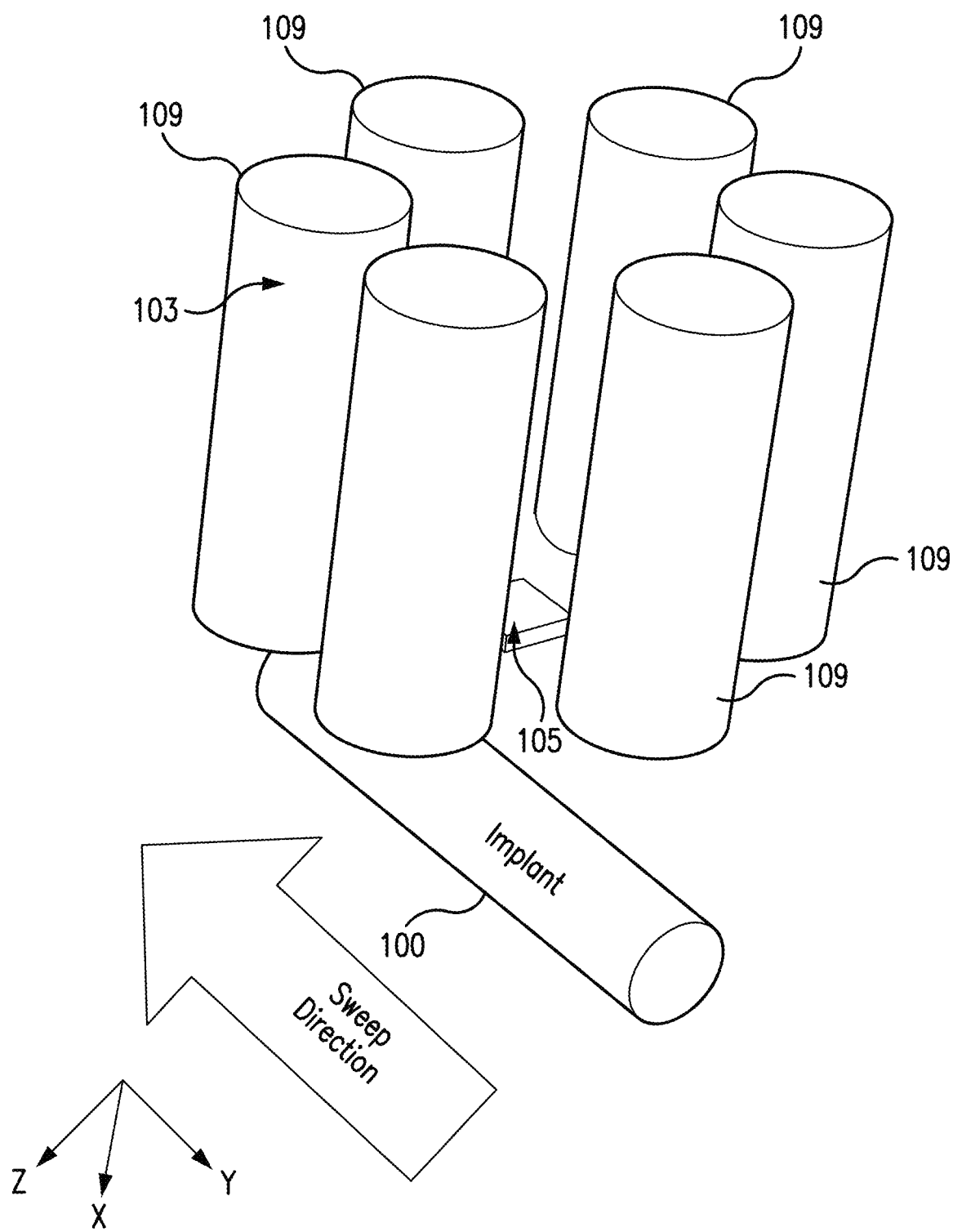
FIGS. 12A and 12B illustrate movement of the implant finder along a longitudinal axis of an implant and a magnitude of changes to a magnetic field during the movement for different distances between the sensor and implant, respectively, embodying aspects of the present invention.
Figure 12B:
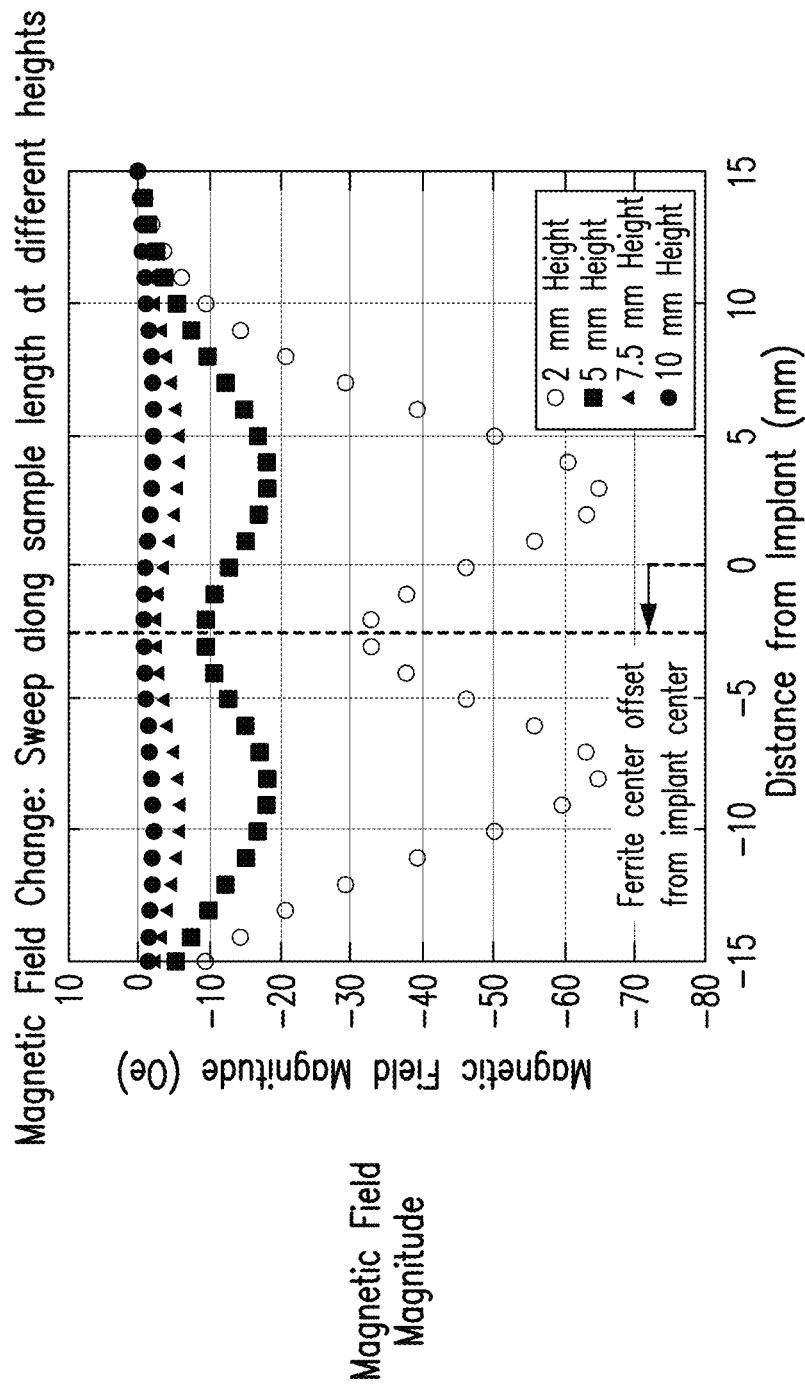

FIG. 12B illustrates detected magnetic field changes as the implant finder 101 is moved along the longitudinal axis of the implant 100 for implants 100 at different heights of the sensor 105 of the implant finder 101 relative to the implant 100. As shown in FIG. 12B, the magnitudes of the detected magnetic field change at the bimodal peaks increase as the height decreases. Accordingly, the implant finder 101 (e.g., the computer 106 of the implant finder 101) may be configured to use the magnitude of the detected magnetic field change at one or more of the bimodal peaks (e.g., the local maxima in the detected magnetic field change during movement of the sensor 105 along the longitudinal axis of the implant 100) to determine the depth of the implant 100 in the tissue 150. In some aspects, the implant finder 101 may additionally or alternatively use the magnitude of the magnetic field change at the midline of the implant 101 to determine the depth of the implant 100 in the tissue 150.

In some aspects, as shown in FIG. 9D, the magnitudes of the magnetic field change at the bimodal peaks may be equal (or approximately equal such as, for example and without limitation, within 2 or 3 oersted (Oe))) for an implant 100 that is not tilted relative to the skin surface and has a longitudinal axis that runs parallel to the skin surface 154. In some aspects, as shown in FIGS. 10D and 14C, the magnitudes of the magnetic field change at the bimodal peaks may be different for an implant 100 having a longitudinal axis that is not parallel to the skin surface 154 (e.g., for a downward-tilted implant 100). In some aspects, the implant finder 101 (e.g., the computer 106 of the implant finder 101)

may determine an orientation of the implant 100 using the magnitudes of the magnetic field change at the bimodal peaks. In some aspects, determining the orientation may include calculating a difference between the magnitudes of the magnetic field change at the bimodal peaks and calculating an angle of the implant 100 relative to the skin surface 154 based on the calculated difference. In some aspects, determining the orientation of the implant 100 may additionally or alternatively include using the magnitudes to of the magnetic field change at the bimodal peaks to calculate depths of the edges of the magnetic material 124 (and/or of the edges of the implant 100).

In some aspects, the implant finder 101 (e.g., the computer 106 of the implant finder 101) may be configured to cause the user interface 127 (e.g., the display 129 of the user interface 127) to provide information indicative of a location and/or orientation of the implant 100. In some aspects, the information indicative of the location and/or orientation of the implant 100 may include information indicative of a midline of the implant 100, one or more edges of the magnetic material 124, one or more edges of the implant 100, a center of the magnetic material 124, a center of the implant 100, a depth of the implant 100 in the tissue 150, an orientation of the implant 100, and/or an incision location for removal of the implant 100. In some aspects, the information indicative of the orientation of the implant 100 may include an indication of the angle of the implant 100, depths of the edges of the magnetic material 124, and/or depths of the edges of the implant 100. In some aspects, the information indicative of the location and/or orientation of the implant 100 may include the implant image 704 (e.g., as shown in FIGS. 7B-7F). In some aspects, the information indicative of the location and/or orientation of the implant 100 may include one or more plots of the magnetic field changes during the movement/sweeps of the implant finder 101 (e.g., the plots shown in FIGS. 9B, 9D, 10B, 10D, 13B-13E, 14B, 14C). In some aspects, the plots of may show one or more peaks in the magnetic field change (e.g., depending on whether the movement is across, along, or diagonal to the longitudinal axis of the implant 100).

Figure 9E:
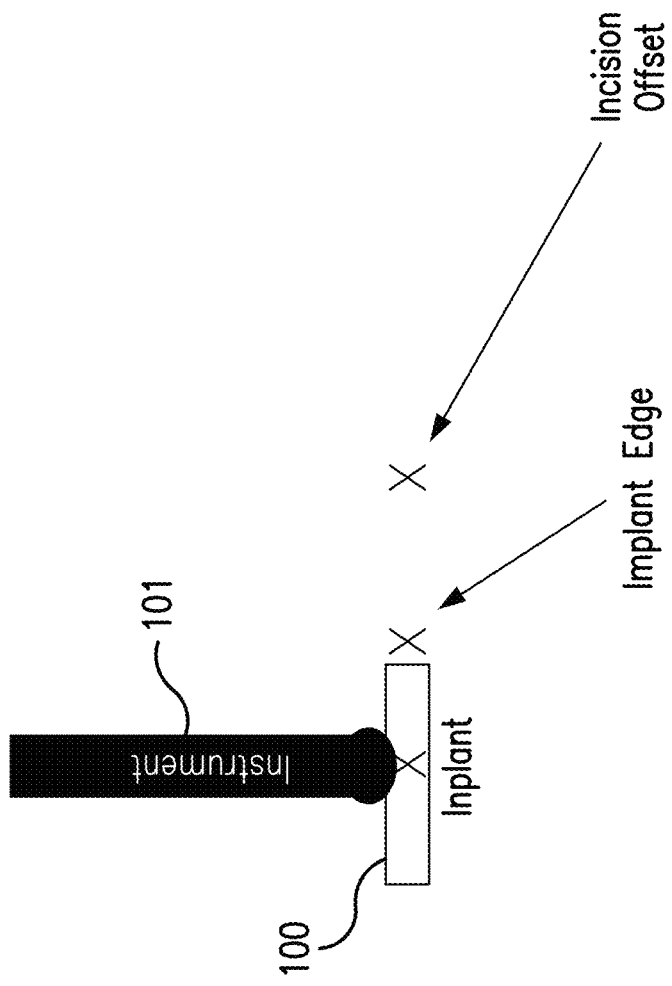
FIG. 9E illustrates an identified implant edge and marked incision location embodying aspects of the present invention.
Figure 10E:
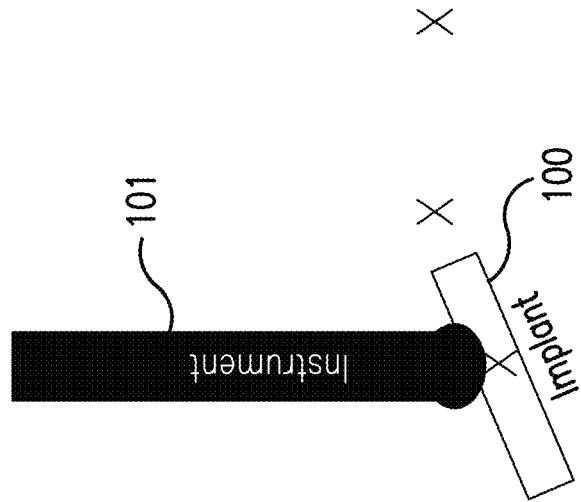
FIG. 10E illustrates an identified implant edge and marked incision location embodying aspects of the present invention.
Figure 10E:
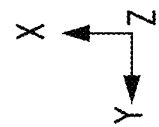

In some aspects, as shown in FIGS. 9E and 10E, the first process for locating the implant 100 may include a third step of marking a location for an incision to remove the implant 100. In some aspects, the incision location may be marked using the incision marking tool 113 of the implant finder 101 (e.g., when the sensor 105 of the implant finder 101 is positioned over the center of the implant 100, over the center of the magnetic material 101 of the implant 100, and/or with the edges of the magnetic field generator 103 positioned over the edges of the magnetic material 124 of the implant 100).

Figure 13A:
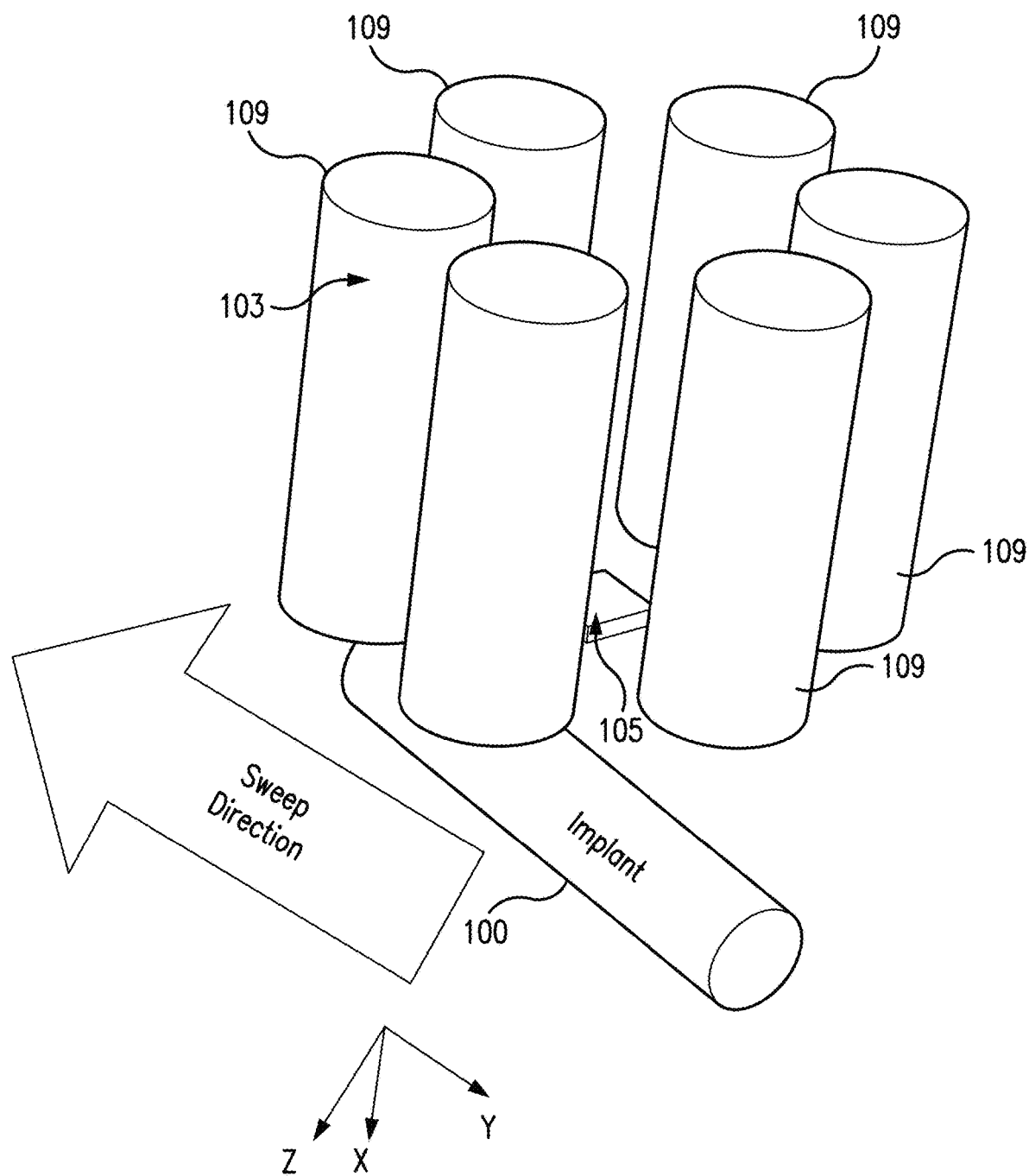
FIGS. 13A and 13B illustrate movement of the implant finder in a diagonal direction relative to a longitudinal axis of an implant and a magnitude of changes to a magnetic field during the movement, respectively, embodying aspects of the present invention.
Figure 13B:
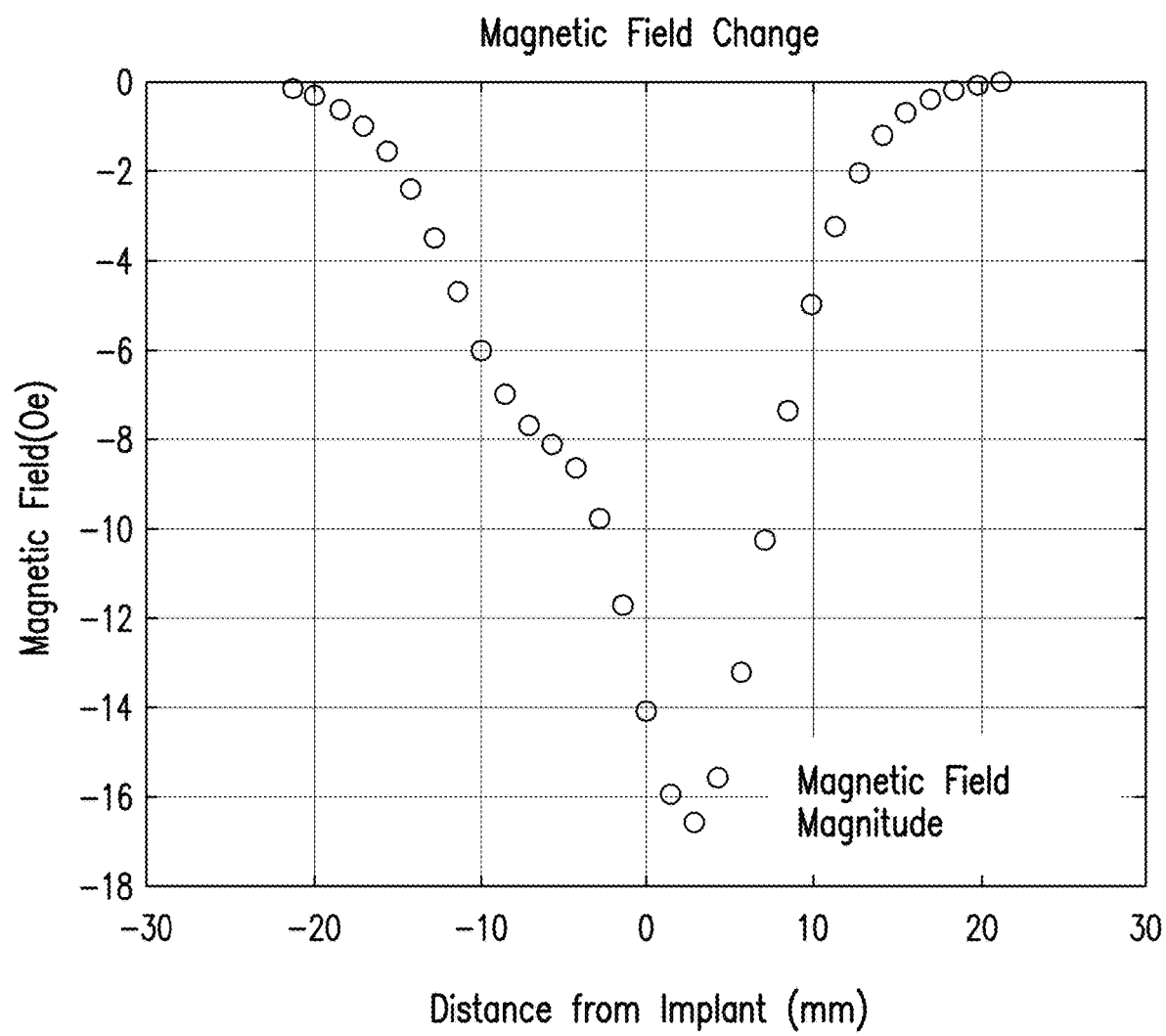
Figures 13C, 13D, 13E:
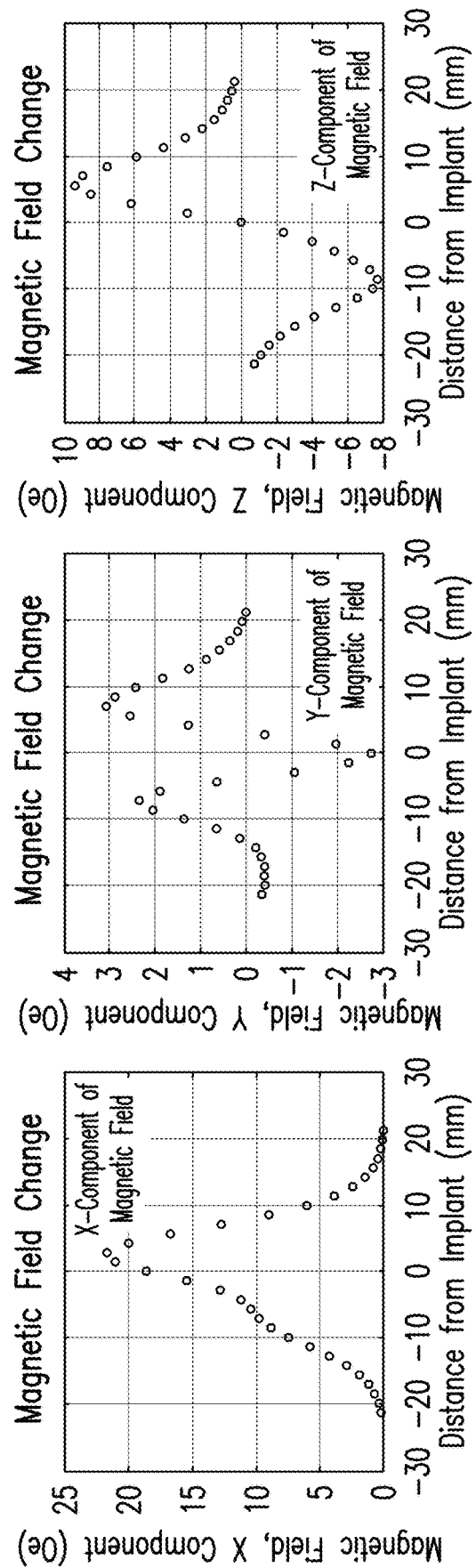
FIGS. 13C-13E illustrate X-, Y-, and Z-components, respectively, of the magnetic field change as the implant finder is moved in the diagonal direction relative to the longitudinal axis of the implant embodying aspects of the present invention.

In some aspects, as shown in FIG. 13A, the implant finder 101 may be moved in a diagonal direction (e.g., at a 45 degree angle or at a smaller angle such as, for example and without limitation, a 10, 15, 20, 25, or 30 degree angle) relative to a longitudinal axis of the implant 100 (e.g., when a user is attempting to locate the implant 100 and/or by accident when the user is attempting to move the implant finder 101 along the longitudinal axis). FIG. 13B illustrates detected magnetic field changes as the implant finder 101 is moved diagonal to the longitudinal axis of the implant 100. FIGS. 13C-13E illustrate X-, Y-, and Z-components of the magnetic field change as the implant finder 101 is moved diagonal to the longitudinal axis of the implant 100. In some aspects, the location of the greatest magnitude of the magnetic field change may be used to determine the midline of the implant 100. In some aspects, the movement/scan direction of the implant finder 101 may be changed until the orientation of the implant 100 (e.g., the longitudinal axis of the implant 100) is found.

In some aspects, the implant finder 101 (e.g., a computer 106 of the implant finder 101) may be configured to control the user interface 127 (e.g., the display 129) to output information indicative of the sensor signal generated by the sensor 105 (and therefore indicative of the detected changes in the magnetic field caused by the magnetic material 124 of the implant 100). In some aspects, a user (e.g., clinician) may use the information indicative of the sensor signal live to map out an approximate location of the implant 100.

Figure 15A:
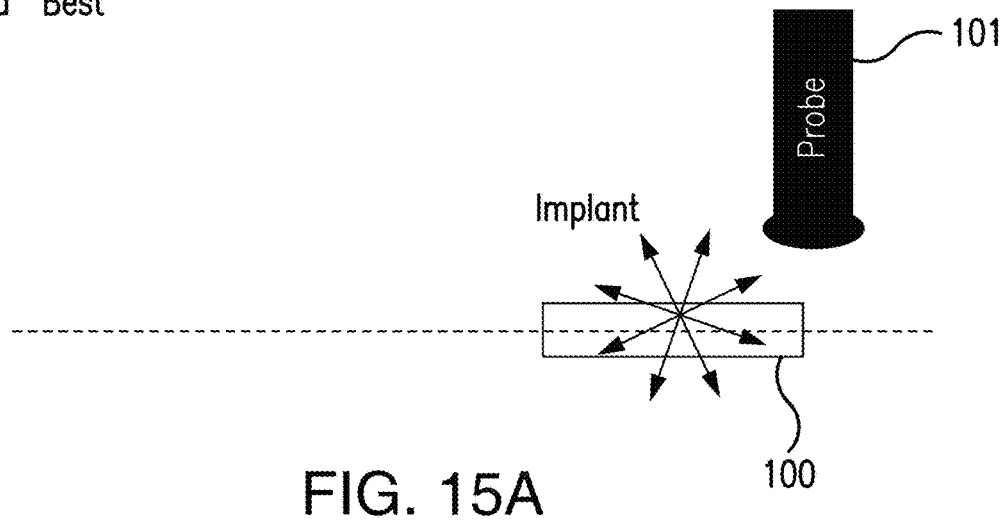
FIGS. 15A-15C illustrate movement of the implant finder to identify an orientation of an implant, movement of the implant finder along a longitudinal axis of the implant, and an identified implant edge and marked incision location, respectively, embodying aspects of the present invention.

In some aspects, a second process may be used to locate the implant 100. In some aspects, the second process may be used if the first process (described above with respect to FIGS. 9A-10E) does not expose the double/bimodal peak pattern present when the implant finder 101 is moved along the longitudinal axis of the implant 100. In some aspects, the second process may include a first step of finding a "best" orientation of the longitudinal axis of the implant 100. In some aspects, as shown in FIG. 15A, the first step may include moving the implant finder 101 at different angles (e.g., at incremental 15 degree angles) until double/bimodal peak pattern is identified.

Figure 15B:
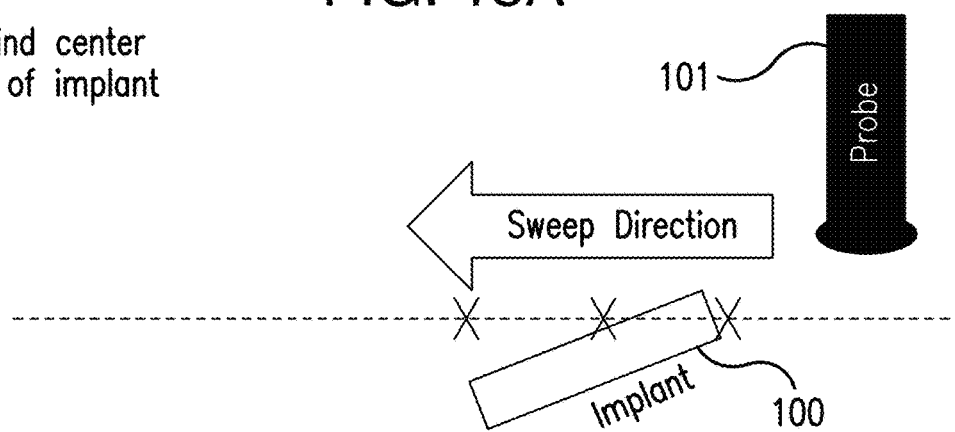

In some aspects, as shown in FIG. 15B, the second process may include a second step identifying a center of the magnetic material 124 of the implant 100. In some aspects, the second step may include moving the implant finder 101 along the longitudinal axis identified in the first step. In some aspects, as shown in FIGS. 9D, 10D, and 14C, the detected changes in the magnetic field as the implant finder 101 is moved along the longitudinal axis of the implant 100 may include bimodal peaks (e.g., local maxima) at the locations of the edges of the magnetic material 124 of the implant 100. In some aspects, the center of the magnetic material 124 may be identified by finding a local minimum in the magnetic field change between the bimodal peaks in the magnetic field changes. In some aspects, the computer 106 of the implant finder 101 may be configured to determine a derivative of the detected changes in the magnetic field, and the computer 106 may be configured to determine the center of the magnetic material 124 of the implant 100 (and the locations of local minimum between the bimodal peaks in the magnetic field changes) based on a location where the derivative of the changes in the magnetic field equals zero during movement of the sensor 105 along a longitudinal axis of the implant 100. In some aspects, the implant finder 101 (e.g., the computer 106 of the implant finder 101) may be configured to cause the user interface 127 to provide an indication of the center of the magnetic material 124. In some aspects, the indication of the center of the magnetic material 124 may include a plot of the magnetic field changes during the sweep and/or a visual (e.g., flashing light), aural (e.g., beep), or vibratory indication when a derivate of the magnitude of the magnetic field change is zero between the bimodal peaks).

In some aspects, the second process may include a third step in which the implant finder 101 (e.g., the computer 106 of the implant finder 101) calculates the depth and/or orientation (e.g., downward angulation) of the implant 100. In some aspects, the implant finder 101 may calculate the depth and/or orientation of the implant 100 using the magnitudes of the magnetic field change at the bimodal peaks and/or a difference between the magnitudes of the magnetic field change at the bimodal peaks. In some aspects, the implant finder 101 may calculate the depth and/or orientation of the implant 100 in response to a user input (e.g., button press) received via the user input 135 of the user interface 127. In some aspects, the implant finder 101 may cause the user interface 127 (e.g., the display 129 of the user interface 127) to provide the calculated depth and/or orientation of the implant 100 to a user (e.g., a clinician).

In some aspects, the implant finder 101 (e.g., the computer 106 of the implant finder 101) may calculate the depth and/or orientation (e.g., downward angulation) of the implant 100 using a data library to map the sensor signal generated by the sensor 105 during one or more movements/sweeps of the implant finder 101 to a depth and/or orientation. In some aspects, the library may include sensor signal curves characteristic of particular orientations of the implant 100. In some aspects, the characteristic curves may have been identified through experimentation. In some aspects, the implant finder 101 (e.g., the computer 106 of the implant finder 101) may compare the sensor signal generated by the sensor 105 during one or more movements/sweeps of the implant finder 101 to the characteristic curves. In some aspects, the implant finder 101 may determine that the implant 100 has approximately the implant orientation (e.g., in-plane and/or out-of-plane angulation) associated with the characteristic curve to which the generated sensor signal is most similar. In some aspects, the implant finder 101 (e.g., the computer 106 of the implant finder 101) may calculate the depth (or an estimated depth range) using the magnitude of the sensor signal generated during the movement/sweep (e.g., at one or more peaks thereof).

In some aspects, if the implant finder 101 determines that the sensor signal generated by the sensor 105 during movement of the implant finder 101 is indicative of in-plane angulation (e.g., indicative that the movement/sweep direction is diagonal with respect to the longitudinal axis of the implant 100), the third step of the second process may include the implant finder 101 (e.g., the computer 106 of the implant finder 101) determining suggested modification to the movement/sweep direction. In some aspects, the suggested modification may be a particular angle with respect to set direction (e.g., the long axis of the arm) or an angle change (e.g., +5° or −15° with respect to the current/most-recent movement direction. In some aspects, the implant finder 101 may cause the user interface 127 (e.g., the display 129 of the user interface 127) to provide the suggested modification to the movement/sweep direction to a user. In some aspects, the movement/sweep direction may be adjusted until the generated sensor signal looks as close as the baseline as possible. In some aspects, if one peak is still present in the generated sensor signal, the one peak is most likely due to out-of-plane angulation, which cannot be corrected by adjusting sweep direction.

Figure 15C:
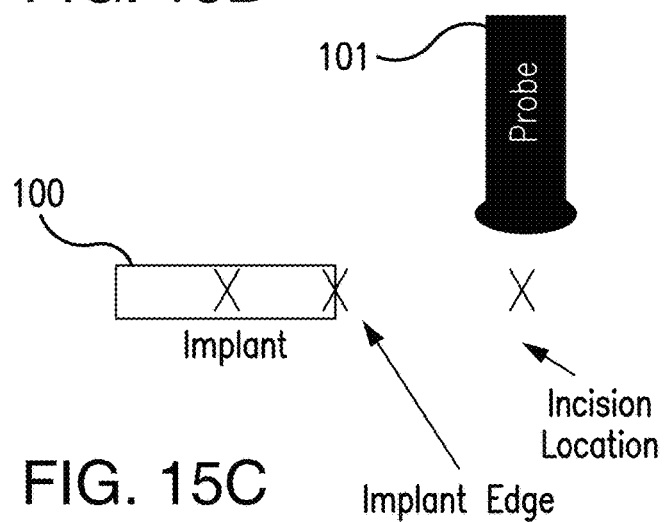

In some aspects, as shown in FIG. 15C, the third step of the second process may include marking an implant edge (e.g., using fittings on the outer edge of the magnetic field generator 103) and/or marking an incision location (e.g., using the incision marking tool 113).

Figure 16A:
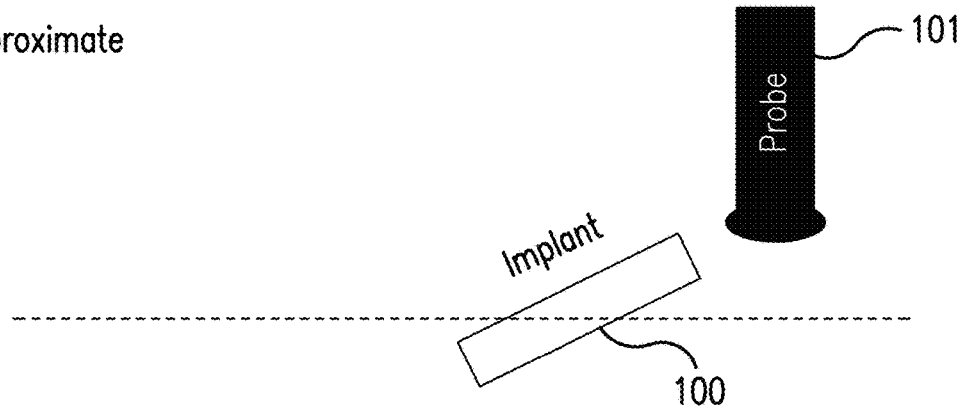
FIGS. 16A-16C illustrate identification of an approximate location of an implant, markings indicating a course for movement of an implant finder, and an identification of implant edge and incision coordinates, respectively, embodying aspects of the present invention.

In some aspects, a third process may be used to locate the implant 100. In some aspects, the third process may include a first step of finding an approximate location of the longitudinal axis of the implant 100. In some aspects, as shown in FIG. 16A, the first step may include moving the implant finder 101 along the skin surface 154 and searching for any signal. In some aspects, the implant 100 may be located in the region where the signal is found.

Figure 16B:
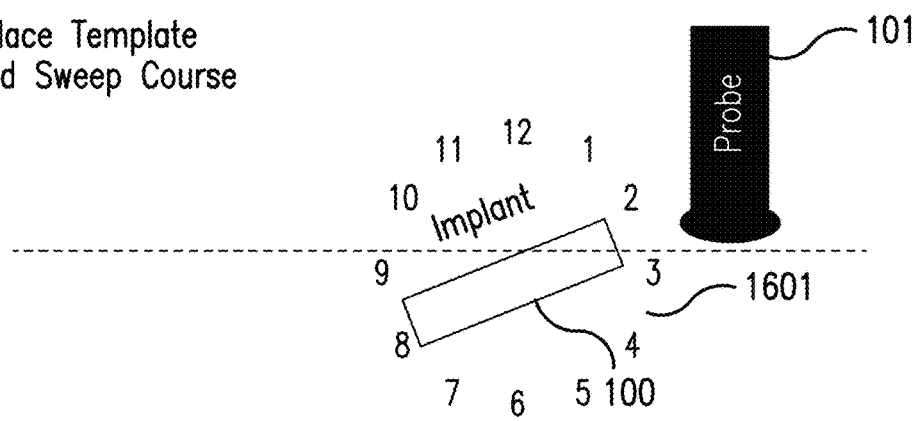

In some aspects, as shown in FIG. 16B, the third process may include a second step in which a template 1601 (e.g., a template sticker) is placed over the region where the signal was found. In some aspects, as shown in FIG. 16B, the template 1601 may include markings (e.g., numbers) that act as way-points identifying a course of movement/sweeping for the implant finder 101. For example, in some aspects, the template 1601 may identify a course, for example and without limitation, from waypoints 9 to 3, 4 to 10, 11 to 5, 6 to 12, 1 to 7, and 8 to 2. In some aspects, the implant finder 101 (e.g., the computer 106 of the implant finder 101) may cause the user interface 127 (e.g., the display 129) to provide instructions for the course of movement/sweeping of the implant finder 101 using the template 1601. In some aspects, the second step of the third process may include moving the implant finder 101 along the course identified by the template 1601. In some aspects, the second step of the third process may end with movement of the implant finder 101 to a final position on top of the template 1601.

In some aspects, the third process may include a third step in which the implant finder 101 (e.g., the computer 106 of the implant finder 101) calculates the depth and/or orientation (e.g., in-plane angulation and/or out-of-plane angulation) of the implant 100. In some aspects, the implant finder 101 may calculate the depth and/or orientation of the implant 100 using the sensor signal generated by the sensor 105, which is indicative of magnetic field changes caused by the magnetic material 124 of the implant 100, as the implant finder 101 is moved along the course identified by the template 1601. In some aspects, the implant finder 101 (e.g., the computer 106 of the implant finder 101) may calculate the depth and/or orientation of the implant 100 using the data library to map the sensor signal generated by the sensor 105 as the implant finder 101 is moved along the course identified by the template 1601 to a depth and/or orientation. In some aspects, the implant finder 101 may calculate the depth and/or orientation of the implant 100 in response to a user input (e.g., button press) received via the user input 135 of the user interface 127. In some aspects, the implant finder 101 may cause the user interface 127 (e.g., the display 129 of the user interface 127) to provide the calculated depth and/or orientation of the implant 100 to a user (e.g., a clinician).

Figure 16C:
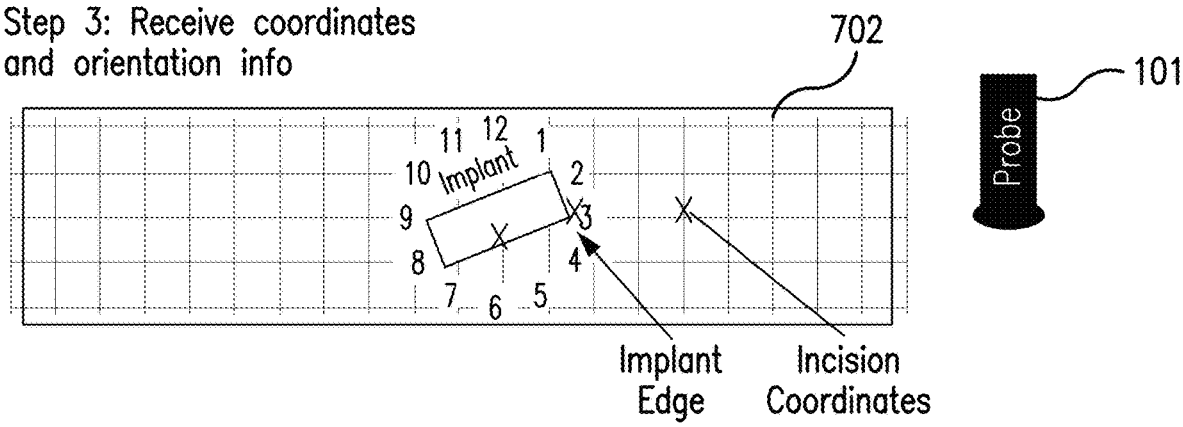

In some aspects, as shown in FIG. 16C, the implant finder 101 may display an implant image 704 and/or a template image 1603 on the screen 702 of the display 129. In some aspects, as shown in FIG. 16C, the location of the implant image 704 relative to the template image 1603 on the screen 704 of the display 129 may correspond to a detected location of the implant 100 relative to the template 1601. In some aspects, as shown in FIG. 16C, the implant image 704 may have an orientation that corresponds to the calculated orientation of the implant 100. In some aspects, the implant image 704 may show in-plane angulation and/or out-of-plane (e.g., downward) angulation of the calculated orientation. In some aspects, the implant image 704 may additionally or alternatively show the calculated depth.

In some aspects, the third step of the third process may additionally or alternatively include the implant finder 101 (e.g., the computer 106 of the implant finder 101) calculating one or more edges of the implant 100, a center of the implant 100, and/or an incision location. In some aspects, the implant finder 101 may calculate the one or more implant edges, the implant center, and/or the incision location using the sensor signal generated by the sensor 105, which is indicative of magnetic field changes caused by the magnetic material 124 of the implant 100, as the implant finder 101 is moved along the course identified by the template 1601. In some aspects, the implant finder 101 may calculate the one or more implant edges and/or the incision location using the calculated depth and/or orientation of the implant 100. In some aspects, the implant finder 101 may cause the user interface 127 (e.g., the display 129 of the user interface 127) to provide the calculated one or more implant edges, implant center, and/or incision location to a user (e.g., a clinician). In some aspects, as shown in FIG. 16C, the implant finder 101 may display the calculated one or more implant edges, implant center, and/or incision location on the screen 702 of the display 129 as coordinates.

Figure 17:
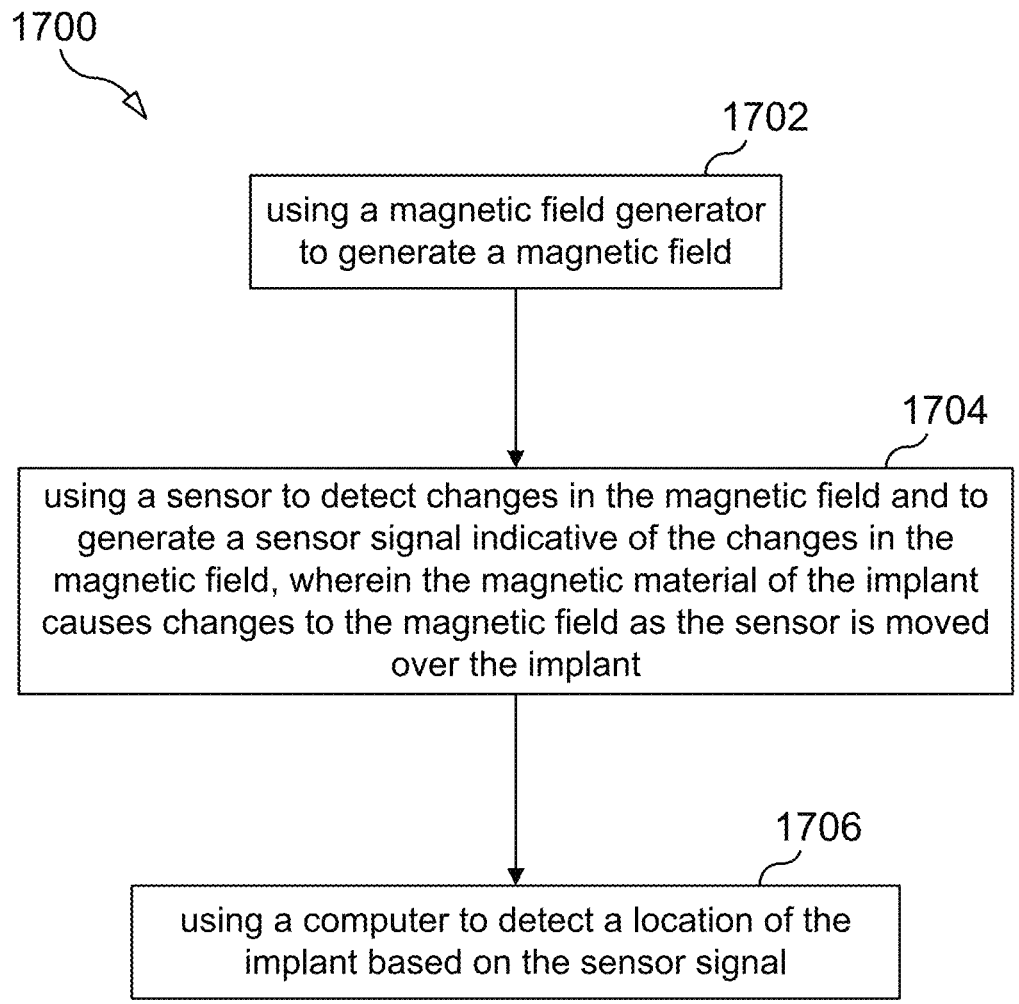
FIG. 17 is a flowchart illustrating a non-limiting example of a process for locating an implant including magnetic material embodying aspects of the present invention.

FIG. 17 is a flow chart illustrating a process 1700 for locating an implant 100 including magnetic material 124 according to some aspects. In some aspects, the process 1700 may include a step 1702 of using a magnetic field generator 103 to generate a magnetic field. In some aspects, the magnetic field generator 103 may include one or more magnets 109. In some aspects, the magnetic field generator 103 may include a cylindrical magnet 109 (e.g., a hollow cylindrical magnet). In some alternative aspects, the magnetic field generator 103 may include two or more magnets 109 (e.g., four or six magnets). In some aspects, the magnetic field generator 103 may include a housing 107 configured to hold the two or more magnets 109. In some aspects, the magnetic field generated by the magnetic field generator 103 may be a substantially uniform magnetic field.

In some aspects, the process 1700 may include a step 1704 of using a sensor 105 to detect changes in the magnetic field and to generate a sensor signal indicative of the changes in the magnetic field. In some aspects, the magnetic material 124 of the implant 100 may cause changes to the magnetic field as the sensor 105 is moved over the implant 100. In some aspects, the magnetic field may be substantially symmetric about a longitudinal axis at the center of the magnetic field generator 103. In some aspects, the sensor 105 may be located along or offset from the longitudinal axis at the center of the magnetic field generator 103.

In some aspects, the process 1700 may include a step 1706 of using a computer 106 to detect a location of the implant 100 based on the sensor signal. In some aspects, the step 1706 may include the computer 106 causing the user interface 127 to provide an output indicative of the sensor signal. In some aspects, the user (e.g., a clinician) may use the output sensor signal to detect the location of the implant 100. In some aspects, the step 1706 may include the computer 106 causing the user interface 127 to provide indications of when a derivative of the changes in the magnetic field equals zero during movement of the sensor 105 across a longitudinal axis of the implant 100. In some aspects, the indications of the derivative of the changes in the magnetic field equaling zero during movement of the sensor 105 across the longitudinal axis of the implant 100 may be indicative of the location of the implant 100.

In some aspects, the step 1706 may additionally or alternatively include the computer 106 determining edges of the magnetic material 124 of the implant 100 based on locations of bimodal peaks in the changes in the magnetic field during movement of the sensor 105 along a longitudinal axis of the implant 100. In some aspects, the computer 106 may determine edges of the implant 100 based on the determined edges of the magnetic material 124 of the implant 100 and one of more offsets between edges of the implant 100 and edges of the magnetic material 124 of the implant 100. In some aspects, the computer 106 may be configured to calculate a derivative of the changes in the magnetic field and to use the calculated derivative to detect the location of the implant 100. In some aspects, the computer 106 may be configured to determine edges of the magnetic material 124 of the implant 100 based on locations where the derivative of the changes in the magnetic field equals zero during movement of the sensor 105 along a longitudinal axis of the implant 100.

In some aspects, the step 1706 may additionally or alternatively include the computer 106 determining a midline of the implant 100. In some aspects, the computer 106 may be configured to determine the midline based on a location where the derivative of the changes in the magnetic field equals zero during movement of the sensor 105 across a longitudinal axis of the implant 100.

In some aspects, the process 1700 may include a step in which the computer 106 determines a depth of the implant 100 based on a magnitude of the change in the magnetic field at the bimodal peaks in the changes in the magnetic field during the movement of the sensor 105 along the longitudinal axis of the implant 100. In some aspects, the computer 106 may determine a depth of the implant 100 based on magnitudes of the changes in the magnetic field at the locations where the derivative of the changes in the magnetic field equals zero during the movement of the sensor 105 along the longitudinal axis of the implant 100.

In some aspects, the process 1700 may additionally or alternatively include a step in which the computer 106 determines an orientation of the implant 100. In some aspects, the computer 106 may determine the orientation based on a difference between magnitudes of the change in the magnetic field at the bimodal peaks in the changes in the magnetic field during the movement of the sensor 105 along the longitudinal axis of the implant 100. In some aspects, the computer 106 may determine an orientation of the implant 100 based on a difference between magnitudes of the changes in the magnetic field at the locations where the derivative of the changes in the magnetic field equals zero during the movement of the sensor 105 along the longitudinal axis of the implant 100.

In some aspects, the process 1700 may additionally or alternatively include computer 106 causing a display 129 to display an indication of the detected location of the implant 100. In some aspects, the indication of the detected location of the implant 100 may include an implant image 704, and a location of the implant image 704 on a screen 702 of the display 129 relative to a point 706 on the screen 702 of the display 129 may correspond to the detected location of the implant 100 relative to the sensor 105. In some aspects, the implant image 704 may have an orientation that corresponds to a detected orientation of the implant 100.

In some aspects in which the implant finder 101 includes the position detector 137 configured to generate a location signal indicative of a location of the sensor 105, the process 1700 may additionally or alternatively include a step in which the computer 106 uses the sensor signal and the location signal (e.g., a motion signal generated by a motion detector of the position detector 137 that is indicative of movement of the sensor 105) to generate a map of sensor signals at different locations of the sensor 105. In some aspects, generating a map of sensor signals at different locations of the sensor may include, for example and without limitation, measuring the sensor signal at each of two or more different locations of the sensor 105 and storing the measured sensor signals along with identifications of the locations at which the sensor signals were measured. In some aspects, generating a map of sensor signals at different locations of the sensor 105 may include generating a visualization of the measured sensor signals at the different locations of the sensor 105.

In some aspects, the process 1700 may include an optional step of removing the implant 100. In some aspects, removing the implant 100 may include making an incision at an identified edge of the implant 100. In some aspects, removing the implant 100 may include grabbing (e.g., using forceps) the implant 100 and pulling the implant 100 out of the body through the incision.

Figure 18:
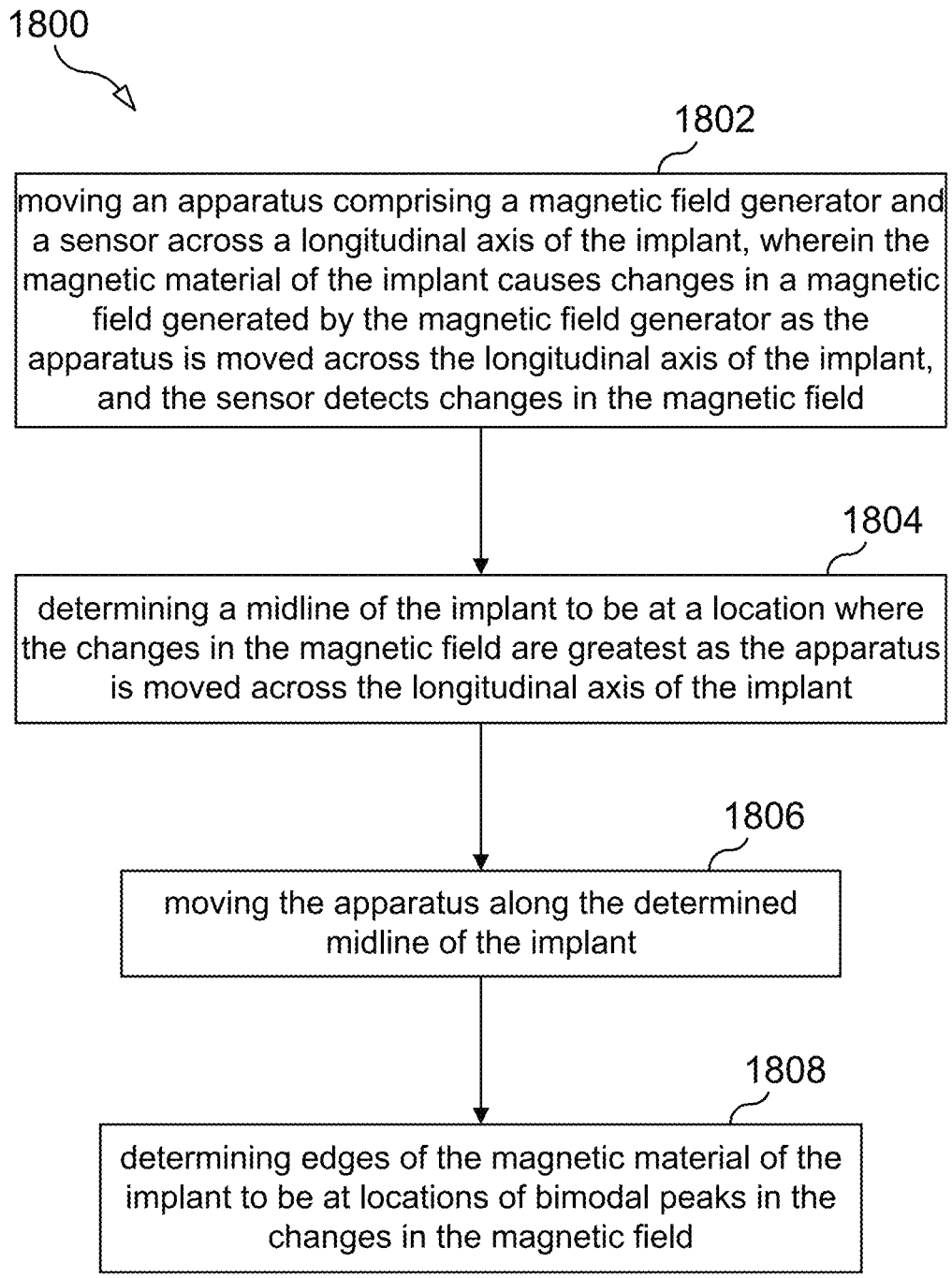
FIG. 18 is a flowchart illustrating a non-limiting example of a process for locating an implant including magnetic material embodying aspects of the present invention.

FIG. 18 is a flow chart illustrating a process 1800 for locating an implant 100 including magnetic material 124 according to some aspects. In some aspects, the process 1800 may include a step 1802 of moving an apparatus (e.g., implant finder 101) including a magnetic field generator 103 and a sensor 105 across a longitudinal axis of the implant 100. In some aspects, the magnetic material 124 of the implant 100 may cause changes in a magnetic field generated by the magnetic field generator 103 as the apparatus is moved across the longitudinal axis of the implant 100, and the sensor 105 may detect changes in the magnetic field. In some aspects, the process 1800 may include a step 1804 of determining a midline of the implant 100 based on a location where the changes in the magnetic field are greatest as the apparatus is moved across the longitudinal axis of the implant 100. In some aspects, the process 1800 may include a step 1806 of moving the apparatus along the determined midline of the implant 100. In some aspects, the process 1800 may include a step 1808 of determining edges of the magnetic material 124 of the implant 100 based on locations of bimodal peaks in the changes in the magnetic field. In some aspects, the process 1800 may include an optional step of using an incision marking tool 113 of the apparatus to mark an incision location for removing the implant 100. In some aspects, the process 1800 may include an optional step of removing the implant 100. In some aspects, removing the implant 100 may include making an incision at the incision location. In some aspects, removing the implant 100 may include grabbing (e.g., using forceps) the implant 100 and pulling the implant 100 out of the body through the incision.

Figure 19:
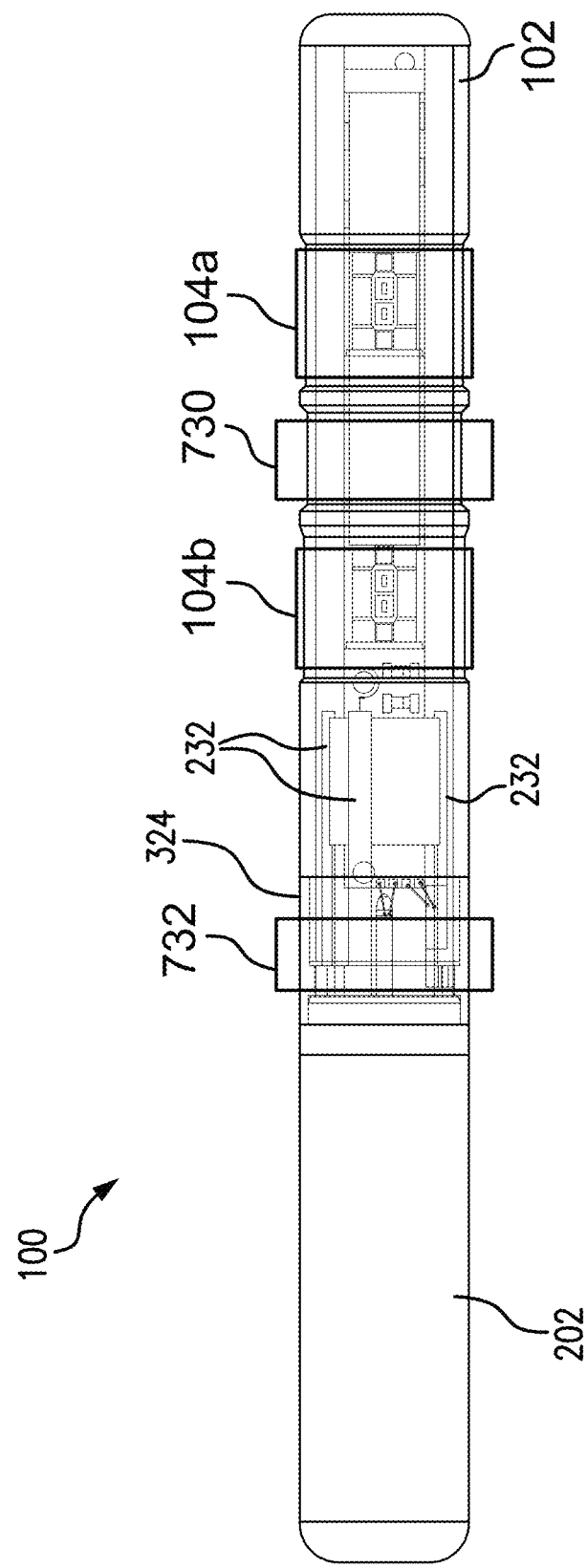
FIG. 19 is a side view illustrating a non-limiting example of an implant embodying aspects of the present invention.

In some aspects, as shown in FIG. 19, the implant 100 may include more than one analyte indicator 104 (e.g., first analyte indicator 104a and second analyte indicator 104b). In some aspects, as shown in FIG. 19, the implant 100 may include a charge storage device 202 (e.g., a battery). In some aspects, the charge storage device 202 may be a battery with a metal housing (e.g., a titanium housing). In some aspects, the charge storage device 202 may be attached to the housing 102. In some aspects, a coupler 324 may attach the housing 102 and the charge storage device 202. In some aspects, the coupler 324 may be between the housing 102 and the charge storage device 202. In some aspects, as shown in FIG. 19, the coupler 324 may include one or more supports 232 (e.g., reinforcement rods, bars, or beams), which may be attached to and/or integral with the coupler 324. In some aspects, the implant 100 may include first and second electrically conductive connectors, which connect positive and negative terminals, of the charge storage device 202 to the circuitry of the implant 100. In some aspects, as shown in FIG. 19, the circuitry of the implant 100 may extend away from the charge storage device 202 along the longitudinal axis of the charge storage device 202. In some aspects, the circuitry of the implant 100 may include the inductor 120, which may include the conductor 122 and the magnetic material 124 in form of a magnetic core. In some aspects, as shown in FIG. 19, the charge storage device 202 may include a first edge at one end of the implant 100 and a second edge adjacent to the coupler 324 and/or housing 102. In some aspects, the second edge of the of the charge storage device 202 may be located in a central region of the implant 100.

In some aspects, the implant 100 may include one or more drug eluting polymer matrices 730 and 732. In some aspects, the one or more drug eluting polymer matrices 730 and 732 may be in or on portions of the exterior surface of the housing 102 of the implant 100). In some aspects, one or more therapeutic agents may be dispersed within the one or more drug eluting polymer matrices 730 and 732. In some aspects, the one or more therapeutic agents may reduce or stop the migration of neutrophils from entering the space in which the implant 100 has been implanted and, thus, reduce or stop the production of hydrogen peroxide and fibrotic encapsulation. Accordingly, in some aspects, the one or more therapeutic agents may reduce deterioration of the one or more analyte indicators 104 (e.g., first analyte indicator 104a and second analyte indicator 104b). In some aspects, the one or more therapeutic agents, which may be dispersed within the one or more drug eluting polymer matrices 730 and 732, may include one or more anti-inflammatory drugs, such as, for example, non-steroidal anti-inflammatory drug (e.g., acetylsalicylic acid (aspirin) and/or isobutylphenylpropanoic acid (ibuprofen)). In some aspects, the one or more therapeutic agents dispersed within the one or more drug eluting polymer matrices 730 and 732 may include one or more glucocorticoids. In some aspects, the one or more therapeutic agents may include one or more of dexamethasone, triamcinolone, betamethasone, methylprednisolone, beclometasone, fludrocortisone, derivatives thereof, and analogs thereof. In some aspects, the one or more therapeutic agents may reduce the production of hydrogen peroxide by neutrophils and macrophages.

Figure 20:
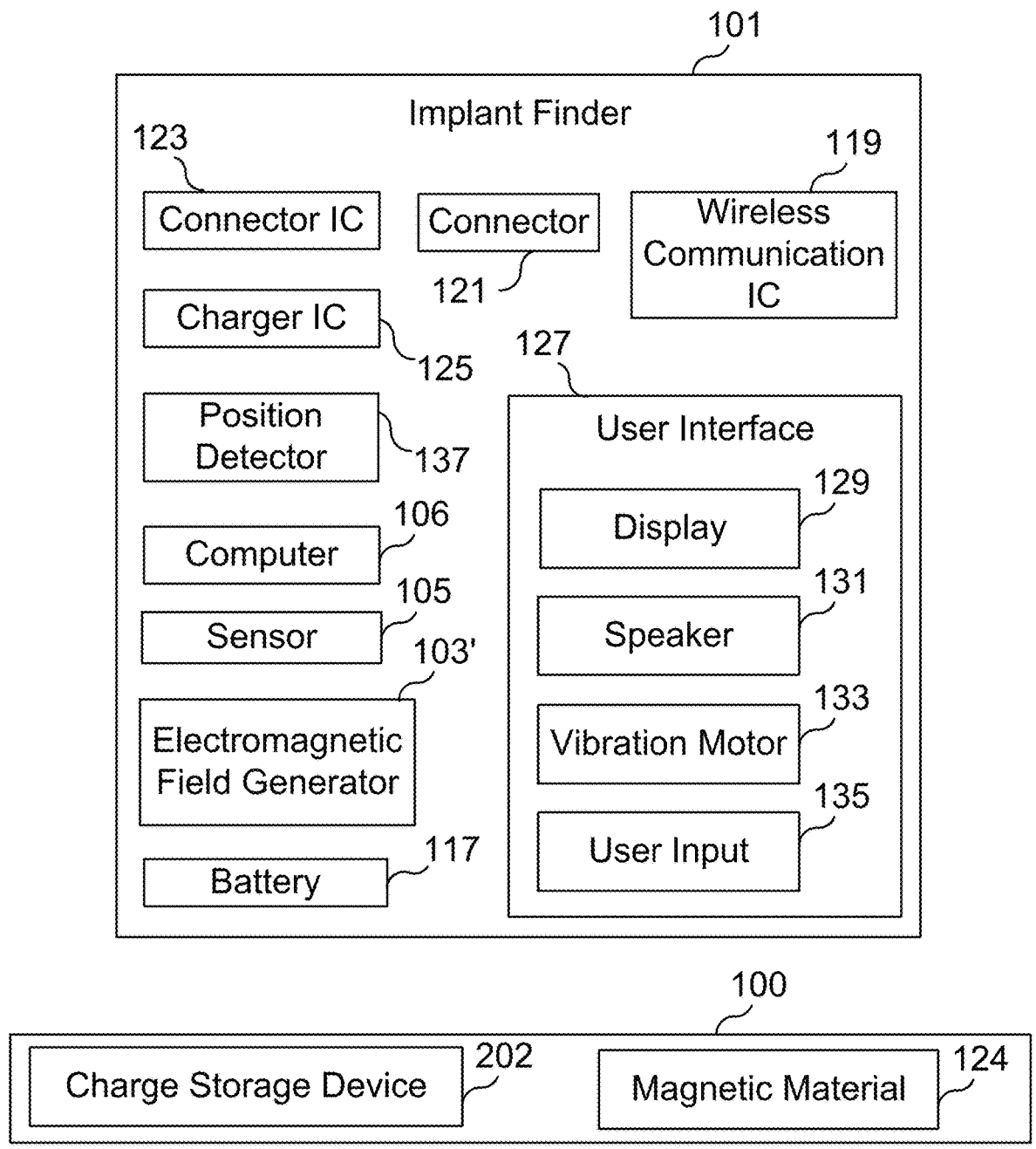
FIG. 20 is a block diagram illustrating a non-limiting example of an implant and an implant finder embodying aspects of the present invention.

In some aspects (e.g., some aspects in which the implant 100 includes a charge storage device 202), as shown in FIG. 20, the magnetic field generator 103 of the implant finder 101 may be an electromagnetic field generator 103' configured to generate an electromagnetic field. In some aspects, the electromagnetic field may include low frequency waves (e.g., very low frequency (VLF) waves). In some aspects, the low frequency waves may have a frequency, for example and without limitation, within a range between 3 kHz and 30 kHz. In some aspects, the low frequency waves may have a frequency, for example and without limitation, within a range between 5 kHz and 15 kHz. In some aspects, the sensor 105 of the implant finder 101 may be configured to detect changes in the electromagnetic field and to generate a sensor signal indicative of the changes in the electromagnetic field. In some aspects, at least the charge storage device 202 of the implant 100 may cause changes to the electromagnetic field as the sensor 105 is moved over the implant 100. In some aspects, the computer 106 of the implant finder 101 may be configured to use the sensor signal to detect a location of the implant 100.

Figure 21A:
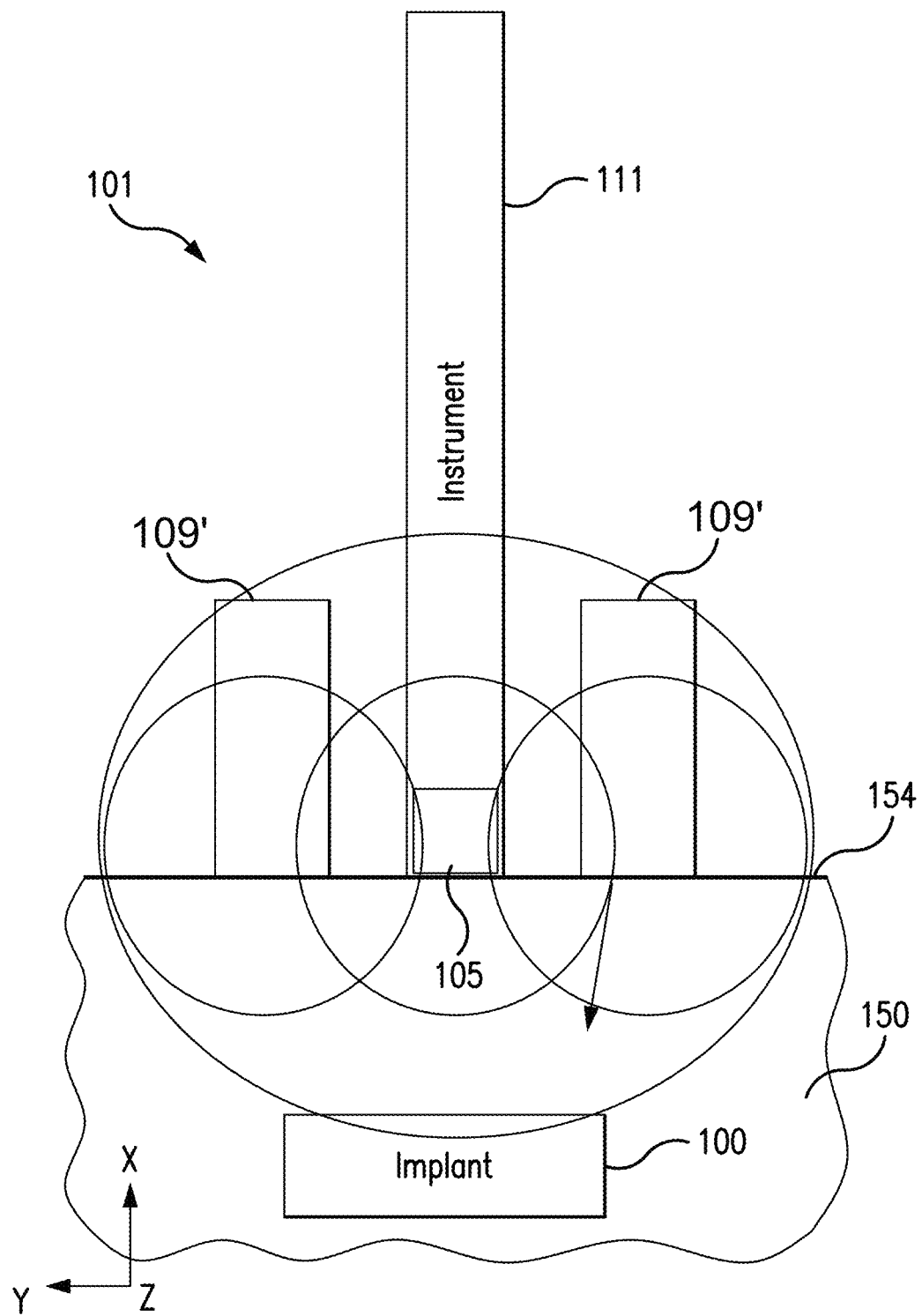
FIG. 21A is a cross-sectional side view illustrating a non-limiting example of an implant and an implant finder embodying aspects of the present invention.
Figure 21B:
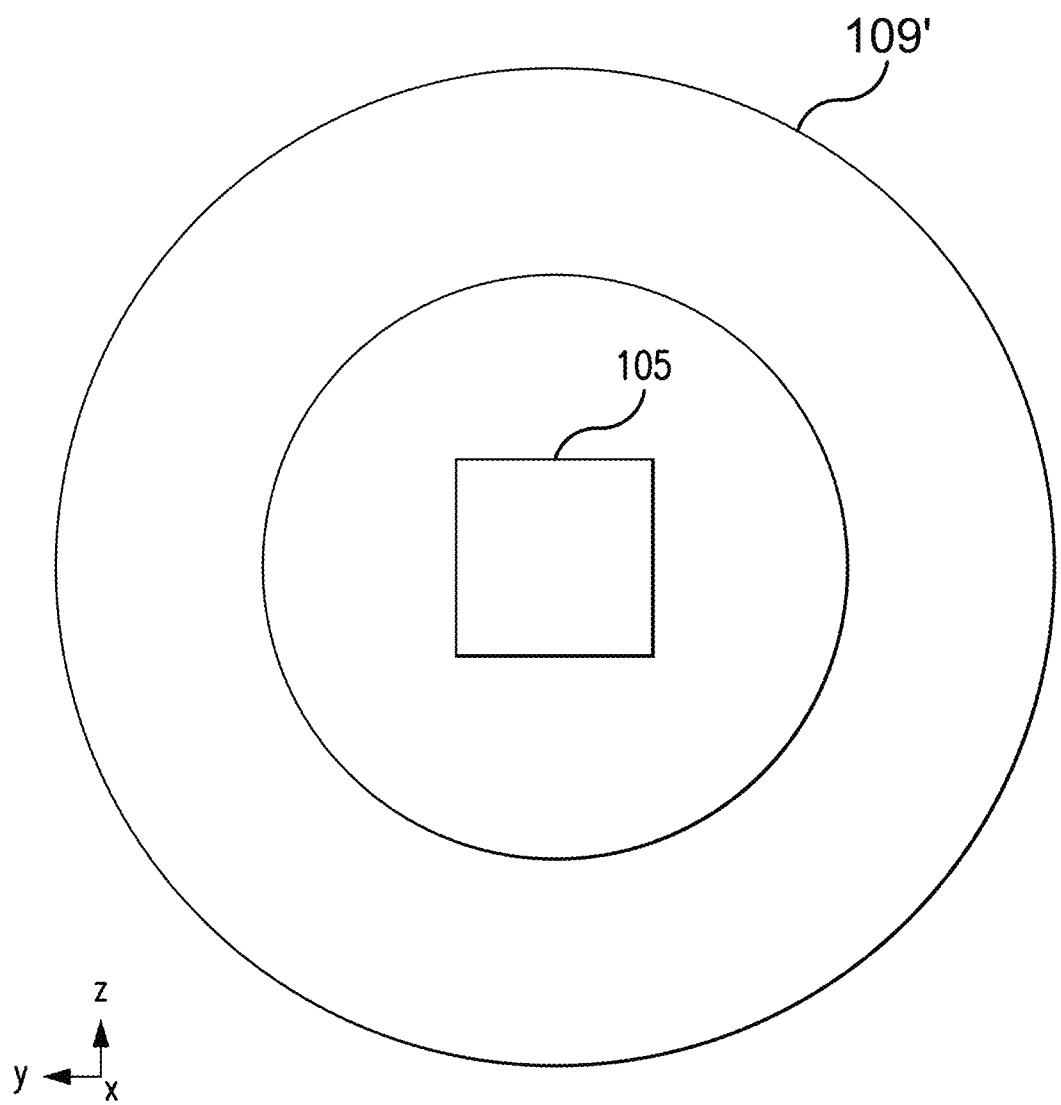
FIG. 21B is a cross-sectional top view illustrating a non-limiting example of an implant finder embodying aspects of the present invention.
Figure 21C:
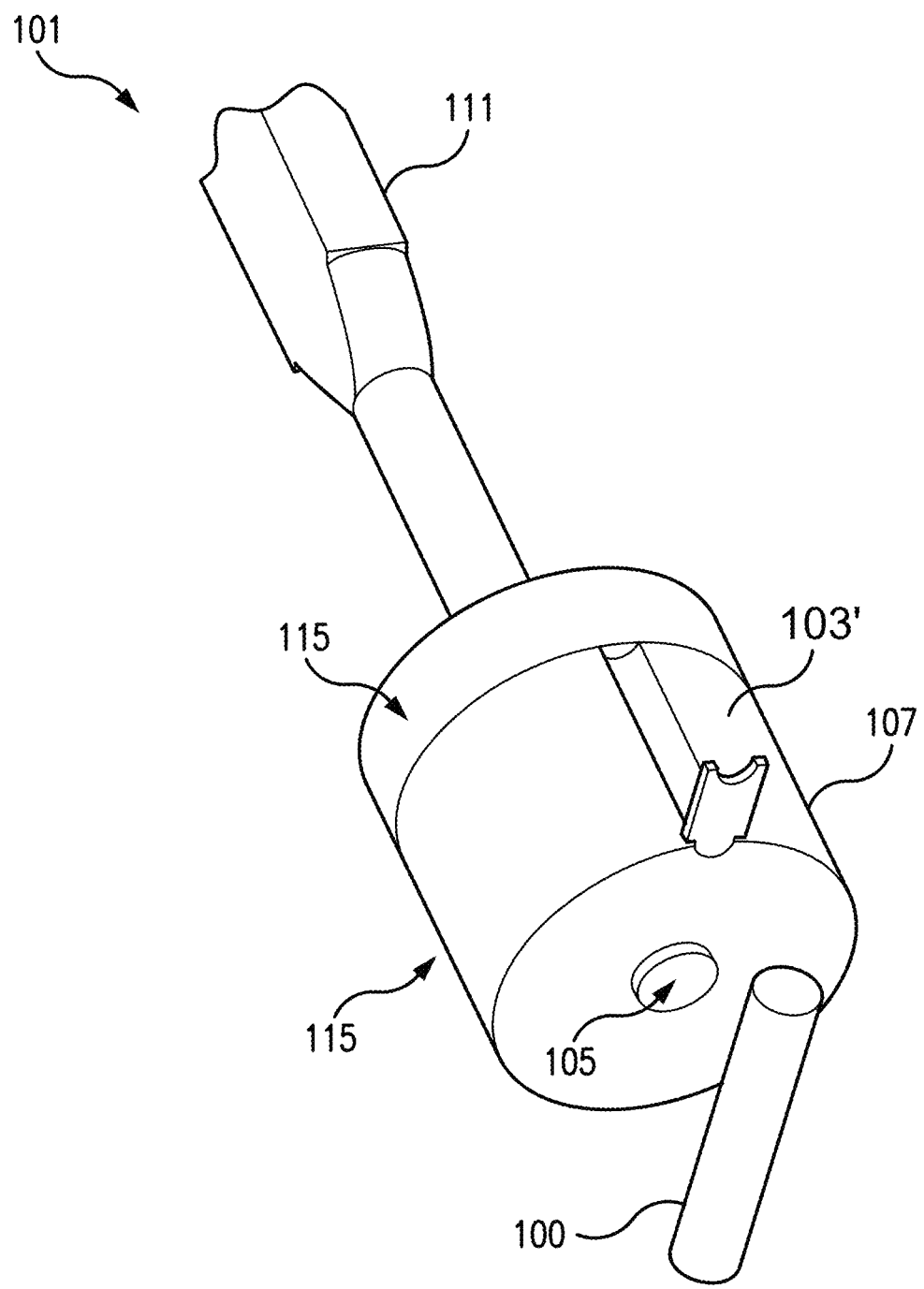
FIG. 21C is a perspective view illustrating a non-limiting example of an implant and an implant finder embodying aspects of the present invention.

In some electromagnetic field aspects, as shown in FIGS. 21A and 21B, the electromagnetic field generator 103' may include one or more electromagnets 109'. In some aspects, the one or more electromagnets 109' may be, for example and without limitation, a coil of wire wound around a magnetic core made from a ferromagnetic or ferrimagnetic material. In some aspects, the electromagnetic field generator 103' may supply an alternating current to the one or more electromagnets 109'. The alternating current may have, for example and without limitation, a frequency within a range of between 3 kHz and 30 kHz or, more particularly, within a range between 5 kHz and 15 kHz. In some aspects, as shown in FIG. 21C, the electromagnetic field generator 103' may include a housing 107, and the housing 107 may be configured to hold the one or more electromagnets 109. However, a housing 107 is not required, and, in some alternative aspects (e.g., some aspects in which the magnetic field generator 103' consists of only a single electromagnet 109'), the electromagnetic field generator 103' may not include a housing 107. In some aspects, as shown in FIGS. 21A and 21B, the sensor 105 may be located on a longitudinal axis at the center of the magnetic field generator 103'. However, this is not required, and, in some alternative aspects, the sensor 105 is not located on a longitudinal axis at the center of the electromagnetic field generator 103'. For example, the sensor 105 may be located adjacent to the electromagnet 109' of the electromagnetic field generator 103' (as opposed to at the center of one or more electromagnets 109' of the electromagnetic field generator 103'). See FIG. 3A.

Figure 22:
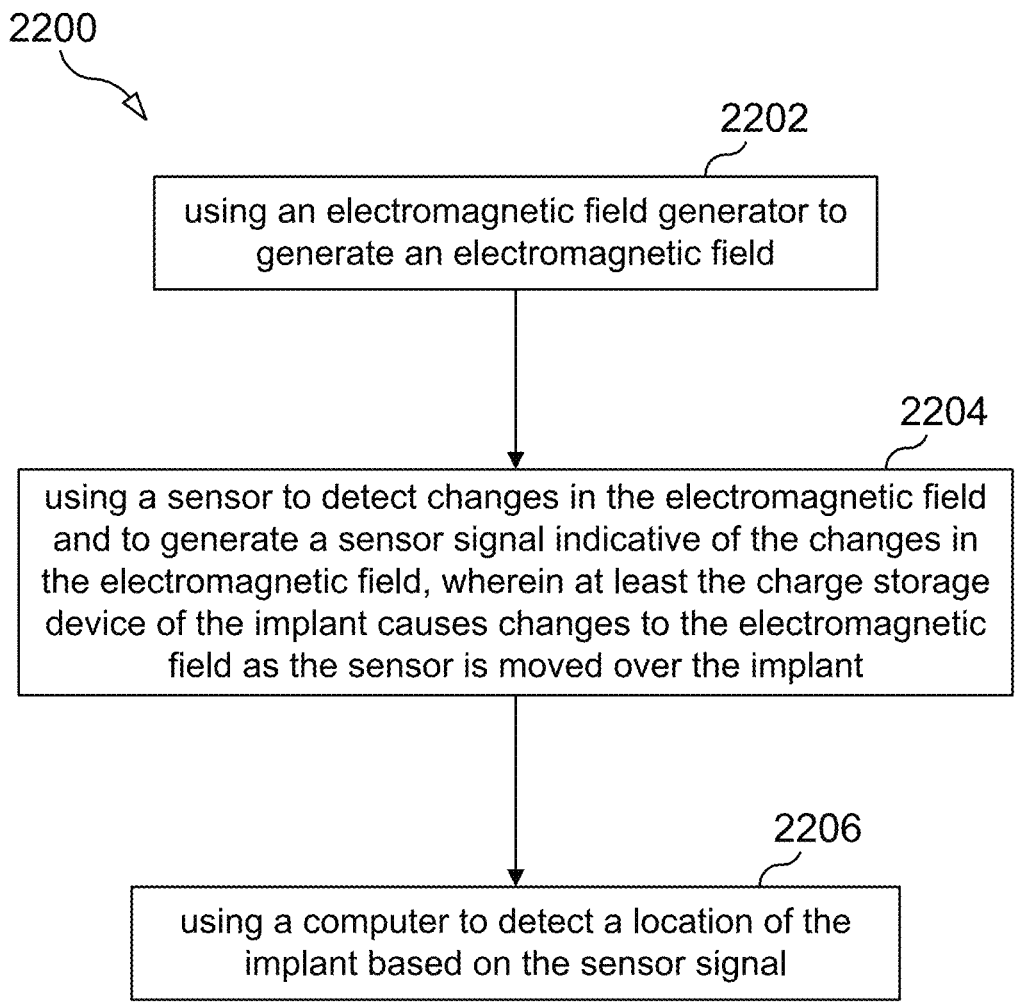
FIG. 22 is a flowchart illustrating a non-limiting example of a process for locating an implant including a charge storage device embodying aspects of the present invention.

FIG. 22 is a flow chart illustrating a process 2200 for locating an implant 100 including a charge storage device 202 according to some aspects. In some aspects, the process 2200 may include a step 2202 of using an electromagnetic field generator 103' to generate an electromagnetic field. In some aspects, the electromagnetic field generator 103' may include one or more electromagnets 109'. In some aspects, the electromagnetic field generator 103' may include a cylindrical electromagnet 109' (e.g., a hollow cylindrical magnet). In some alternative aspects, the electromagnetic field generator 103' may include two or more electromagnets 109' (e.g., four or six electromagnets). In some aspects, the electromagnetic field generator 103' may include a housing 107 configured to hold the one or more electromagnets 109'.

In some aspects, the process 2200 may include a step 2204 of using a sensor 105 to detect changes in the electromagnetic field and to generate a sensor signal indicative of the changes in the electromagnetic field. In some aspects, at least the charge storage device 202 of the implant 100 may cause changes to the electromagnetic field as the sensor 105 is moved over the implant 100. In some aspects, the electromagnetic field may be substantially symmetric about a longitudinal axis at the center of the electromagnetic field generator 103'. In some aspects, the sensor 105 may be located along or offset from the longitudinal axis at the center of the electromagnetic field generator 103'.

In some aspects, the process 2200 may include a step 2206 of using a computer 106 to detect a location of the implant 100 based on the sensor signal. In some aspects, the step 2206 may include the computer 106 causing the user interface 127 to provide an output indicative of the sensor signal. In some aspects, the user (e.g., a clinician) may use the output sensor signal to detect the location of the implant 100. In some aspects, the step 2206 may include the computer 106 causing the user interface 127 to provide indications of when a derivative of the changes in the electromagnetic field equals zero during movement of the sensor 105 across a longitudinal axis of the implant 100. In some aspects, the indications of the derivative of the changes in the electromagnetic field equaling zero during movement of the sensor 105 across the longitudinal axis of the implant 100 may be indicative of the location of the implant 100.

In some aspects, the step 2206 may additionally or alternatively include the computer 106 determining edges of the charge storage device 202 of the implant 100 based on locations of bimodal peaks in the changes in the electromagnetic field during movement of the sensor 105 along a longitudinal axis of the implant 100. In some aspects, the computer 106 may determine one or more edges of the implant 100 based on the determined edges of the charge storage device 202 of the implant 100. In some aspects, the computer 106 may be configured to calculate a derivative of the changes in the electromagnetic field and to use the calculated derivative to detect the location of the implant 100. In some aspects, the computer 106 may be configured to determine edges of the charge storage device 202 of the implant 100 based on locations where the derivative of the changes in the magnetic field equals zero during movement of the sensor 105 along a longitudinal axis of the implant 100.

In some aspects, the magnitude of the bimodal peak in the changes in the electromagnetic field at the first edge of the charge storage device 202, which is at an edge of the implant 100, may be greater than the magnitude of the bimodal peak in the changes in the electromagnetic field at the second edge of the charge storage device 202, which is adjacent to the coupler 324 and/or housing 102. In some aspects, the magnetic material 124 in the housing 102 of the implant 100 may cause the magnitude of the bimodal peak in the changes in the electromagnetic field at the second edge of the charge storage device 202 to be lower than the magnitude of the bimodal peak in the changes in the electromagnetic field at the first edge of the charge storage device 202. In some aspects, the computer 106 may be configured to determine which of the bimodal peaks in the changes in the electromagnetic field has a greater magnitude. In some aspects, the computer 106 may be configured to determine the first edge of charge storage device 202 to be at the location of the bimodal peak having the greater magnitude. In some aspects, the computer 106 may determine one edge of the implant 100 to be at the first edge of the charge storage device 202. In some aspects, the incision location for removing the implant 100 may be at or near the location of the bimodal peak in the changes in the electromagnetic field having the greater magnitude.

In some aspects, the computer 106 may be configured to additionally or alternatively determine a second edge of the implant 100. In some aspects, the computer 106 may determine the determine the second edge of the implant 100 using the location of the second edge of the charge storage device 202 (e.g., the location of the bimodal peak in the changes in the electromagnetic field having the lower magnitude) and an offset between the second edge of the charge storage device 202 and an end of the housing 102. In some aspects, the second edge of the charge storage device 202 may be the edge of the charge storage device 202 that is adjacent to the coupler 324 and/or housing 102.

In some aspects, the step 2206 may additionally or alternatively include the computer 106 determining a midline of the implant 100. In some aspects, the computer 106 may be configured to determine the midline based on a location where the derivative of the changes in the magnetic field equals zero during movement of the sensor 105 across a longitudinal axis of the implant 100.

In some aspects, the process 2200 may include a step in which the computer 106 determines a depth of the implant 100 based on a magnitude of the change in the electromagnetic field at the bimodal peaks in the changes in the electromagnetic field during the movement of the sensor 105 along the longitudinal axis of the implant 100. In some aspects, the computer 106 may determine a depth of the implant 100 based on magnitudes of the changes in the electromagnetic field at the locations where the derivative of the changes in the electromagnetic field equals zero during the movement of the sensor 105 along the longitudinal axis of the implant 100.

In some aspects, the process 2200 may additionally or alternatively include a step in which the computer 106 determines an orientation of the implant 100. In some aspects, the computer 106 may determine the orientation based on a difference between magnitudes of the change in the electromagnetic field at the bimodal peaks in the changes in the electromagnetic field during the movement of the sensor 105 along the longitudinal axis of the implant 100 (e.g., after taking into account the expected difference between the magnitudes at the bimodal peaks due to the second edge of the charge storage device 202 being closer to the magnetic material 124 in the housing 102). In some aspects, the computer 106 may determine an orientation of the implant 100 based on a difference between magnitudes of the changes in the electromagnetic field at the locations where the derivative of the changes in the electromagnetic field equals zero during the movement of the sensor 105 along the longitudinal axis of the implant 100 (e.g., after taking into account the reduction in the magnitude of the bimodal peak in the changes in the electromagnetic field at the second edge of the charge storage device 202, which may be caused by the proximity of the second edge of the charge storage device 202 to the magnetic material 124).

In some aspects, the process 2200 may additionally or alternatively include computer 106 causing a display 129 to display an indication of the detected location of the implant 100. See, e.g., FIGS. 1 and 7A-7F. In some aspects, the indication of the detected location of the implant 100 may include an implant image 704, and a location of the implant image 704 on a screen 702 of the display 129 relative to a point 706 on the screen 702 of the display 129 may correspond to the detected location of the implant 100 relative to the sensor 105. In some aspects, the implant image 704 may have an orientation that corresponds to a detected orientation of the implant 100.

In some aspects in which the implant finder 101 includes the position detector 137 configured to generate a location signal indicative of a location of the sensor 105, the process 2200 may additionally or alternatively include a step in which the computer 106 uses the sensor signal and the location signal (e.g., a motion signal generated by a motion detector of the position detector 137 that is indicative of movement of the sensor 105) to generate a map of sensor signals at different locations of the sensor 105. In some aspects, generating a map of sensor signals at different locations of the sensor may include, for example and without limitation, measuring the sensor signal at each of two or more different locations of the sensor 105 and storing the measured sensor signals along with identifications of the locations at which the sensor signals were measured. In some aspects, generating a map of sensor signals at different locations of the sensor 105 may include generating a visualization of the measured sensor signals at the different locations of the sensor 105.

In some aspects, the process 2200 may include an optional step of removing the implant 100. In some aspects, removing the implant 100 may include making an incision at an identified edge of the charge storage device 202. In some aspects, removing the implant 100 may include grabbing (e.g., using forceps) the charge storage device 202 of the implant 100, which may be stronger than the housing 102 of the implant 100, and pulling the implant 100 out of the body through the incision.

Figure 23:
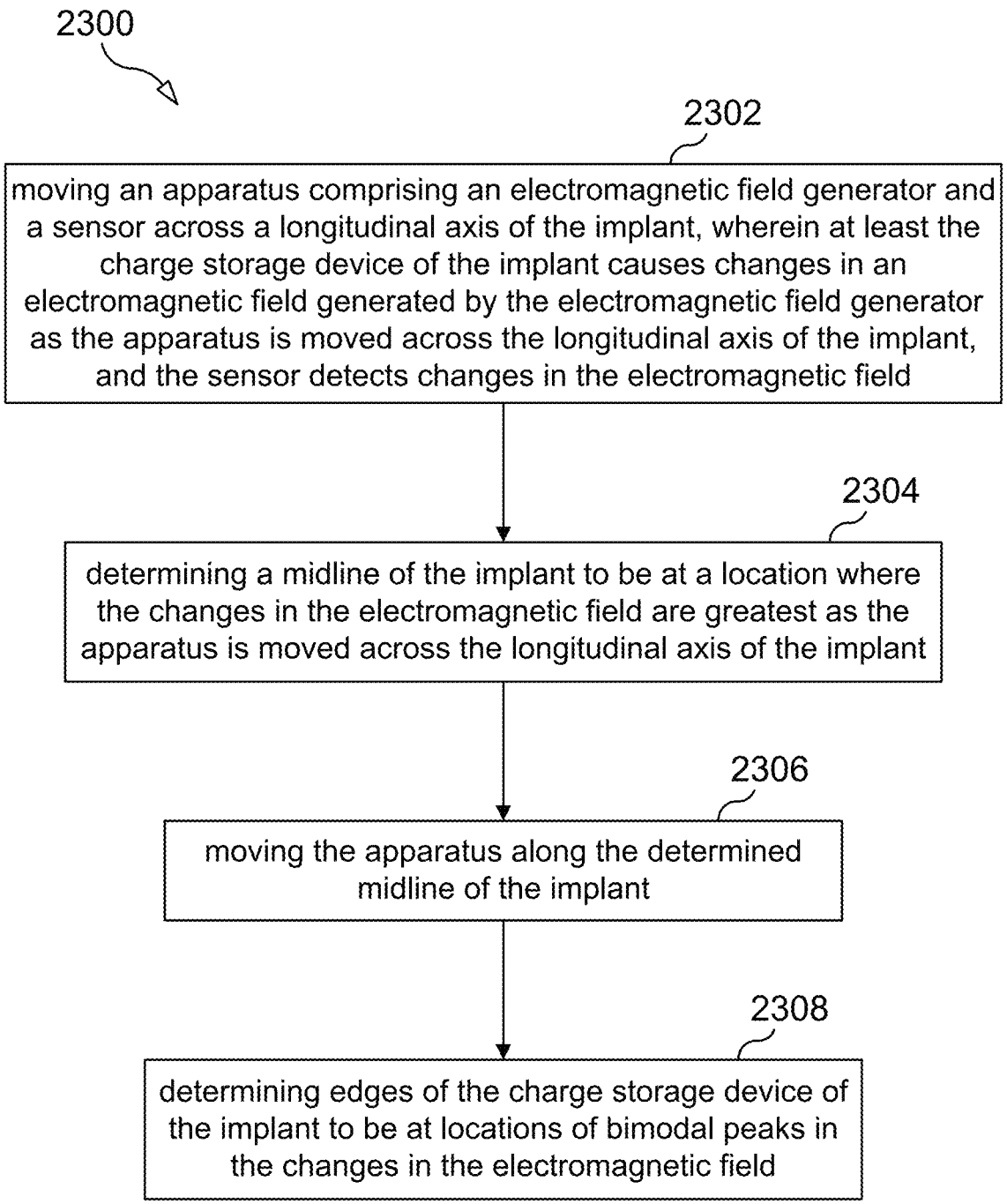
FIG. 23 is a flowchart illustrating a non-limiting example of a process for locating an implant including a charge storage device embodying aspects of the present invention.

FIG. 23 is a flow chart illustrating a process 2300 for locating an implant 100 including a charge storage device 202 according to some aspects. In some aspects, the process 2300 may include a step 2302 of moving an apparatus (e.g., implant finder 101) including an electromagnetic field generator 103' and a sensor 105 across a longitudinal axis of the implant 100. In some aspects, at least the charge storage device 202 of the implant 100 may cause changes in an electromagnetic field generated by the electromagnetic field generator 103' as the apparatus is moved across the longitudinal axis of the implant 100, and the sensor 105 may detect changes in the electromagnetic field. In some aspects, the process 2300 may include a step 2304 of determining a midline of the implant 100 based on a location where the changes in the electromagnetic field are greatest as the apparatus is moved across the longitudinal axis of the implant 100. In some aspects, the process 2300 may include a step 2306 of moving the apparatus along the determined midline of the implant 100. In some aspects, the process 2300 may include a step 2308 of determining edges of the charge storage device 202 of the implant 100 based on locations of bimodal peaks in the changes in the electromagnetic field. In some aspects, the process 2300 may include an optional step of using an incision marking tool 113 of the apparatus to mark an incision location for removing the implant 100. In some aspects, the incision location may be at or near the location of the bimodal peak in the changes in the electromagnetic field that has the greater magnitude. In some aspects, the process 2300 may include an optional step of removing the implant 100. In some aspects, removing the implant 100 may include making an incision at the incision location. In some aspects, removing the implant 100 may include grabbing (e.g., using forceps) the charge storage device 202 of the implant 100, which may be stronger than the housing 102 of the implant 100, and pulling the implant 100 out of the body through the incision.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. An apparatus for locating an implant comprising magnetic material in a living animal, the apparatus comprising:
   a magnetic field generator configured to generate a magnetic field;
   a sensor configured to detect changes in the magnetic field and to generate a sensor signal indicative of the changes in the magnetic field, wherein the magnetic material of the implant causes changes to the magnetic field as the sensor is moved over the implant; and
   a computer configured to use the sensor signal to detect a location of the implant, wherein, in detecting the location of the implant, the computer is configured to determine edges of the magnetic material of the implant based on locations of bimodal peaks in the changes in the magnetic field during movement of the sensor along a longitudinal axis of the implant.

2. The apparatus of claim 1, wherein the magnetic field generator comprises a cylindrical magnet.

3. The apparatus of claim 2, wherein the cylindrical magnet is hollow.

4. The apparatus of claim 1, wherein the magnetic field generator comprises two or more magnets.

5. The apparatus of claim 4, wherein the magnetic field generator further comprises a housing configured to hold the two or more magnets.

6. The apparatus of claim 4, wherein the magnetic field generator comprises four magnets.

7. The apparatus of claim 4, wherein the magnetic field generator comprises six magnets.

8. The apparatus of claim 1, wherein the magnetic field generator comprises one or more permanent magnets.

9. The apparatus of claim 1, wherein the magnetic field generator comprises one or more electromagnets.

10. The apparatus of claim 1, wherein the magnetic field generated by the magnetic field generator is a substantially uniform magnetic field.

11. The apparatus of claim 1, wherein the magnetic field is substantially symmetric about a longitudinal axis at a center of the magnetic field generator.

12. The apparatus of claim 11, wherein the sensor is located along or offset from the longitudinal axis at the center of the magnetic field generator.

13. The apparatus of claim 1, wherein the magnetic field is non-uniform and/or asymmetric about a longitudinal axis at a center of the magnetic field generator.

14. The apparatus of claim 1, wherein the computer is configured to determine edges of the implant based on the determined edges of the magnetic material of the implant and one of more off sets between edges of the implant and edges of the magnetic material of the implant.

15. The apparatus of claim 1, wherein the computer is configured to determine a depth of the implant based on a magnitude of the change in the magnetic field at the bimodal peaks in the changes in the magnetic field during the movement of the sensor along the longitudinal axis of the implant.

16. The apparatus of claim 1, wherein the computer is configured to determine an orientation of the implant based on a difference between magnitudes of the change in the magnetic field at the bimodal peaks in the changes in the magnetic field during the movement of the sensor along the longitudinal axis of the implant.

17. The apparatus of claim 1, wherein the computer is further configured to use one or more sensor signals to detect an orientation of the implant.

18. The apparatus of claim 1, further comprising a display, and the computer is configured to cause the display to display an indication of the detected location of the implant.

19. The apparatus of claim 18, wherein the display is located above the sensor.

20. The apparatus of claim 18, wherein the indication of the detected location of the implant comprises an implant image, and a location of the implant image on a screen of the display relative to a point on the screen of the display corresponds to the detected location of the implant relative to the sensor.

21. The apparatus of claim 20, wherein the implant image has an orientation that corresponds to a detected orientation of the implant.

22. The apparatus of claim 1, further comprising an incision marking tool configured to identify an incision location for removing the implant.

23. The apparatus of claim 1, further comprising a position detector configured to generate a location signal indicative of a location of the sensor on a skin surface.

24. The apparatus of claim 23, wherein the position detector comprises a motion detector configured to detect movement of the sensor and to generate a motion signal indicative of the detected movement of the sensor, wherein the location signal comprises the motion signal.

25. The apparatus of claim 23, wherein the computer is configured to use the sensor signal and the location signal to generate a map of sensor signals at different locations of the sensor on the skin surface.

26. An apparatus for locating an implant comprising magnetic material in a living animal, the apparatus comprising:
a magnetic field generator configured to generate a magnetic field;
a sensor configured to detect changes in the magnetic field and to generate a sensor signal indicative of the changes in the magnetic field, wherein the magnetic material of the implant causes changes to the magnetic field as the sensor is moved over the implant; and
a computer configured to use the sensor signal to calculate a derivative of the changes in the magnetic field and to use the calculated derivative to detect a location of the implant, wherein the computer is configured to determine edges of the magnetic material of the implant based on locations where the derivative of the changes in the magnetic field equals zero during movement of the sensor along a longitudinal axis of the implant.

27. The apparatus of claim 26, wherein the computer is configured to determine a depth of the implant based on magnitudes of the changes in the magnetic field at the locations where the derivative of the changes in the magnetic field equals zero during the movement of the sensor along the longitudinal axis of the implant.

28. The apparatus of claim 26, wherein the computer is configured to determine an orientation of the implant based on a difference between magnitudes of the changes in the magnetic field at the locations where the derivative of the changes in the magnetic field equals zero during the movement of the sensor along the longitudinal axis of the implant.

29. An apparatus for locating an implant comprising magnetic material in a living animal, the apparatus comprising:
a magnetic field generator configured to generate a magnetic field;
a sensor configured to detect changes in the magnetic field and to generate a sensor signal indicative of the changes in the magnetic field, wherein the magnetic material of the implant causes changes to the magnetic field as the sensor is moved over the implant; and
a computer configured to use the sensor signal to calculate a derivative of the changes in the magnetic field and to use the calculated derivative to detect a location of the implant, wherein the computer is configured to determine a midline of the implant based on a location where the derivative of the changes in the magnetic field equals zero during movement of the sensor across a longitudinal axis of the implant.

30. A method for locating an implant comprising magnetic material in a living animal, the method comprising:
using a magnetic field generator to generate a magnetic field;
using a sensor to detect changes in the magnetic field and to generate a sensor signal indicative of the changes in the magnetic field, wherein the magnetic material of the implant causes changes to the magnetic field as the sensor is moved over the implant; and
using a computer to detect a location of the implant based on the sensor signal, wherein detecting the location of the implant comprises determining edges of the magnetic material of the implant based on locations of bimodal peaks in the changes in the magnetic field during movement of the sensor along a longitudinal axis of the implant.

\* \* \* \* \*